(12) United States Patent
Ivashchenko et al.

(10) Patent No.: US 8,541,437 B2
(45) Date of Patent: Sep. 24, 2013

(54) SUBSTITUTED 2,3,4,5-TETRAHYDRO-1H-PYRIDO[4,3-B]INDOLES, METHODS FOR THE PRODUCTION AND USE THEREOF

(75) Inventors: Andrey Alexandrovich Ivashchenko, Moscow (RU); Alexandre Vasilievich Ivachtchenko, Encinitas, CA (US); Sergey Yevgenievich Tkachenko, San Diego, CA (US); Evgueni Borisovich Frolov, San Diego, CA (US); Oleg Dmitrievich Mitkin, Moscow Region (RU); Dmitri Vladimirovich Kravchenko, Moscow Region (RU); Ilya Matusovich Okun, San Diego, CA (US); Nikolay Filippovich Savchuk, Rancho Santa Fe, CA (US); Yan Lavrovsky, San Diego, CA (US)

(73) Assignee: Alla Chem, LLC, Carson City, NV (US)

( * ) Notice: Subject to any disclaimer, the term of this patent is extended or adjusted under 35 U.S.C. 154(b) by 752 days.

(21) Appl. No.: 12/594,453

(22) PCT Filed: Apr. 1, 2008

(86) PCT No.: PCT/RU2008/000196
§ 371 (c)(1),
(2), (4) Date: Oct. 2, 2009

(87) PCT Pub. No.: WO2008/123796
PCT Pub. Date: Oct. 16, 2008

(65) Prior Publication Data
US 2010/0120792 A1    May 13, 2010

(30) Foreign Application Priority Data
Apr. 5, 2007  (RU) ................. 2007112666

(51) Int. Cl.
*C07D 471/04* (2006.01)
*A61K 31/437* (2006.01)

(52) U.S. Cl.
USPC ............................. 514/290; 546/80

(58) Field of Classification Search
USPC ............................. 546/80; 514/290
See application file for complete search history.

(56) References Cited

U.S. PATENT DOCUMENTS

| | | | | |
|---|---|---|---|---|
| 3,484,449 A * | 12/1969 | Leo et al. | | 546/329 |
| 3,502,688 A * | 3/1970 | Leo et al. | | 546/86 |
| 6,187,785 B1 | 2/2001 | Zefirov | | |
| 7,935,823 B2 * | 5/2011 | Aksinenko et al. | | 546/82 |
| 2008/0234310 A1 | 9/2008 | Bachurin | | |

FOREIGN PATENT DOCUMENTS

| | | | |
|---|---|---|---|
| JP | 09216882 | | 8/1997 |
| RU | 2106864 | | 3/1998 |
| RU | 2140417 | | 10/1999 |
| RU | 2283108 | | 9/2006 |
| WO | WO9715225 | * | 3/1997 |
| WO | WO 2005/055951 | | 6/2005 |
| WO | WO 2005055951 | * | 6/2005 |
| WO | WO2009055828 | * | 4/2009 |
| WO | WO 2009120717 | * | 10/2009 |

OTHER PUBLICATIONS

Chem Abstract DN 69:9497 Verkhovskii Yu et al 1968.*
Barry, P.H. et al., 'Ligand-gated channels' IEEE Trans Nanobioscience vol. 4, No. 1, 2005, pp. 70-80.
Berge, S.M. et al., 'Pharmaceutical Salts' J.Pharm.Sci. vol. 66, 1977, pp. 1-19.
Choi, D.W., Neuron, vol. 1, 1988, pp. 623-634.
Davies, S.L.: 'Drug discovery targets: 5-HT6 receptor', Drug Future, vol. 30, 2005, pp. 479-495.
Dawson, L.A. et al., 'The 5-HT(6) receptor antagonist SB-271046 selectively enhances excitatory neurotransmission in the rat frontal cortex and hippocampus', Neuropsychopharmacology, vol. 25, 2001, pp. 662-668.

(Continued)

*Primary Examiner* — Rita Desai
(74) *Attorney, Agent, or Firm* — Sughrue Mion, PLLC

(57) ABSTRACT

The invention relates to antagonists of serotonin 5-$HT_6$ receptors simultaneously regulating homeostasis of $Ca^{+2}$ ions in cells, representing substituted 2,3,4,5-tetrahydro-1H-pyrido[4,3-b]indoles of the general formula 1, pharmaceutically acceptable salts and/or hydrate thereof. In the general formula 1:

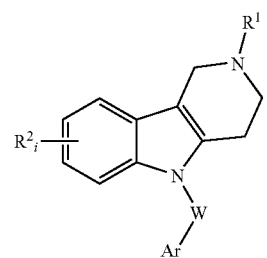

Figure 1:
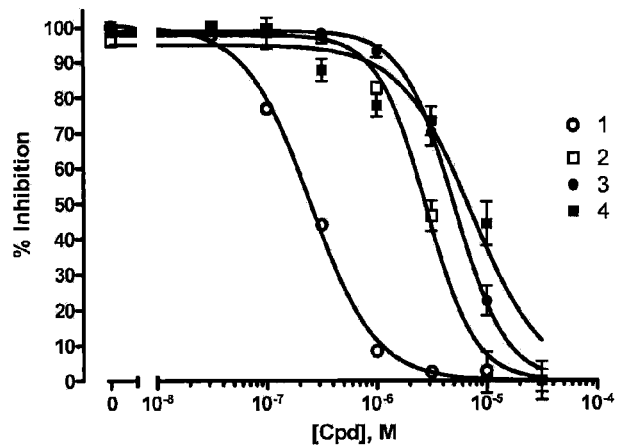

$R^1$ represents amino group substituent selected from optionally substituted $C_1$-$C_5$ alkyl; $R^2_i$ is one or more substituents selected from hydrogen, halogen, $C_1$-$C_3$ alkyl, $CF_3$, $OCF_3$; Ar is phenyl optionally substituted with halogen, $C_1$-$C_6$ alkyl, $C_1$-$C_6$ alkoxy, substituted amino group, or $CF_3$; or optionally substituted aromatic 6-membered heterocycle comprising 1-2 nitrogen atoms in the cycle; W represents ethylene group —$CH_2$—$CH_2$—, ethenyl group —CH═CH—, or ethynyl group —C≡C—. The invention also relates to the novel compounds selected from the compounds of the general formula 1, methods for their preparation, pharmaceutical compositions and methods of their use.

11 Claims, 11 Drawing Sheets

(56) References Cited

OTHER PUBLICATIONS

Foley, A.G. et al., 'The 5-HT(6) receptor antagonist SB-271046 reverses scopolamine-disrupted consolidation of a passive avoidance task and ameliorates spatial task deficits in aged rats' Neuropsychopharmacology vol. 29, 2004, pp. 93-100.

Gankina, E.M. et al., "Effect of antihistamine drugs on labelled mepyramine, ketanserin, and quinuclidinyl benzylate in the rat brain", Exp and Clin Pharmacology (Moscow) 56(1);22-24, 1993 Abstract only.

Ge'rard C. et al., 'Immuno-localization of serotonin 5-HT6 receptor-like material in the rat central nervous system', Brain Research, vol. 746, 1997, pp. 207-219.

Holenz, J. et al., 'Medicinal chemistry strategies to 5-HT6 receptor ligands as potential cognitive enhancers and antiobesity agents', Drug Disc. Today vol. 11, 2006, pp. 283-299.

Horlein, U. et al., Med.-Chem., Abhandl. Med.-Chem. Forschungsstatten Farbenfabriken Bayer (1956), 5, 267-80.

Ivanov, Yu.Ya. et al., "Calcium-Antagonist Activity of Some Hydrogenated Pyrido[4,3-B]Indole Derivatives", Pharmaceutical Chemistry Journal, vol. 35 No. 7, 2001 p. 7.

McDonald, J. W. et al., "Physiological and pathophysiological roles of excitatory amino acids during central nervous system development", Brain Res. Rev., vol. 15, 1990, pp. 41-70.

Kiewert, C. et al., 'NGPI-01 is a Brain-permeable Dual Blocker of Neuronal Voltage- and Ligand-operated Calcium Channels', Neurochem. Res. 31(3):395-9, 2006.

King, M.V. et al., '5-HT6 receptor antagonists reverse delay-dependent deficits in novel object discrimination by enhancing consolidation an effect sensitive to NMDA receptor antagonism', Neuropharmacology vol. 47, 2004, pp. 195-204.

Kost, J., Gen. Chem. USSR (Engl. Transl.), v 33, 1963, p. 3538.

Lermontova, N.N. et al., "Dimebon and tacrine inhibit neurotoxic action of beta-amyloid in culture and block L-type Ca2+ channels", Bulletin Exp Biol and Med, 132(5):1079-83, 2001.

Lermontova, N.N. et al., Bull Exp Biol Med 129(6), 544-546, 2000.

Mashkovsky, M.D., Pharmaceuticals. Pub. 13. Kharkov: Torsing, 1998. v.1. p. 280-281.

Barbulescu, N. et al., "Synthesis of some 1,2,3,4-tetrahydro-γ-carbolines", Rev. Chim. (Bucuresti) vol. 22, 1971, p. 269.

Riemer, C. et al.: 'Bos M. Influence of the 5-HT6 receptor on acetylcholine release in the cortex: pharmacological characterization of 4-(2-bromo-6-pyrrolidin- I -ylpyridine-4-sulfonyl)phenylamine, a potent and selective 5-HT6 receptor antagonist', J Med. Chem., vol. 46, 2003, pp. 1273-1276.

Rogawski, M. et al., "The Neuropharmacological Basis for the Use of Memantine in the Treatment of Alzheimer's Disease", CNS Drug Rev. vol. 9, No. 3, 2003, pp. 275-308.

Sayer, R.J., 'Intracellular Ca2+ handling', Adv Exp Med Biol. vol. 513, 2002, pp. 183-196.

Sica, D.A., 'Pharmacotherapy review: calcium channel blockers', J Clin Hypertens (Greenwich) vol. 8, No. 1, 2006, pp. 53-56.

Stys, P.K., 'General mechanisms of axonal damage and its prevention', J Neurol Sci. vol. 233, No. 1-2, 2005, pp. 3-13.

Verkhovskii, Chem.Abstr. 69:9497. Toxicological and antiserotonin properties of γ-carboline derivatives. Farmakologiya I Toksikologiya (Moscow) 31(2):209-213 1968.

Vicker, S.P. et al., 'Serotonin receptor ligands and the treatment of obesity', Curr. Opin. Investig. Drugs vol. 5, 2004, pp. 377-388.

Woolley, M.L., '5-ht6 receptors', Curr. Drug Targets Cns Neurol. Disord. vol. 3, 2004, pp. 59-79.

Zhurnal Obshchei Khimii, Nauka, Moscow, RU vol. 33(11):3606-13, 1963, p. 3607, compound X.

\* cited by examiner

SUBSTITUTED 2,3,4,5-TETRAHYDRO-1H-PYRIDO[4,3-B]INDOLES, METHODS FOR THE PRODUCTION AND USE THEREOF

CROSS REFERENCE TO RELATED APPLICATIONS

This application is a 35 USC §371 National Stage application of International Application No. PCT/RU2008/000196 filed Apr. 1, 2008, now pending; which claims the benefit under 35 USC §119(a) of Russia Patent Application No. 2007112666 filed Apr. 5, 2007. The disclosure of each of the prior applications is considered part of and is incorporated by reference in the disclosure of this application.

FIELD OF THE INVENTION

The invention relates to the novel chemical compounds, methods for their preparation and use as 5-HT$_6$ serotonin receptor antagonists, simultaneously regulating homeostasis of calcium ions in cells. More specifically, the invention relates to the novel annelated azaheterocycles-2,3,4,5-tetrahydro-1H-pyrido[4,3-b]indoles, optical and geometrical isomers, racemic mixtures, pharmaceutically acceptable salts and/or hydrates thereof, to methods for their preparation, to pharmaceutical compositions, including these compounds as active ingredients, and to methods of treatment and prophylaxis of various diseases, among them neurodegenerative diseases such as schizophrenia or Alzheimer's disease, associated with the excessive penetration of calcium ions into nerve cells, that initiates the whole number of pathological metabolic processes, finally inducing death of neurons [D. W. Choi, *Neurone,* 1988; 1:623-634].

BACKGROUND OF THE INVENTION

The pharmacological action of 2,3,4,5-tetrahydro-1H-pyrido[4,3-b]indoles rests on their ability to reduce effectively the cytozolic concentration of calcium ions, when intracellular concentration of calcium ions has become excessive as a result of various pathological processes. Besides, these compounds are effective antagonists of 5-HT$_6$ serotonin receptors, playing an important role in treatment diseases associated with central nervous system (CNS), such as Alzheimer's disease, Huntington's disease, schizophrenia or other neurodegenerative diseases, and obesity.

Maintenance of low concentration of calcium ions is extremely important for normal cell functioning, because the prolonged enhancement of Ca$^{+2}$ percentages in cytozole leads to apoptosis. Such mechanism of apoptosis is a characteristic feature of all neurodegenerative diseases, that is why the searching for pharmacological remedies preventing excessive penetration of Ca$^{+2}$ ions into neurons is one of the most important trend in neuroprotector development [Kiewert C., Hartmann J., Stoll J., Thekkumkara T. J., Van der Schyf C. J., Klein J. NGP1-01 is a Brain-permeable Dual Blocker of Neuronal Voltage- and Ligand-operated Calcium Channels. *Neurochem. Res.* 2006 May 3]. Cytozolic Ca$^{+2}$ concentration in eucariotic cells is regulated by transmembrane transport and by cytoplasm calcium binding [Sayer R. J. Intracellular Ca2+ handling. *Adv Exp Med Biol.* 2002; 513:183-96].

Obviously, the various proteins supporting calcium homeostasis in cytoplasm play an extraordinary role in pathogenesis of such neuralgic disorders as hypoxia-ischemia, hypoglycemia, convulsive conditions, cerebral traumas and also chronic neurodegenerative diseases (including Alzheimer's disease, Huntington's chorea, lathyrism, lateral amyotrophic sclerosis). [J. W. McDonald, M. V. Johnston—*Brain Res. Rev.,* 1990; 15:41-70; Stys P. K. General mechanisms of axonal damage and its prevention. *J Neurol Sci.* 2005; 233(1-2):3-b]. The possibility of pool regulation of intracellular Ca$^{+2}$ concentration determines the great pharmacological role of selective blockers/activators of various potential dependent calcium channels (for example, T-, L-, N—, P—, Q- and R— channels) and specific antagonist/modulator of ligand-gated channels (for example, NMDA-, AMPA-, nAChR-, P2X-receptors) [Barry P. H., Lynch J. W. Ligand-gated channels. IEEE Trans Nanobioscience. 2005; 4(1):70-80]. At present a great number of such calcium transport effectors are offered as highly effective medicaments. For example, calcium antagonists—is a group of drugs the common feature of which is the ability to reversible blocking of calcium flow through potential-dependent calcium channels. Judging by their chemical structure these drugs could be divided into two large subgroups dihydropyridines (Nifedipine, Amlodipine, Felodipine and others), in the properties of which the effect of peripheric vasodilatation is predominated, and nondihydropyridines (Verapamil and Diltiazem), the main properties of which is negative chrono- and inotropic action and the ability to reduce atrioventricular conductibility as well [Sica D. A. Pharmacotherapy review: calcium channel blockers. [J Clin Hypertens (Greenwich). 2006; 8(1): 53-6]. An example of a drug blocking an excessive penetration of calcium ions into neurons through ligand-gated channels (NMDA) is Memantine, widely used at present in the treatment of Alzheimer's disease [Rogawski M. A., Wenk G. L. The neuropharmacological basis for the use of Memantine in the treatment of Alzheimer's disease. [*CNS Drug Rev.* 2003; 9(3):275-308]. Nearly all mentioned drugs prevent the excessive penetration of calcium ions into cells, however, calcium homeostasis modulators capable to effective reducing of calcium cytosolic concentration which became excessive as a result of some pathologic processes have not been known yet Use of effective and selective antagonists of 5-HT$_6$ serotonin receptors for treatment diseases associated with CNS, in particular, schizophrenia, Alzheimer's disease and other neurodegenerative diseases is a perspective direction for the development of novel drugs [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299]. At mammals these receptors are found exclusively in the central nervous system (CNS), mainly, in the regions of brain responsible for training and memory [Ge'rard C., Martres M.-P., Lefe'vre K., Miquel M.-C., Verge' D., Lanfurney L., Doucet E., Hamon M., El Mestikawy S. Immuno-localisation of serotonin 5-HT$_6$ receptor-like material in the rat central nervous system. [*Brain Research.* 1997; 746:207-219]. Moreover, it was shown [Dawson L. A., Nguyen H. Q., Li P. The 5-HT(6) receptor antagonist SB-271046 selectively enhances excitatory neurotransmission in the rat frontal cortex and hippocampus. [*Neuropsychopharmacology.* 2001; 25:662-668], that 5-HT$_6$ receptors are modulators of several neuromediator systems, including cholinergic, noradrenergic, glutamatergic and dopaminergic. Bearing in mind the fundamental role of these systems in normal cognitive processes and also their dysfunction at neurodegeneration, it becomes obvious an exclusive role of 5-NT$_6$ receptors in the functioning of normal or "pathological" memory. In many current publication it was shown, that blocking of 5-HT$_6$ receptors leads to considerable enhancement of memory consolidation in various animal models of training—memorizing—reproduction [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology.* 2004; 29:93-100. Riemer C., Borroni E., Levet-Trafit B., Martin J. R., Poli S., Porter R. H., Bos M. Influence of the 5-HT$_6$ receptor on acetylcholine release in the cortex: pharmacological characterization of 4-(2-bromo-6-pyrrolidin-1-ylpyridine-4-sulfonyl)phenylamine, a potent and selective 5-HT$_6$ receptor antagonist. *J. Med. Chem.* 2003; 46:1273-1276. King M. V., Woolley M. L., Topham I. A., Sleight A. J., Marsden C. A., Fone K. C. 5-HT$_6$ receptor antagonists reverse delay-dependent deficits in novel object discrimination by enhancing consolidation an effect sensitive to NMDA receptor antagonism. Neuropharmacology 2004; 47:195-204]. It was also shown significant improvement of cognitive functions in aged rats in a model of Morris water Maze under the action of 5-HT$_6$ receptor antagonists [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology.* 2004; 29:93-100]. Recently, not merely the more fundamental understanding of 5-HT$_6$ receptors role in cognitive processes was achieved, but also more unambiguous conception concerning pharmacophor possibilities of their antagonists [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. [*Drug Disc. Today.* 2006; 11:283-299]. It resulted in creation of high-affinity selective ligandes ("molecular tools"), and then clinical candidates. Now the whole number of 5-HT$_6$ receptor antagonists are at various stages of clinical tests as drug candidates for treatment Alzheimer's disease, Huntington's disease, schizophrenia (antipsychotics) and other neurodegenerative and cognitive diseases (Table 1) [http://integrity.prous.com].

TABLE 1

5-HT$_6$ receptor antagonists as drug candidates.

| Drug | Clinical phase of testing | Sponsor | Therapeutic group |
| --- | --- | --- | --- |
| Dimebon ™ | Phase III | Medivation (USA) | Treatment of Alzheimer's disease |

TABLE 1-continued

5-HT$_6$ receptor antagonists as drug candidates.

| Drug | Clinical phase of testing | Sponsor | Therapeutic group |
| --- | --- | --- | --- |
| SGS-518 | Phase II | Lilly, Saegis | Treatment of cognitive diseases |
| SB-742457 | Phase II | GlaxoSmithKline | Treatment of Alzheimer's disease; Antipsychotic |
| Dimebon* | Phase I/IIa | Medivation (USA) | Treatment of Huntington's disease |
| Dimebon* | Phase II | (Russia) | Antipsychotic |
| PRX-07034 | Phase I | Epix Pharm. | Treatment of overweight; Antipsychotic; Treatment of cognitive diseases |
| SB-737050A | Phase II | GlaxoSmithKline | Antipsychotic |
| BVT-74316 | Phase I | Biovitrum | Treatment of overweight; |
| SAM-315 | Phase I | Wyeth Pharm. | Treatment of Alzheimer's disease |
| SYN-114 | Phase I | Roche, Synosis Ther. | Treatment of cognitive diseases |
| BGC-20-761 | Preclinical phase | BTG (London) | Antipsychotic; Treatment of cognitive diseases |
| FMPO | Preclinical phase | Lilly | Antipsychotic |
| Dimebon ™ | Preclinical phase | (Russia) | Treatment of Insult |

*in the process of this investigation the authors discovered for the first time that Dimebon is 5-HT$_6$ receptor antagonist and simultaneously regulates homeostasis of calcium ions in cells.

Another attractive property of 5-HT$_6$ receptor antagonists is their ability to suppress appetite that can lead to creation on their bases principally novel remedies for treatment of overweight and obesity [Vicker S. P., Dourish C. T. Serotonin receptor ligands and the treatment of obesity. *Curr. Opin. Investig. Drugs.* 2004; 5:377-388]. This effect was confirmed in many investigations [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299. Davies S. L. Drug discovery targets: 5-HT$_6$ receptor. *Drug Future.* 2005; 30:479-495], mechanism of its functioning is based upon suppression of γ-aminobutyric acid signaling by 5-HT$_6$ receptor antagonists and increasing α-melanocyte-stimulating hormone emission, that, eventually, leads to reduction of food consumption [Woolley M. L. 5-ht6 receptors. *Curr. Drug Targets CNS Neurol. Disord.* 2004; 3:59-79]. At present two 5-HT$_6$ receptor antagonists are at the first phase of clinical testing as drug candidates for weight-reducing treatment (Table 1) [http://integrity.prous.com].

In this context searching for effective neuroprotectors capable to prevent the neurotoxic action of excessive cytosolic calcium and also searching for effective serotonin 5-HT$_6$ receptor antagonists are seemed to be original and perspective approach to design of novel drug substances for treatment of broad spectrum of neuralgic and neurodegenerative diseases.

There are many publications concerning various biologically active 2,3,4,5-tetrahydro-1H-pyrido[4,3-b]indoles, some of them are represented in Table 2.

TABLE 2

Some examples of known 2,3,4,5-tetrahydro-1H-pyrido[4,3-b]indoles

| No | Formula | Pharmacological activity | Reference |
|----|---------|--------------------------|-----------|
| A1 | | Antihistaminic substance | Horlein, Ulrich; Hecht, Gerhard. Med. -Chem., Abhandl. Med.-Chem. Forschungsstatten Farbenfabriken Bayer (1956), 5, 267-80. |
| A2 | | | Kost, J. Gen. Chem. USSR (Engl. Transl.), v. 33, 1963, p. 3538. |
| A3 | | Antagonist NMDA-brain receptors. Antihistaminic and neuroprotective substance, Alzheimer's disease | Mashkovsky M.D. Pharmaceuticals. Pub. 13. Kharkov: Torsing, 1998. v.1. p. 280-281. Bull Exp Biol Med. 2000, 129(6) 544-546. U.S. Pat. No. 6187785 (2001) JP 09216882 (1997) RU 2140417 (1999) |

TABLE 2-continued

Some examples of known 2,3,4,5-tetrahydro-1H-pyrido[4,3-b]indoles

| No | Formula | Pharmacological activity | Reference |
|---|---|---|---|
| A4 | 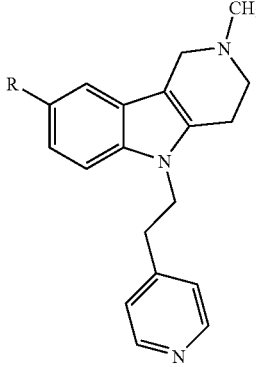<br>R = H, CH₃, CF₃, CO₂H, CO₂C₂H₅ | Analgesics | U.S. Pat. No. 3,502,688 (1972) |

For the purpose of searching for novel highly effective neuroprotective drug substances the authors of the invention carried out a broad investigation in the field of substituted 2,3,4,5-tetrahydro-1H-pyrido[4,3-b]indoles; as a result of which new biologically active substances, which are 2,3,4,5-tetrahydro-1H-pyrido[4,3-b]indoles substituted in a certain manner, among them the novel ones, were found.

DISCLOSURE OF THE INVENTION

In the context of the present invention, the terms are generally defined as follows:

"Azaheterocycle" means an aromatic or nonaromatic mono- or polycyclic system with at least one nitrogen atom. Azaheterocycle may have one or more "cyclic system substituents".
"Aliphatic radical" radical means the radical derived at removal of hydrogen atom from nonaromatic C—H bond. Aliphatic radical may additionally contain any substituens—aliphatic or aromatic radicals, the meanings of which are defined in this section. The representatives of aliphatic radicals include: alkyl, alkenyl, alkynyl, cycloalkyl, cycloalkenyl, heterocyclyl, heterocyclenyl, aralkenyl, aralkyloxyalkyl, aralkyloxycarbonylalkyl, aralkyl, aralkynyl, aralkyloxyalkenyl, heteroaralkenyl, heteroaralkyl, heteroaralkyloxyalkenyl, heteroaralkyloxyalkyl, heteroaralkenyl, annelated arylcycloalkyl, annelated heteroarylcycloalkyl, annelated arylcycloalkenyl, annelated heteroarylcycloalkenyl, annelated arylheterocyclyl, annelated heteroarylheterocyclyl, annelated arylheterocyclenyl, annelated heteroarylheterocyclenyl.

"Alkenyl" means an aliphatic straight- or branched-hydrocarbon chain with 2-7 carbon atoms including C═C double bond. "Branched" means that one or several lower alkyl substituents, such as methyl, ethyl or propyl are attached to the straight alkenyl chain. Alkyl substituent may have one or more substituents such as: halogen, alkenyloxy, cycloalkyl, cyano; hydroxy, alkoxy, carboxy, alkynyloxy, aralkoxy, aryloxy, aryloxycarbonyl, alkylthio, heteroaralkyloxy, heterocyclyl, heterocyclylalkyloxy, alkoxycarbonyl, aralkoxycarbonyl, heteroaralkoxycarbonyl or $R_k{}^a R_{k+1}{}^a N-$, $R_k{}^a R_{k+1}{}^a NC(\!\!=\!\!O)-$, $R_k{}^a R_{k+1}{}^a NSO_2-$, where $R_k{}^a$ and $R_{k+1}{}^a$ independently of each other represent "amino group substituents", the meaning of which are defined in this section, for example, hydrogen, alkyl, aryl, aralkyl, heteroaralkyl, heterocyclyl or heteroaryl, or $R_k{}^a$ and $R_{k+1}{}^a$ together with the N-atom they are attached to, form through $R_k{}^a$ and $R_{k+1}{}^a$ 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, benzyloxycarbonylmethyl, and pyridylmethyloxycarbonylmethyl. The preferred alkenyl groups are ethenyl, propenyl, n-butenyl, iso-butenyl, 3-methylbuten-2-yl, n-pentenyl and cyclohexylbutenyl.

"Alkenyloxy" means alkenyl-O-group, in which alkenyl is defined in this section. Allyloxy and 3-butenyloxy are the preferred alkenyloxy groups.

"Alkenyloxyalkyl" means alkenyl-O-alkyl group, in which alkyl and alkenyl are defined in this section.

"Alkyl" means aliphatic hydrocarbon straight or branched chain with 1-12 carbon atoms. Branched means that the alkyl chain has one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k{}^a R_{k+1}{}^a N-$, $R_k{}^a R_{k+1}{}^a NC(\!\!=\!\!O)-$, $R_k{}^a R_{k+1}{}^a NC(\!\!=\!\!S)-$, $R_k{}^a R_{k-1}{}^a NSO_2-$, where $R_k{}^a$ and $R_{k+1}{}^a$ independently of each other represent "amino group substituents", the meanings of which are defined in this section, for example, hydrogen, alkyl, aryl, aralkyl, heteroaralkyl, heterocyclyl or heteroaryl, or $R_k{}^a$ and $R_{k+1}{}^a$ together with the N-atom, they are attached to, form through $R_k{}^a$ and $R_{k+1}{}^a$ 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl and pyridilmethyloxycarbonylmethyl. The preferred "alkyl substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k{}^a R_{k+1}{}^a N-$, $R_k{}^a R_{k+1}{}^a NC(=O)-$, annelated arylheterocyclenyl, annelated arylheterocyclyl.

"Alkyloxyalkyl" means alkyl-O-alkyl group, wherein alkyl groups are independent of one another and defined in this section. The preferred alkyloxyalkyl groups are methoxyethyl, ethoxymethyl, n-butoxymethyl, methoxypropyl and iso-propyloxyethyl.

"Alkoxycarbonyl" means alkyl-O—C(=O)— group, wherein alkyl is defined in this section. The preferred alkoxycarbonyl groups are methoxycarbonyl, ethoxycarbonyl, n-butoxycarbonyl, iso-propyloxycarbonyl, benzyloxycarbonyl and phenethyloxycarbonyl.

"Alkylthio" means alkyl-S group, wherein alkyl group is defined in this section.

"Alkoxy" means alkyl-O-group, wherein alkyl is defined in this section. The preferred alkoxy groups are methoxy, ethoxy, n-propoxy, iso-propoxy and n-butoxy.

"Alkoxycarbonylalkyl" means alkyl-O—C(=O)-alkyl-group, wherein alkyl is defined in this section. The preferred alkoxycarbonylalkyl groups are methoxy-carbonylmethyl, ethoxy-carbonylmethyl, methoxy-carbonylethyl and ethoxy-carbonylethyl.

"Amino group" means $R_k{}^a R_{k+1}{}^a N$-group substituted or not by "amino group substituent", the meanings of $R_k{}^a$ and $R_{k+1}{}^a$ are defined in this section, for example, amino ($NH_2$), methylamino, diethylamino, pyrrolidino, morpholino, benzylamino or phenethylamino.

"Amino acid" means a natural aminoacid or non-natural aminoacid, the meaning of the latter is defined in this section. The preferred amino acids are amino acids containing α- or β-amino group. Examples of natural amino acids are α-amino acids, and also alanine, valine, leucine, isoleucine, proline, phenylalanine, triptophane, methionine, glycine, serine, threonine, and cysteine.

"Amino-cyano-methylene" means $(NR_k{}^a R_{k-1}{}^a)(CN)C=$ group (radical) substituted or not by "amino group substituent" $R_k{}^a$ and $R_{k+1}{}^a$ the meanings of are defined in this section, for example, amino.

"Annelated cyclic structure" (condensed cyclic structure) means bi- or polycyclic system in which the annelated cyclic structure and cyclic structure, or polycyclic structure to which it is "annelated" have at least two common atoms.

"Annelated arylheterocycloalkenyl" means an annelated aryl and heterocycloalkenyl, the meanings of which are defined in this section. Annelated arylheterocycloalkenyl may be bound through any possible atom of its cyclic system. The prefixes "aza", "oxa" or "thia" preceding the word "heterocycloalkenyl" indicate the presence of a nitrogen atom, an oxygen atom, or a sulfur atom, respectively, in the cyclic system. Annelated arylheterocycloalkenyl may have one or more "cyclic system substituents" of the same or different structure. Nitrogen and sulfur atoms in the heterocycloalkenyl part may be oxidized to an N-oxide, an S-oxide or an S-dioxide. Annelated arylheterocycloalkenyl are represented by indolinyl, 1H-2-oxoquinolinyl, 2H-1-oxoisoquinolinyl, 1,2-dihydroquinolinyl, and so on.

"Annelated arylheterocycloalkyl" means an annelated aryl and heterocycloalkyl the meanings of which are defined in this section. Annelated arylheterocycloalkyl may be bound through any possible atom of its cyclic system. The prefixes "aza", "oxa" or "thia" preceding the word "heterocycloalkyl" indicate the presence of a nitrogen atom, an oxygen atom, or a sulfur atom, respectively, in the cyclic system. Annelated arylheterocycloalkyl may have one or more "cyclic system substituents" of the same or different structure. Nitrogen and sulfur atoms in the heterocyclyl part may be oxidized to an N-oxide, an S-oxide and an S-dioxide. Annelated arylheterocycloalkyls are represented by indolyl, 1,2,3,4-tetrahydroisoquinolinyl, 1,3-benzodiocolyl, and so on.

"Annelated arylcycloalkenyl" means an annelated aryl and cycloalkenyl, the meanings of which are defined in this section. Annelated arylcycloalkenyl may be bound through any possible atom of its cyclic system. Annelated arylcycloalkenyl may have one or more "cyclic system substituents" of the same or different structure. Annelated arylcycloalkenyls are represented by 1,2-dihydronaphthalenyl, indenyl and so on.

"Annelated arylcycloalkyl" means an annelated aryl and cycloalkyl, the meanings of which are defined in this section. Annelated arylcycloalkyl may be bound through any possible atom of its cyclic system. Annelated arylcycloalkyl may have one or more "cyclic system substituents" of the same or different structure. Annelated arylcycloalkyl are represented by indaninyl, 1,2,3,4-tetrahydranaphthyl, 5,6,7,8-tetrahydronapht-1-yl, and so on.

"Annelated heteroarylcycloalkenyl" means an annelated heteroaryl and cycloalkenyl, the meanings of which are defined in this section. Annelated heteroarylcycloalkenyl may be bound through any possible atom of its cyclic system. The prefixes "aza", "oxa" or "thia" preceding the word "heterocycloalkyl" indicate the presence of a nitrogen atom, an oxygen atom, or a sulfur atom, respectively, in the cyclic system. Annelated heteroarylcycloalkenyl may have one or more "cyclic system substituents" of the same or different structure. The nitrogen atom in the heteroaryl part may be oxidized to N-oxide. Annelated heteroarylcycloalkenyls are represented by 5,6-dihydroquinolinyl, 5,6-dihydroisoquinolinyl, 4,5-dihydro-1H-benzimidazolyl, and so on.

"Annelated arylcycloalkyl" means annelated aryl and cycloalkyl the meanings of which are defined in this section. Annelated arylcycloalkyl may be bound through any possible atom of its own system. Annelated arylcycloalkyl may have one or more "cyclic system substituents" of the same or different structure. Indaninyl, 1,2,3,4-tetrahydranaphth-1-yl and 5,6,7,8-tetrahydranaphth-1-yl and others could be used as an annelated arylcycloalkyl.

"Annelated heteroarylcycloalkenyl" means annelated heteroaryl and cycloalkenyl the meanings of which are defined in this section. Annelated heteroarylcycloalkenyl may be bound through any possible atom of its own cyclic system. Prefix "aza", "oxa" or "thia" before "heteroaryl" means that atoms N, O or S are introduced in the appropriate cyclic fragment. Annelated heteroarylcycloalkenyl may have one or more "cyclic system substituent" of the same or different structure. N-Atom in heteroaryl fragment could be oxidized to N-oxide. 5,6-Dihydroisoquinolinyl, 4,5-dihydro-1H-benzimidazolyl and others could be used as an annelated heteroarylcycloalkenyl.

"Annelated heteroarylcyckloalkyl" means annelated heteroaryl and cycloalkyl the meanings of which are defined in this section. Annelated heteroarylcycloalkyl may be bound through any possible atom of its own cyclic system. Prefix "aza", "oxa" or "thia" before "heteroaryl" means that atoms N, O or S are introduced in the appropriate cyclic fragment. Annelated heteroarylcycloalkyl may have one or more "cyclic system substituents" of the same or different structure. N-Atom in heteroaryl part of the molecule could be oxidized to N-oxide. 5,6,7,8-Tetrahydroquinolinyl, 5,6,7,8- tetrahydroisoquinolinyl, 4,5,6,7-tetrahydro-1H-benzoimidazolyl and others could be used as annelated heteroarylcycloalkenes.

"Annelated heteroarylhetrocyclenyl" means annelated heteroaryl and heterocyclenyl the meanings of which are defined in this section. Annelated heteroarylheterocyclenyl may be bound through any possible atom of its own cyclic system. Prefix "aza", "oxa" or "thia" before "heteroaryl" means that atoms N, O or S are introduced in the appropriate cyclic fragment. Annelated heteroarylheterocyclenyl may have one or more "cyclic system substituents" of the same or different structure. N-Atom of heteroaryl fragment could be oxidized to N-oxide. N- And S-atoms belonging to heterocyclenyl fragment could be oxidized to N-oxide, S-oxide and S-dioxide. 1,2-Dihydro[2,7]naphthiridinyl, 7,8-dihydro[1,7]naphthiridinyl, 6,7-dihydro-3H-imidazo[4,5-c]pyridinyl and others could be used as an annelated heteroarylhetrocyclenyl.

"Annelated heteroarylheterocyclyl" means annelated heteroaryl and heterocyclyl the meaning of which are defined in this section. Annelated heteroarylheterocyclyl may be bound through any possible atom of its own cyclic system. Prefix "aza", "oxa" or "thia" before "heteroaryl" means that atoms N, O or S are introduced in the appropriate cyclic fragment. Annelated heteroarylheterocyclyl may have one or more "cyclic system substituents" of the same or different structure. N-Atom belonging to heteroaryl fragment could be oxidized to N-oxide. N- and S-atoms of heterocyclyl fragment could be oxidized to N-oxide, S-oxide and S-dioxide. 2,3-Dihydro-1H-pyrrolo[3,4-b]quinolin-2-yl, 2,3-dihydro-1H-pyrrolo[3,4-b]indol-2-yl, 1,2,3,4-tetrahydro[1,5]naphthiridinyl and others could be used as annelated heteroarylcycloakenyls.

"Antagonists" mean ligands which are related with definite receptors and do not cause active cellular response. Antagonists prevent linkage of agonists and receptors and by that block specific transfer of the signal.

"Antidepressant" means a medicine intended for treatment of depression.

"Anxiolytic" (tranquilizer) means a medicine intended for treatment of anxious disorders.

"Aralkenyl" means aryl-alkenyl group, the meanings of aryl and alkenyl are defined in this section. For example, 2-phenethenyl is aralkenyl group.

"Aralkyl" means alkyl group substituted with one or more aryl groups, the meanings of aryl and alkyl are defined in this section. For example, 2,2-diphenylethyl- or phenethyl- are aralkyl groups.

"Aralkylamino" means aryl-alkyl-NH-group, the meanings of aryl and alkyl are defined in this section.

"Aralkylsulfinyl" means aralkyl-SO-group, the meanings of aralkyl are defined in this section.

"Aralkylsulfonyl" means aralkyl-$SO_2$— group, the meaning of aralkyl is defined in this section.

"Aralkylthio" means aralkyl-5-group, the meanings of aralkyl are defined in this section.

"Aralkoxy" means aralkyl-O-group, the meanings of aralkyl are defined in this section. For example, benzyloxy or 1- or 2-naphthylenmethoxy are aralkyl groups.

"Aralkoxyalkyl" means aralkyl-O-alkyl-group, the meanings of aralkyl and alkyl are defined in this section. For example, benzyloxyethyl is aralkyl-O-alkyl group.

"Aralkoxycarbonyl" means aralkyl-O—C(=O)-group, the meaning of aralkyl is defined in this section. Benzyloxycarbonyl is an example of aralkoxycarbonyl group.

"Aralkoxycarbonylalkyl" means aralkyl-O—C(=O)-alkyl-group, the meanings of aralkyl and alkyl are defined in this section. Benzyloxycarbonylmethyl or benzyloxycarbonylethyl are examples of aralkoxycarbonylalkyl groups.

"Aryl" means aromatic mono- or polycyclic system with 6-10 carbon atoms. Aryl may have one or more "cyclic system substituents" of the same or different structure. Phenyl, or naphthyl, substituted phenyl, or substituted naphthyl are the representatives of aryl groups. Aryl could be annelated with nonaromatic cyclic system or heterocycle.

"Arylcarbamoyl" means aryl-NHC(O)-group, the meaning of aryl is defined in this section.

"Aryloxy" means aryl-O-group, the meaning of aryl is defined in this section. Phenoxy- and 2-naphthyloxy are the representatives of aryloxy groups.

"Aryloxycarbonyl" means aryl-O—C(=O)-group, the meaning of aryl is defined in this section. Phenoxycarbonyl and 2-naphthoxycarbonyl are the representatives of aryloxycarbonyl groups.

"Arylsulfinyl" means aryl-SO-group, the meaning of aryl is defined in this section.

"Arylsulfonyl" means aryl-$SO_2$-group, the meaning of aryl is defined in this section.

"Arylthio" means aryl-S-group, the meaning of aryl is defined in this section. Phenylthio- and 2-naphthylthio- are the representatives of arylthio groups.

"Aroylamino" means aroyl-NH-group, the meaning of aroyl is defined in this section.

"Aroyl" means aryl-C(=O)-group, the meaning of aryl is defined in this section. Benzoyl-, 1- and 2-naphthoyl- are the representatives of aroyl groups.

"Aromatic" radical means a radical derived at removal of hydrogen atom from aromatic C—H bond. "Aromatic" radical implies aryl and heteroaryl cycles the meaning of which are defined in this section. Aryl and heteroaryl cycles may additionally contain substituents, such as aliphatic and aromatic radicals the meaning of which are defined in this section. Aryl, annelated cycloalkenylaryl, annelated cycloalkylaryl, annelated heterocyclylaryl, annelated heterocyclenyl aryl, heteroaryl, annelated cycloalkylheteroaryl, annelated cycloalkenylheteroaryl, annelated heterocyclenylheteroaryl and annelated heterocyclylheteroaryl are the representatives of aromatic radicals.

"Aromatic cycle" means a plane cyclic system in which all the atoms take part in the formation of a common conjugation system comprising, according to Hückel rule, (4n+2) π-electrons (n is a whole nonnegative number). Benzene, naphthalene, anthracene and others are the representatives of aromatic cycles. In the case of "heteroaromatic cycles" π-electrons and p-electrons of heteroatoms participate in the conjugation, so that their total number is equal to (4n+2). Pyridine, thiophene, pyrrole, furan, thiazole and others are the representatives of such cycles. Aromatic cycle may have one or more "cycle system substituents" or could be annelated to nonaromatic cycle, heteroaromatic or heterocyclic system.

"Acyl" means H—C(=O)—, alkyl-C(=O)—, cycloalkyl-C(=O), heterocyclyl-C(=O)—, heterocyclyl-alkyl-C(=O)—, aryl-C(=O)—, arylalkyl-C(=O)—, heteroaryl-C(=O)—, heteroarylalkyl-C(=O)— groups in which alkyl-, cycloalkyl-, heterocyclyl-, heterocyclylalkyl-, aryl-, arylalkyl-, heteroaryl-, heteroarylalkyl are defined in this section.

"Acylamino" means acyl-NH-group, the meaning of acyl is defined in this section.

"Bifunctional reagent" means a chemical compound with two reaction centers, both of them taking part in the reactions simultaneously or consecutively. For example, reagents containing carboxy and aldehyde or carboxy and keto groups are bifunctional reagents such as 2-formylbenzoic acid, 2-(2- oxo-ethylcarbamoyl)-benzoic acid, 2-(3-formylthiophen-2-yl)-benzoic acid or 2-(2-formylphenyl)-thiophene-3-carboxylic acid.

"1,2-vinyl radical" means —CH=CH-group with one or more "alkyl substituents" of the same or different structure the meaning of which are defined in this section.

"Halogen" means fluorine, chlorine, bromine and iodine. Preference is given to fluorine, chlorine and bromine.

"Heteroannelated cycle" means that the cycle attached (annelated or condensed) to another cycle or polycycle contains at least one heteroatom.

"Heteroaralkenyl" means heteroaryl-alkenyl-group, heteroaryl and alkenyl are defined in this section. Preferably, heteroarylalkenyl contains the lower alkenyl group. 4-Pyridylvinyl, thienylethenyl, imidazolylethenyl, pyrazinylethenyl are the representatives of heteroarylalkenyl radical.

"Heteroaralkyl" means heteroaryl-alkyl-group, heteroaryl and alkyl are defined in this section. Pyridylmethyl, thienylmethyl, furylmethyl, imidazolylmethyl, pyrazinylmethyl are the representatives of heteroaralkyl radicals.

"Heteroaralkyloxy" means heteroarylalkyl-O-group, the meaning of heteroarylalkyl is defined in this section 4-Pyridilmethyloxy-, 2-thienylmethyloxy are the representatives of heteroaralkyloxy groups.

"Heteroaryl" means aromatic mono- or polycyclic system with 5-14 carbon atoms, preferably from 5 to 10 in which one or more carbon atoms are substituted by one or more heteroatoms such as N, S or O. Prefix "aza", "oxa" or "thia" before "heteroaryl" means that atoms N, O or S are introduced in the appropriate cyclic fragment. N-Atom of heteroaryl cycle could be oxidized to N-oxide. Heteroaryl may have one or more "cyclic system substituents" of the same or different structure. Pyrrolyl, furanyl, thienyl, pyridyl, pyrazinyl, pyrimidinyl, isooxazolyl, isothiazolyl, tetrazolyl, oxazolyl, thiazolyl, pyrazolyl, furazanyl, thriazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothiazenyl, quinolinyl, imidazolyl, thienopyridyl, quinazolinyl, thienopyrimidinyl, pyrrolopyridinyl, imidazopyridinyl, isoquinolinyl, benzoazaindolyl, 1,2,4-triazinyl, thienopyrrolyl, furopyrrolyl and others are the representatives of heteroaryl radicals.

"Heteroarylsulfonylcarbamoyl" means heteroaryl-SO$_2$—NH—C(=O)-group in which heteroaryl is defined in this section.

"Heterocyclenyl" means nonaromatic mono- or polycycle system including from 3 to 13 carbon atoms, preferably from 5 to 13 carbon atoms in which one or more carbon atoms are replaced by heteroatom such as N, O or S and which contains at least one —C=C— or —C=N-double bond. Prefix "aza", "oxa" or "thia" before "heterocyclenyl" means that atoms N, O or S are present in the appropriate cyclic fragment. Heterocyclenyl may have one or more "cyclic system substituents" of the same or different structure. N- and S-atoms belonging to heterocyclenyl fragment could be oxidized to N-oxide, S-oxide and S-dioxide. 1,2,3,4-Tetrahydropyridinyl, 1,2-dihydropyridinyl, 1,4-dihydropyridinyl, 2-pyrrolinyl, 3-pyrrolinyl, dihydrofuranyl, dihydrothiophenyl and others are examples of heterocyclenyl.

"Heteroaroyl" means heteroaryl-C(=O)— group, heteroaryl is defined in this section. The representatives of heteroaroyl are nicotinoyl, thienoyl, pyrazoloyl and others.

"Heterocyclenyl" means nonaromatic monocyclic or polycyclic system including from 3 to 13 carbon atoms, preferably from 5 to 13 carbon atoms in which one or more carbon atoms are substituted with heteroatom such as N, O or S and which contains at least one —C=C— or —C=N-double bond.

Prefix "aza", "oxa" or "thia" before "heterocyclenyl" means that atoms N, O or S are present in the appropriate cyclic fragment. Heterocyclenyl may have one or more "cyclic system substituents" of the same or different structure. N- and S-atoms belonging to heterocyclenyl fragment could be oxidized to N-oxide, S-oxide and S-dioxide. 1,2,3,4-Tetrahydropyridinyl, 1,2-dihydropyridinyl, 1,4-dihydropyridinyl, 2-pyrrolinyl, 3-pyrrolinyl, dihydrofuranyl, dihydrothiophenyl and others are examples of heterocyclenyl.

"Heterocyclyl" means nonaromatic saturated mono- or polycyclic system with 3-10 carbon atoms preferably from 5 to 6 carbon atoms in which one or more carbon atoms are substituted by heteroatom such as N, O or S. Prefix "aza", "oxa" or "thia" before "heterocyclyl" means that atoms N, O or S are introduced in the appropriate cyclic fragment. Heterocyclyl may have one or more "cyclic system substituents" of the same or different structure. N- and S-atoms belonging to heterocyclyl fragment could be oxidized to N-oxide, S-oxide and S-dioxide. Piperidyl, pyrrolidinyl, piperazinyl, morpholinyl, thiomorpholinyl, thiazolidinyl, 1,4-dioxanyl, tetrahydrofuranyl, tetrahydrothiophenyl and others are examples of heterocyclyl.

"Heterocyclyloxy" means heterocyclyl-O-group, heterocyclyl is defined in this section.

"Hydrate" means stoichiometric or nonstoichiometric compositions of the compounds or their salts with water.

"Hydroxyalkyl" means HO-alkyl-group, alkyl is defined in this section.

"Depression" means big depression; the incidental, chronic and recurring form of the big depression; dysthymic disorder (dysthymia); cyclotymias; affective disorder; a syndrome of seasonal affective disorder; bipolar disorder, including bipolar disorders of I and II type; and also other depressive disorders and conditions. Depression also means the depressions accompanying Alzheimer's disease, a vascular dementia; disorder of the mood induced by alcohol and substances; schizoaffective disorder of depressive type; disorder of adaptation. Except for that, depression includes a depression of oncologic patients; a depression at Parkinson's disease; depressions after a myocardial infarction; depressions of fruitless women; pediatric depression; postnatal depression; the depressions accompanying somatic, neuralgic and other diseases.

"Substituent" means a chemical radical attached to the scaffold, for example, "alkyl group substituent" (or substituent of alkyl group), "amino group substituent" (or substituent of amino group), "carboxy group substituent", (substituent of carboxy group), "carbamoyl substituent" (substituent of carbamoyl group), "cycle system substituent" the meaning of which are defined in this section.

"Alkyl group substituent" means a substituent attached to alkyl or alkenyl group the meaning of which is defined in this section. It is selected from hydrogen, halogen, alkenyloxy, cycloalkyl, aryl, heteroaryl, heterocyclyl, aroyl, cyano, hydroxyl, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclenyl, annelated heteroarylheterocyclyl, annelated, arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k^a R_{k+1}^a N$—, $R_k^a R_{k+1}^a NC(=O)$—, $R_k^a R_{k+1}^a NSO_2$—, where $R_k^a$ and $R_{k+1}^a$ independently of each other represents hydrogen atom, alkyl, aryl, aralkyl, heteroaralkyl, heterocyclyl or heteroaryl, or $R_k^a$ and $R_{k+1}^a$ together with the N-atom which they are attached to generate through $R_k^a$ and $R_{k+1}^a$ 4-7-membered heterocyclyl or heterocyclenyl. Methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl, methoxycarbonylmethyl and pyridylmethyloxycarbonylmethyl are the preferred alkyl groups. Cycloalkyl, aryl, heteroaryl, heterocyclyl, hydroxyl, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k^a R_{k+1}^a N-$, $R_k^a R_{k+1}^a NC(=O)-$, annelated arylheterocyclenyl, annelated arylheterocyclyl are preferred "alkyl group substituents". The meanings of "alkyl group substituents" are defined in this section.

"Amino group substituent" means a substituent attached to an amino group. Amino group substituent represents hydrogen, alkyl, cycloalkyl, aryl, heteroaryl, heterocyclyl, acyl, aroyl, alkylsulfonyl, arylsulfonyl, heteroarylsulfonyl, alkylaminocarbonyl, arylaminocarbonyl, heteroarylaminocarbonyl, heterocyclylaminocarbonyl, alkylaminocarbonyl, arylaminothiocarbonyl, heteroarylaminothiocarbonyl, heterocyclylaminothiocarbonyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonylalkyl, aralkoxycarbonylalkyl, heteroaralkyloxycarbonylalkyl.

"Carbamoyl substituent" means a substituent attached to a carbamoyl group the meaning of which is defined in this section. Carbamoyl substituent could be selected from hydrogen, alkyl, cyckloalkyl, aryl, heteroaryl, heterocyclyl, alkoxycarbonylalkyl, aralkoxycarbonylalkyl, heteroaralkyloxycarbonylalkyl or $R_k^a R_{k+1}^a N-$, $R_k^a R_{k+1}^a NC(=O)$-alkyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl. Alkyl, cycloalkyl, aryl, heteroaryl, heterocyclyl, alkoxycarbonylalkyl, aralkoxycarbonylalkyl, heteroaralkyloxycarbonylalkyl or $R_k^a R_{k+1}^a N-$, $R_k^a R_{k+1}^a NC(=O)$-alkyl, annelated arylheterocyclenyl, annelated arylheterocyclyl are the preferred "carbamoyl substituents. The meanings of "carbamoyl substituents" are defined in this section.

"Nucleophilic substituent" is a chemical radical attached to the scaffold as a result of a reaction with a nucleophilic reagent, for example, one selected from a group of primary or secondary amines, alcohols, phenols, mercaptans and thiophenols.

"Cyclic system substituent" means a substituent attached to an aromatic or nonaromatic cyclic system selected from hydrogen, alkylalkenyl, alkynyl, aryl, heteroaryl, aralkyl, heteroaralkyl, hydroxyl, hydroxyalkyl, alkoxy, aryloxy, acyl, aroyl, halogen, nitro, cyano, carboxy, alkoxycarbonyl, aryloxycarbonyl, aralkoxycarbonyl, alkyloxyalkyl, aryloxyalkyl, heterocyclyloxyalkyl, arylalkyloxyalkyl, heterocyclylalkyloxyalkyl, alkylsulfonyl, arylsulfonyl, heterocyclylsulfonyl, alkylsulfinyl, arylsulfinyl, heterocyclylsulfinyl, alkylthio, arylthio, heterocyclylthio, alkylsulfonylalkyl, arylsulfonylalkyl, heterocyclylsulfonylalkyl, alkylsulfinylalkyl, arylsulfinylalkyl, heterocyclylsulfinylalkyl, alkylthioalkyl, arylthioalkyl, heterocyclylthioalkyl, arylalkylsulfonylalkyl, heterocyclylalkylsulfonylalkyl, arylalkylthioalkyl, heterocyclylalkylthioalkyl, cycloalkyl, cycloalkenyl, heterocyclyl, heterocyclenyl, amidino, $R_k^a R_{k+1}^a N-$, $R_k^a N=$, $R_k^a R_{k+1}^a N$-alkyl-, $R_k^a R_{k+1}^a NC(=O)-$ or $R_k^a R_{k+1}^a NSO_2-$, where $R_k^a$ and $R_{k+1}^a$ independently from each other represent hydrogen, optionally substituted alkyl, optionally substituted aryl, optionally substituted aralkyl, optionally substituted heteroalkyl or $R_k^a R_{k+1}^a N$-substituent in which one of $R_k^a$ could be acyl or aroyl, while the meaning of $R_{k+1}^a$ is defined above; or "cyclic system substituents" are $R_k^a R_{k+1}^a NC(=O)-$ or $R_k^a R_{k+1}^a NSO_2-$, where $R_k^a$ and $R_{k+j}^a$ together with the N-atom which they are attached to through $R_k^a$ and $R_{k+1}^a$ form 4-7-membered heterocyclyl or hetrocyclenyl.

"Electrophilic substituent" means a chemical radical attached to the scaffold as a result of a reaction with an electrophilic reagent, for example, one selected from a group of organic acids or their derivatives (anhydrides, imidazolides, acid chlorides), organic sulfonic esters or chlorides, organic haloformates, organic isocyanates and organic isothiocyanates.

"Substituted amino group" means $R_k^a R_{k+1}^a N$-group, in which $R_k^a$ and $R_{k+1}^a$ are "amino group substituents" the meanings of which are defined in this section.

"Substituted carboxyl" means C(O)OR— group. Substituted carboxyl has a substituent R, selected from alkenyl, alkyl, aryl, heteroaryl, heterocyclyl, the meanings of which are defined in this section.

"Substituted mercapto group" means SR, S(O)R or S(O2)R— group, where substituent R is selected from alkenyl, alkyl, aryl, heteroaryl, heterocyclyl, the meanings of which are defined in this section.

"Protective group" (PG) means a chemical radical attached to a scaffold or synthetic intermediate for temporary protection of amino group in multifunctional compounds, including, but not limited to: amide substituent, such as formyl, optionally substituted acetyl (for example, trichloroacetyl, trifluoroacetyl, 3-phenylpropionyl and others), optionally substituted benzoyl and others; carbamate substituent, such as optionally substituted $C_1$-$C_7$-alkoxycarbonyl, for example, methyloxycarbonyl, ethyloxycarbonyl, tert-butyloxycarbonyl, 9-fluorenylmethyloxycarbonyl (Fmoc) and others; optionally substituted $C_1$-$C_7$-alkyl substituent, for example, tert-butyl, benzyl, 2,4-dimethoxybenzyl, 9-phenylfluorenyl and others; sulfonyl substituent, for example, benzenesulfonyl, p-toluenesulfonyl and others. More specifically "Protective groups" are described in the book: Protective groups in organic synthesis, Third Edition, Green, T. W. and Wuts, P. G. M. 1999, p. 494-653. Jon Wiley & Sons, Inc., New York, Chichester, Weinheim, Brisbane, Toronto, Singapore.

"Protected primary or secondary amine" means a group of the general formula $R_k^a R_{k+1}^a N-$, where $R_k^a$ represents a protective group PG and $R_{k+1}^a$ is hydrogen, "amino group substituent", the meaning of which is defined in this section, for example, alkyl, alkenyl, aryl, aralkyl, annelated arylcycloalkenyl, annelated arylcycloalkyl, annelated arylheterocyclenyl, annelated arylheterocyclyl, cycloalkyl, cyckloalkenyl, heteroaralkyl, heteroaryl, annelated heteroarylcycloalkenyl, annelated heteroarylcycloalkyl, annelated heteroarylheterocyclenyl, annelated heteroarylheterocyclyl, heterocyclenyl or heterocyclyl.

"Imino group" means $R_k^a N=$ group substituted or not by an "amino group substituent" $R_k^a$, the meaning of which is defined in this section, for example, imino (HN=), methylimino (CH$_3$N=), ethylimino (C$_2$H$_5$N=), benzylimino (PhCH$_2$N=) or phenethylimino (PhCH$_2$CH$_2$N=).

"Inert substituent" ("non-interfering substituent") means a low- or non-reactive radical, including, but not limited to: $C_1$-$C_7$ alkyl, $C_2$-$C_7$ alkenyl, $C_2$-$C_7$ alkynyl, $C_1$-$C_7$ alkoxy, $C_7$-$C_{12}$ aralkyl, substituted with inert substituents aralkyl, $C_7$-$C_{12}$ heterocyclylalkyl, substituted with inert substituents heterocyclylalkyl, $C_7$-$C_{12}$ alkaryl, $C_3$-$C_{10}$ cycloalkyl, $C_3$-$C_{10}$ cycloalkenyl, phenyl, substituted phenyl, toluoyl, xylenyl, biphenyl, $C_2$-$C_{12}$ alkoxyalkyl, $C_2$-$C_{10}$ alkylsulfinyl, $C_2$-$C_{10}$ alkylsulfonyl, $(CH_2)_m$—O—$(C_1$-$C_7$ alkyl), —$(CH_2)_m$—N$(C_1$-$C_7$ alkyl)$_n$, aryl; aryl substituted by halogen or inert substituent; alkoxy group substituted by inert substituent; fluoroalkyl, aryloxyalkyl, heterocyclyl; heterocyclyl substituted by inert substituents and nitroalkyl; where m and n are varied from 1 to 7. The preferred inert substituents are $C_1$-$C_7$ Alkyl, $C_2$-$C_7$ alkenyl, $C_2$-$C_7$ alkynyl, $C_1$-$C_7$ alkoxy, $C_7$-$C_{12}$ aralkyl, $C_7$-$C_{12}$ alkaryl, $C_3$-$C_{10}$ cycloalkyl, $C_3$-$C_{10}$ cycloalkenyl, $C_1$-$C_7$ alkyl substituted by inert substituents, phenyl; phenyl substituted by inert substituents; $(CH_2)_m$—O—$(C_1$-$C_7$ alkyl), —$(CH_2)_m$—N(C)—$C_7$ alkyl)$_n$, aryl; aryl substituted by inert substituents, heterocyclyl and heterocyclyl substituted by inert substituents.

"Carbamoyl" means $C(=O)NR_k^a R_{k+1}^a$— group. Carbamoyl may have one or more "carbamoyl substituents" $R_k^a$ and $R_{k+1}^a$ of the same or different structure, selected from hydrogen, alkyl, alkenyl, aryl, heteroaryl, heterocyclyl, the meanings of which are defined in this section.

"Carbamoylazaheterocycle" means azaheterocycle with at least one carbamoyl group as a "cyclic system substituent". The meanings of "azaheterocycle", "cyclic system substituent", and "carbamoyl group" are defined in this section.

"Carboxy" means $HOC(=O)$— (carboxy) group.

"Carboxyalkyl" means $HOC(=O)$-alkyl group, the meaning of alkyl is defined in this section.

"Carbocycle" means monocyclic or polycyclic system consisting of carbon atoms only. Carbocycles could be both aromatic and alicyclic. Alicyclic polycycles may have one or more common atoms. One common atom leads to spirocarbocycles (for example, spiro[2,2]pentane); two—various condensed system (for example, decaline); three common atoms—to bridged systems (for example, bicycle[3,3,1]nonane); the greater number of common atoms leads to various polyhedron systems (for example, adamantane). Alicycles could be "saturated", for instance, cyclohexane, or "partly saturated"—tetraline.

"Cognitive disorders" or disorders of cognitive functions" mean disorder (weakness) of mental abilities including attentiveness, memory, cogitation, cognition, education, verbal, mental, executive and creative abilities, time and space orientation; in particular, cognitive disorders associated with Alzheimer's disease, Parkinson's and Huntington's diseases, senile dementia; age-associated memory impairment, AAMI; dysmetabolic encephalopathy; psychogenous memory impairment; amnesia; amnesic disturbances; transit global amnesia; dissociative amnesia; vascular dementia; light or mild cognitive impairment, MCI; attention deficit hyperactivity disorder (AD/HD); cognitive impairments, accompanying psychotic diseases, epilepsy, delirium, autism, psychosis, Down's syndrome, bipolar disorders and depression; AIDS-associated dementia; dementias at hypothyroidism; dementia connected with alcohol, substances causing dependability and neurotoxins; dementia accompanying neurodegenerative diseases, for example, cerebellar degeneracy and amyotrophic lateral sclerosis; cognitive disturbances connected with cerebral crisis, infectious and oncologic brain diseases as well as traumatic brain injury; cognitive functions damages associated with autoimmune and endocrine diseases, and others.

"Combinatorial library" means a collection of compounds prepared by parallel synthesis and intended for searching a hit or leader compound, and for optimization of physiological activity of the hit or leader as well, moreover each compound of the library corresponds to the common scaffold, in this way the library is a collection of related homologues or analogues.

"Medicament"—is a compound (or a mixture of compounds in the form of pharmaceutical composition) in the form of tablets, capsules, injections, ointments and other ready forms intended for restoration, improvement or modification of physiological functions at humans and animals, and for treatment and prophylaxis of diseases, diagnostics, anesthesia, contraception, cosmetology and others.

"Ligands" (from latin ligo) represent chemical compounds (small molecule, peptide, protein, inorganic ion and others), capable to interact with receptors which convert this interaction into specific signal.

"Methylene radical" means —$CH_2$-group with one or two "alkyl substituents" of the same or different structure, the meanings of which are defined in this section.

"Nonaromatic cycle" (saturated or partly saturated cycle) means nonaromatic monocyclic or polycyclic system formally generated as a result of complete or partial hydrogenization of unsaturated —C=C— or —C=N— bonds. Nonaromatic cycle may have one or more "cyclic system substituents" and could be annelated to aromatic, heteroaromatic or heterocyclic systems. Cyclohexane and piperidine are examples of nonaromatic cycles; cyclohexene and piperidine—are partly saturated cycles.

"Neurodegenerative diseases" means specific conditions and diseases, accompanied by damage and primary destruction of nervous cells populations in the certain areas of the central nervous system. Neuro-degenerative diseases include but are not limited by: Alzheimer's disease; Parkinson disease; Huntington's disease (chorea); multiocular sclerosis; cerebella degeneracy; amyotrophic lateral sclerosis; dementias with Lewy bodies; spinal muscular atrophy; peripheric neuropathy; spongy encephalitis (Creutzfeld-Jakob Disease); AIDS dementia; multi-infract dementia; frontotemporal dementias; leukoencephalopathy (spongy degeneration of white matter); chronic neurodegenerative diseases; cerebral crisis; ischemic, reperfusion and hypoxic brain damage; epilepsy; cerebral ischemia; glaucoma; traumatic brain injury; Down's syndrome; encephalomyelitis; meningitis; encephalitis; neuroblastoma; schizophrenia; depression. Moreover, neurodegenerative diseases include pathological states and disorders connected with hypoxia, substance abuse, causing dependability, under neurotoxins influence; infectious and oncologic brain diseases as well as neuronal damages associated with autoimmune and endocrine diseases and others.

"Non-natural aminoacid" means an aminoacid of not nucleinic origin. D-isomers of natural α-aminoacids, amino-butyric acid, 2-amino-butyric acid, γ-amino-butyric acid, N-α-alkyl aminoacids, 2,2-dialkyl-α-aminoacids, 1-aminocycloalkylcarboxylic acids, β-alanine, 2-alkyl-β-alanines, 2-cycloalkyl-β-alanines, 2-aryl-β-alanines, 2-heteroaryl-β-alanines, 2-heterocyclyl-β-alanines and (1-aminocycloalkyl)-acetic acids are the representatives of non natural aminoacids, the meanings of alkyl, cycloalkyl, aryl, heteroaryl and heterocyclyl are defined in this section.

"Optionally aromatic cycle" means a cycle which could be both aromatic and nonaromatic, the meanings of which are defined in this section.

"Optionally substituted radical" means a radical without or with one or more substituents.

"Optionally annelated (condensed) cycle" means a condensed or noncondensed cycle, the meanings of which are defined in this section.

"Lower alkyl" means a straight or branched alkyl radical with 1-4 carbon atoms.

"Nootrops" or "Nootropics" or neurometabolic stimulators are the substances accepted for improvement of mental ability.

"Parallel synthesis" means a method for carrying out a chemical synthesis of combinatorial library of individual compounds.

"1,3-Propylene radical" means —CH$_2$—CH$_2$—CH$_2$-group with one or more "alkyl substituents" of the same or different structure, the meanings of which are defined in this section.

"Psychotic disorders" are diseases or diseased conditions associated with mental disturbance and/or mentality frustration. Psychotic disorders include affective disorders (bipolar affective disorders, big depression, hypomania, minor depression, maniacal syndrome, Cotard's syndrome, cyclothymia, schizoid-affective disorders and so on), intellectual-mnestic disorders; manias (hypomania, graphomania, cleptomania, compulsive shopping, mania of persecution, pornographomania, erotomania and so on); disorder of multiple personality, amentia, alcoholomania, deliration, delirium syndrome, hallucinosis, hallucinations, lucinatory effects, homicidomania, delirium; illusion, clinical lycanthropy; macropsia, antagonistic delusion, micropsia, narcomania; anorexia nervosa, oneiroid syndrome, paranoid, paranoia, paraphrenia, pseudo hallucinations, psychosis, Cotard's syndrome, schizoaffective disorder, shhizotypical disorder, schizophrenia, schizoid affective psychosis disorder, schizophrenomorphic disorder, Shrebera's syndrome, Daniel Paul's syndrome), phobias (agoraphobia, arachnophobia, auto phobia, vermin phobia, hydrosophobia, hydrophobia, demo phobia, zoophobia, carcinophobia, claustrophobia, climacophobia, xenophobia, misophobia, radio phobia, photophobia; skoliephobia, zoophobia, social phobia, tetra phobia, triskaidekaphobia, erotophobia); alcoholic psychosis, alcoholic palimpsest, allotriophagy, aphasia, graphomania, dissociative fugue state, dissociate disorders; dysphorias, internet-dependences, hypochondria, hysteria, kop phobia, delirium of persecution, melancholy, misanthropy, obsession, panic attacks, Asperger's syndrome, Capgras' syndrome, Munchausen's syndrome, Retta's syndrome, Fregoly's syndrome, syndrome of attention and hyperactivity deficit, obsessive-compulsive disorder, syndrome of chronic narcotization consequences, syndrome of psychic automatism, syndrome of infantile autism, madness, taphophilia, anxiety conditions, Hikikomory's syndrome, erotographomania and so on.

"Leader compound" (leader) means a compound of outstanding (maximum) physiological activity associated with a concrete biotarget related to a definite (or several) pathology or disease.

"Hit compound" (hit) means a compound demonstrated the desired physiological activity during the primary screening process.

"Sulfamoyl group" means $R_k^a R_{k+1}^a NSO_2$-group substituted or not by "amino group substituents" $R_k^a$ and $R_{k+1}^a$, the meanings of which are defined in this section.

"Sulfonyl" means R—SO$_2$-group in which R is selected from alkyl, cycloalkyl, aryl, heteroaryl, heterocyclyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, the meanings of which are defined in this section.

"Template" means the common structural fragment of the group of the compounds or compounds forming the combinatorial library.

"Therapeutic cocktail" is a simultaneously administered combination of two or more drug substances with different mechanism of pharmacological action and aimed at different biotargets taking part in pathogenesis of the disease.

"Thiocarbamoyl" means $R_k^a R_{k+1}^a NC(=S)$-group. Thiocarbamoyl may have one or more "amino group substituents" $R_k^a$ and $R_{k+1}^a$, selected from alkyl, alkenyl, aryl, heteroaryl and heterocyclyl the meanings of which are defined in this section.

"Anxiety disorders" means generalized (inconcrete) anxiety; acute uncontrolled anxiety; panic disorder; phobia, for example, agoraphobia (acute fear of crowded place) or social (acute fear of humiliation at presence of other people) or any other phobia (acute fear of particular subjects, animals or situations, in the form of phobia of height, of medical procedures, lifts, open space etc.); an obsession condition (obsessive-compulsive disorder); posttraumatic stress disorder and acute stress disorder. Besides, anxiety disorders include anxiety conditions induced by alcohol or substances; anxiety under adaptation; as well as mixed forms of anxiety disorders and depression.

"Cycloalkyl" means nonaromatic monocyclic or polycyclic system with 3-10 carbon atoms. Cycloalkyl may have one or more "cyclic system substituents" of the same or different structure. The representatives of cycloalkyl groups are cyclopropyl, cyclobutyl, cyclopentyl, cyclohexyl, decalinyl, norbornyl, adamant-1-yl and others. Cycloalkyl could be annelated with aromatic cycle or heterocycle. Alkyl, aralkoxy, hydroxy or $R_k^a R_{k+1}^a N$— are preferred "cyclic system substituents", the meanings of which are defined in this section.

"Cycloalkylcarbonyl" means cycloalkyl-C(=O)-group, the meaning of cycloalkyl is defined in this section. The representatives of cycloalkylcarbonyl groups are cyclopropylcarbonyl and cyclohexylcarbonyl.

"Cycloalkoxy" means cycloalkyl-O-group, the meaning of cycloalkyl is defined in this section.

"Pharmaceutical composition" means a composition including the compound of formula I and, at least, one of the components selected from pharmaceutically acceptable and pharmacologically compatible excipients, solvents, diluents, carriers, auxiliary distributing and perceiving means, means acting as a vehicle, such as preserving agents, stabilizers, excipients, grinders, wetting agents, emulsifying and suspending agents, thickeners, sweeteners, flavouring agents, antibacterial agents, fungicidal agent, lubricants, regulators of the prolonged delivery, the choice and suitable proportions of which depends on the nature and the way of administration and dosage. Ethoxylated isostearyl alcohol, polyoxyethelene, sorbitol and sorbitol ether, microcrystalline cellulose, aluminum metahydroxide, bentonite, agar-agar and tragacant and the mixtures thereof as well are examples of suitable suspending agents. Protection against action of microorganisms can be provided by means of various antibacterial and antifungal agents, for example, parabens, chlorobutanole, sorbic acid, and similar compounds. A composition may include also isotonic agents, such as: sugars, sodium chloride and the same. The prolonged action of the composition can be provided by means of agents slowing down the absorption of active ingredient, for example, aluminum monostearate and gelatin. Suitable carriers, solvents, diluents and vehicle agents include water, ethanol, polyalcohols and their mixtures, natural oils (such as olive oil) and organic esters for injection (such as ethyl oleate). Suitable fillers include lactose, milk-sugar, sodium citrate, calcium carbonate, calcium phosphate and similar to them. Starch, alginic acid and its salts, silicates are examples of grinders and distributing means. Suitable lubricants include magnesium stearate, sodium lauryl sulfate, talc and polyethylene glycol with high molecular weight. Pharmaceutical composition which contains active ingredient one or in combination with other active compound could be used for oral, sublingual, transdermal, intramuscular, intravenous, subcutaneous, local or rectal introduction for humans and animals in a standard form as a mixture with traditional pharmaceutical carries. Suitable standard forms of administration include oral forms of introduction such as tablets, gelatin capsules, pills, powders, granules, chewing-gums and peroral solutions or suspensions; for examples, therapeutic cocktail, sublingual and transbuccal forms of introduction; aerosols; implantants; local, transdermal, subcutaneous, intramuscular, intravenous, intranasal or intraocular forms of introduction and rectal forms of introductions.

"Pharmaceutically acceptable salt" means relatively nontoxic both organic and inorganic salts of acids and bases disclosed in this invention. The salts could be prepared in situ in the processes of synthesis, isolation or purification of compounds or they could be prepared directly. In particular, bases' salts could be prepared starting from purified base of the disclosed compound and suitable organic or mineral acid. Such salts could be obtained with the following acids: hydrochloric acid, hydrobromic acid, sulfuric acid, nitric acid, phosphoric acid, acetic acid, succinic acid, valeric acid, oleic acid, palmitic acid, stearic acid, lauric acid, boric acid, benzoic acid, lactic acid, p-toluenesulfonic acid, citric acid, maleic acid, fumaric acid, succinic acid, tartaric acid, methanesulphonic acid, malonic acid, salicylic acid, propionic acid, ethanesulphonic acid, benzenesulfonic acid, sulfamic acid and the like (Detailed description of properties of such salts is given in: Berge S. M., et al., "Pharmaceutical Salts" J. Pharm. Sci., 1977, 66: 1-19). Salts of the disclosed acids could be also prepared by the reaction of purified acids with suitable bases; moreover, metal salts and amine salts could be synthesized too. To metal salts could be referred salts of sodium, potassium, calcium, barium, magnesium, lithium and aluminum salts; the preferred salts are those of sodium and potassium. Inorganic bases suitable for metal salts preparation include sodium hydroxide, carbonate, bicarbonate, hydride; potassium hydroxide, carbonate and bicarbonate, lithium hydroxide, calcium hydroxide, magnesium hydroxide, zinc hydroxide. As organic bases suitable for preparation of the disclosed acid salts amines and amino acids with the basicity high enough to make up stable; pharmaceutically acceptable and nontoxic salts could be used. Ammonia, methylamine, dimethylamine, trimethylamine, ethylamine, diethylamine, triethylamine, benzylamine, dibenzylamine, dicyclohexyl amine, piperazine, ethylpiperidine, tris(hydroxymethyl)-aminomethane and the like could be referred to such amines. Besides that, some tetraalkylammonium hydroxides such as holine, tetramethylammonium, tetraethylammonium and the like could be used for salts formation. Lysine, ornithine and agrinine are useful as aminoacids with high basicity.

"Focused library" is a combinatorial library or a combination of several combinatorial libraries, or a combination of libraries and compounds arranged in a special way to enhance the probability of finding hits and leaders or to improve the efficiency of their optimization. The design of focused libraries is, as a rule, associated with the directed search for effectors (inhibitors, activators, agonists, antagonists and so on) of definite biotargets (enzymes, receptors, ion channels and so on).

"Fragment" (scaffold) means a molecular frame typical for the group of compounds or compounds belonging to the combinatorial library.

"1,2-Ethylene radical" means —CH$_2$—CH$_2$-group containing one or more "alkyl substituents" of the same or different structure, the meanings of which are defined in this section.

The invention relates to novel antagonists of serotonin 5-HT$_6$ receptors that simultaneously regulate homeostasis of Ca$^{+2}$ ions in the cells.

The object of the invention is achieved by antagonists of serotonin 5-HT$_6$ receptors which are substituted 2,3,4,5-tetrahydro-1H-pyrido[4,3-b]indoles of the general formula 1, pharmaceutically acceptable salts and/or hydrates thereof.

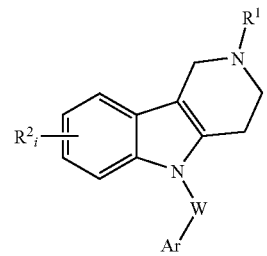

1 wherein:

R$^1$ is selected from optionally substituted C$_1$-C$_5$ alkyl;

R$^2_i$ represents one or more equal or different substituents selected from hydrogen, halogen, C$_1$-C$_3$ alkyl, CF$_3$, OCF$_3$ or OCH$_3$;

Ar represents unsubstituted phenyl or phenyl substituted with halogen, C$_1$-C$_6$ alkyl, C$_1$-C$_6$ alkoxy, optionally modified amino group or CF$_3$; or optionally substituted 6-membered aromatic heterocycle containing 1 or 2 nitrogen atom in the cycle;

W represents ethylene group —CH$_2$—CH$_2$—, ethenyl group —CH=CH— or ethynyl group —C≡C—.

The preferred antagonists are antagonists representing substituted 5-ethenyl-2,3,4,5-tetrahydro-1H-pyrido[4,3-b]indoles of the general formula 1.1

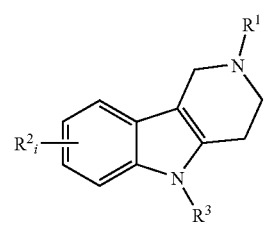

1.1 wherein:

R$^1$ and R$^2_i$ are all as defined above;

R$^3$ represents —CH=CH—Ar group, wherein Ar has the meanings mentioned above.

The preferred antagonists are substituted cis-5-ethenyl-2,3,4,5-tetrahydro-1H-pyrido[4,3-b]indoles of the general formulas 1.1.1, 1.1.2 and substituted trans-5-ethenyl-2,3,4,5-tetrahydro-1H-pyrido[4,3-b]indoles of the general formulas 1.1.3, 1.1.4.

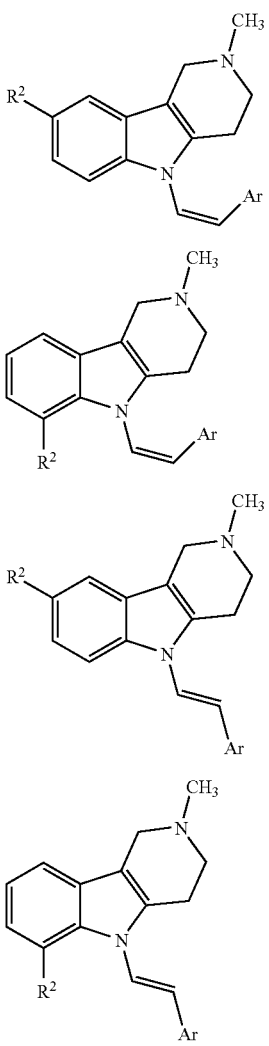

wherein:

R² represents H, F, CH₃, CF₃, OCF₃ or OCH₃;

Ar has the meanings mentioned above.

The preferred antagonists of the general formula 1.1 are selected from the group consisting of cis-2-methyl-5-styryl-2,3,4,5-tetrahydro-1H-pyrido[4,3-b]indole 1.1(1), trans-2-methyl-5-styryl-2,3,4,5-tetrahydro-1H-pyrido[4,3-b]indole 1.1(2), trans-2-methyl-5-[2-(pyridin-4-yl)vinyl]-2,3,4,5-tetrahydro-1H-pyrido[4,3-b] indole 1.1(3), cis-2-methyl-5-[2-(pyridin-3-yl)vinyl]-2,3,4,5-tetrahydro-1H-pyrido[4,3-b]indole 1.1(4), trans-2-methyl-5-[2-(pyridin-2-yl)vinyl]-2,3,4,5-tetrahydro-1H-pyrido[4,3-b]indole 1.1(5), cis-2-tert-butyl-5-[2-(pyridin-3-yl)vinyl]-2,3,4,5-tetrahydro-1H-pyrido[4,3-b]indole 1.1(6), cis-2-methyl-5-styryl-8-fluoro-2,3,4,5-tetrahydro-1H-pyrido[4,3-b]indole 1.1.1(1), trans-2-methyl-5-styryl-8-fluoro-2,3,4,5-tetrahydro-1H-pyrido[4,3-b]indole 1.1.3(1), trans-2-methyl-5-[2-(pyridin-4-yl)vinyl]-8-fluoro-2,3,4,5-tetrahydro-1H-pyrido[4,3-b]indole 1.1.3(2), cis-2-methyl-5-[2-(pyridin-3-yl)vinyl]-8-fluoro-2,3,4,5-tetrahydro-1H-pyrido[4,3-b]indole 1.1.1(2), trans-2-methyl-5-[2-(pyridin-2-yl)vinyl]-8-fluoro-2,3,4,5-tetrahydro-1H-pyrido[4,3-b]indole 1.1.3(3), cis-2,8-dimethyl-5-styryl-2,3,4,5-tetrahydro-1H-pyrido[4,3-b]indole 1.1.1(3), trans-2,8-dimethyl-5-styryl-2,3,4,5-tetrahydro-1H-pyrido[4,3-b]indole 1.1.3(4), cis-2,8-dimethyl-5-[2-(pyridin-3-yl)vinyl]-2,3,4,5-tetrahydro-1H-pyrido[4,3-b]indole 1.1.1(4), trans-2,8-dimethyl-5-[2-(pyridin-4-yl)vinyl]-2,3,4,5-tetrahydro-1H-pyrido[4,3-b]indole 1.1.3(5), cis-2-benzyl-8-methyl-5-[2-(pyridin-3-yl)vinyl]-2,3,4,5-tetrahydro-1H-pyrido[4,3-b]indole 1.1.1(5), trans-2-methyl-5-(4-fluorostyryl)-8-fluoro-2,3,4,5-tetrahydro-1H-pyrido[4,3-b]indole 1.1.3(6), cis-2-methyl-5-(3-fluorostyryl)-8-fluoro-2,3,4,5-tetrahydro-1H-pyrido[4,3-b]indole 1.1.1(6), trans-2,8-dimethyl-5-[4-(trifluoromethyl)styryl]-2,3,4,5-tetrahydro-1H-pyrido[4,3-b]indole 1.13(7), cis-2,8-dimethyl-5-[3-(trifluoromethyl)styryl)]-2,3,4,5-tetrahydro-1H-pyrido[4,3-b]indole 1.1.1(7), trans-2-methyl-5-[4-(trifluoromethyl)styryl]-8-fluoro-2,3,4,5-tetrahydro-1H-pyrido[4,3-b]indole 1.1.3(8), cis-2-methyl-5-(4-methoxystyryl)-8-fluoro-2,3,4,5-tetrahydro-1H-pyrido[4,3-b]indole 1.1.1(8), cis-2-methyl-5-[4-(dimethylamino)styryl]-8-fluoro-2,3,4,5-tetrahydro-1H-pyrido[4,3-b]indole 1.1.1(9) or trans-2,8-dimethyl-5-(4-fluorostyryl)-2,3,4,5-tetrahydro-1H-pyrido[4,3-b]indole 1.1.3(9) corresponding to the formulas shown below or pharmaceutically acceptable salts thereof.

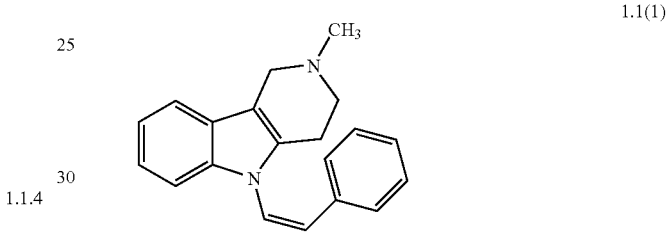

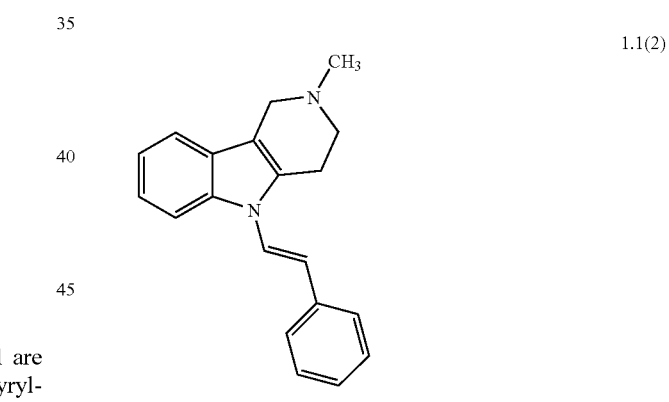

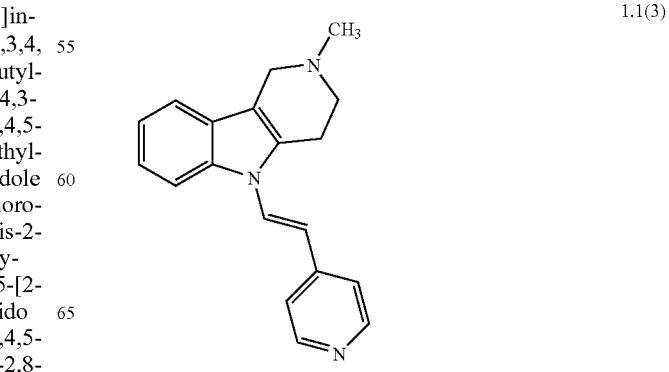

-continued
1.1(4)
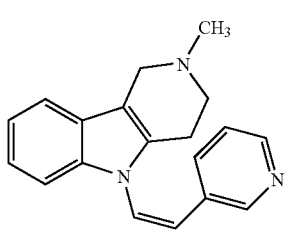
1.1(5)
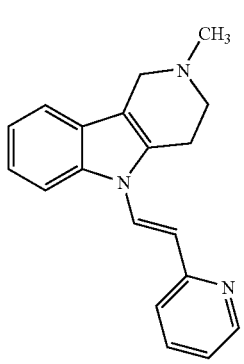
1.1(6)
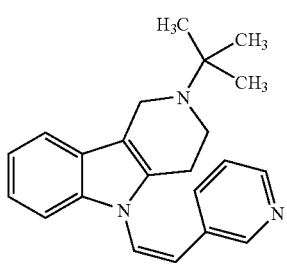
1.1.1(1)
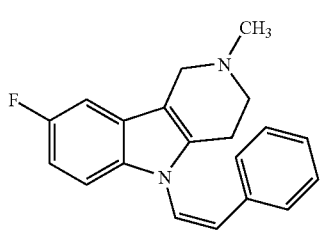
1.1.3(1)
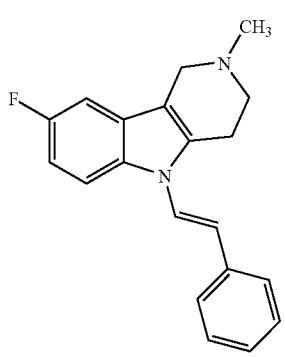
-continued
1.1.3(2)
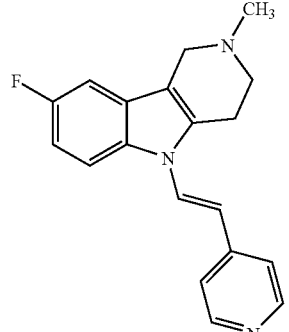
1.1.1(2)
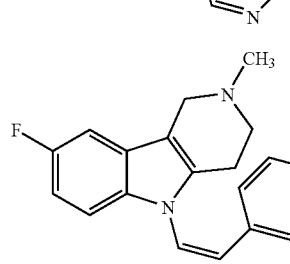
1.1.3(3)
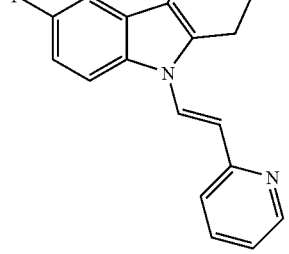
1.1.1(3)
1.1.3(4)

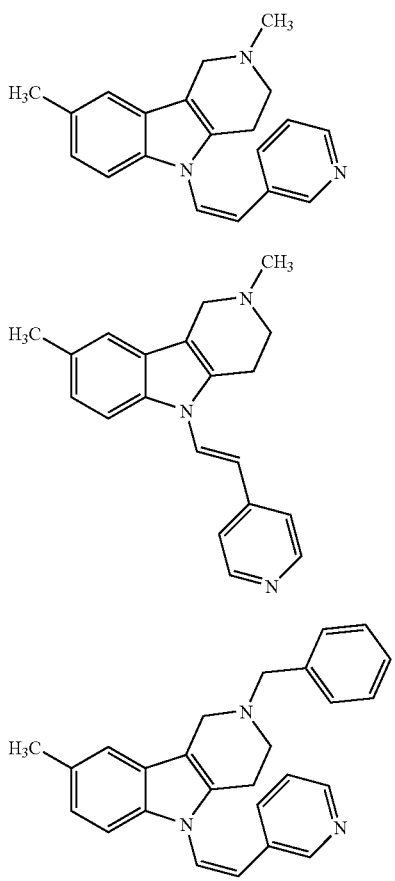
1.1.1(4)
1.1.3(5)
1.1.1(5)
1.1.3(6)
1.1.1(6)
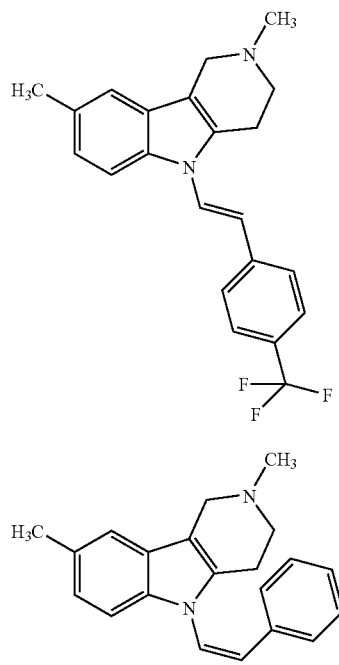
1.1.3(7)
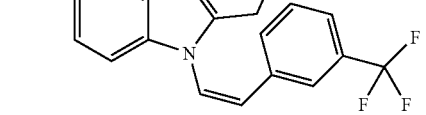
1.1.1(7)
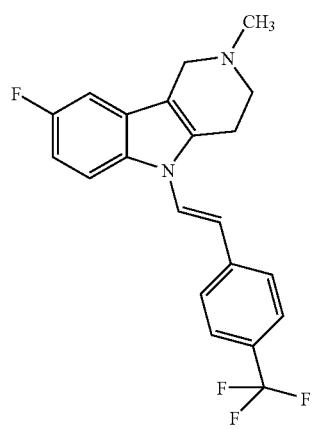
1.1.3(8)
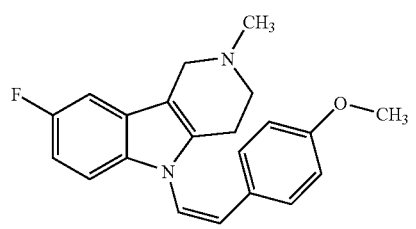
1.1.1(8)
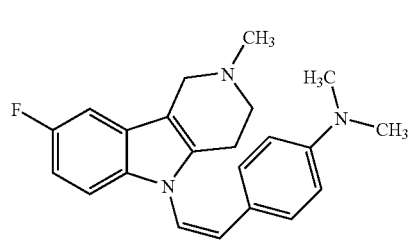
1.1.1(9)

1.1.3(9)

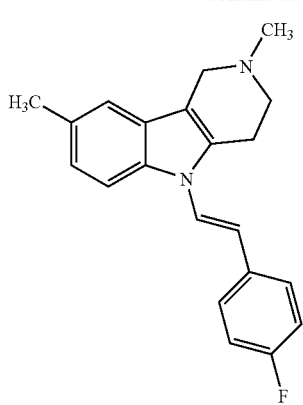

The preferred antagonists are substituted 5-ethyl-2,3,4,5-tetrahydro-1H-pyrido[4,3-b]indoles of the general formula 1.2

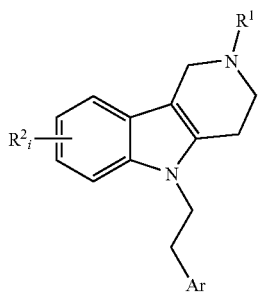

1.2 wherein:
R$^1$, R$^2_i$ and Ar are all as defined above.
The preferred antagonists are substituted 5-ethyl-2,3,4,5-tetrahydro-1H-pyrido[4,3-b]indoles of the general formulas 1.2.1, 1.2.2

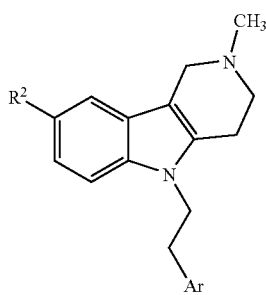

1.2.1

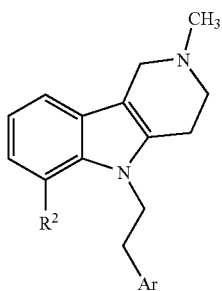

1.2.2 wherein:
R$^2$ represents H, F, CH$_3$, OCF$_3$ or OCH$_3$;
Ar has the meanings mentioned above.

The preferred antagonists of the general formula 1.2 are selected from the group consisting of 2-methyl-5-(2-phenethyl)-2,3,4,5-tetrahydro-1H-pyrido[4,3-b]indole 1.2(1), 2-methyl-5-[2-(pyridin-4-yl)ethyl]-2,3,4,5-tetrahydro-1H-pyrido[4,3-b] indole 1.2(2), 2-methyl-5-[2-(pyridin-3-yl)ethyl]-2,3,4,5-tetrahydro-1H-pyrido[4,3-b]indole 1.2(3), 2-methyl-5-[2-(pyridin-2-yl)ethyl]-2,3,4,5-tetrahydro-1H-pyrido[4,3-b]indole 1.2(4), 2-tert-butyl-5-[2-(pyridin-3-yl)ethyl]-2,3,4,5-tetrahydro-1H-pyrido[4,3-b]indole 1.2(5), 2-methyl-5-[2-(6-methylpyridin-3-yl)ethyl]-2,3,4,5-tetrahydro-1H-pyrido[4,3-b]indole 1.2(6), 2,8-dimethyl-5-(2-phenethyl)-2,3,4,5-tetrahydro-1H-pyrido[4,3-b]indole 1.2.1(1), 2,8-dim ethyl-5-[2-(pyridin-4-yl)ethyl]-2,3,4,5-tetrahydro-1H-pyrido[4,3-b]indole 1.2.1(2), 2,8-dimethyl-5-[2-(pyridin-3-yl)ethyl]-2,3,4,5-tetrahydro-1H-pyrido[4,3-b]indole 1.2.1(3), 2,8-dimethyl-5-[2-(pyridin-2-yl)ethyl]-2,3,4,5-tetrahydro-1H-pyrido[4,3-b]indole 1.2.1(4), 2,8-dimethyl-5-[2-(6-methylpyridin-3-yl)ethyl]-2,3,4,5-tetrahydro-1H-pyrido[4,3-b]indole 1.2.1(5), 2,8-dimethyl-5-[2-(pyrazin-2-yl)ethyl]-2,3,4,5-tetrahydro-1H-pyrido[4,3-b]indole 1.2.1(6), 2-methyl-5-(2-phenethyl)-8-fluoro-2,3,4,5-tetrahydro-1H-pyrido[4,3-b]indole 1.2.1(7), 2-methyl-5-[2-(pyridin-4-yl)ethyl]-8-fluoro-2,3,4,5-tetrahydro-1H-pyrido[4,3-b]indole 1.2.1(8), 2-methyl-5-[2-(pyridin-3-yl)ethyl]-8-fluoro-2,3,4,5-tetrahydro-1H-pyrido[4,3-b]indole 1.2.1(9), 2-methyl-5-[2-(pyridin-2-yl)ethyl]-8-fluoro-2,3,4,5-tetrahydro-1H-pyrido[4,3-b]indole 1.2.1(10), 2-methyl-5-[2-(6-methylpyridin-3-yl)ethyl]-8-fluoro-2,3,4,5-tetrahydro-1H-pyrido[4,3-b]indole 1.2.1(11), 2-methyl-5-(2-phenethyl)-8-(trifluoromethyl)-2,3,4,5-tetrahydro-1H-pyrido[4,3-b]indole 1.2.1(12), 2-methyl-5-[2-(pyridin-3-yl)ethyl]-8-(trifluoromethyl)-2,3,4,5-tetrahydro-1H-pyrido[4,3-b]indole 1.2.1(13), 2-methyl-5-(2-phenethyl)-6-fluoro-2,3,4,5-tetrahydro-1H-pyrido[4,3-b]indole 1.2.2(1), 2-methyl-5-(2-phenethyl)-6-(trifluoromethyl)-2,3,4,5-tetrahydro-1H-pyrido[4,3-b]indole 1.2.2(2) or 2-methyl-5-[2-(pyridin-3-yl)ethyl]-6-(trifluoromethyl)-2,3,4,5-tetrahydro-1H-pyrido[4,3-b]indole 1.2.2(3) corresponding to the formulas shown below or pharmaceutically acceptable salts thereof.

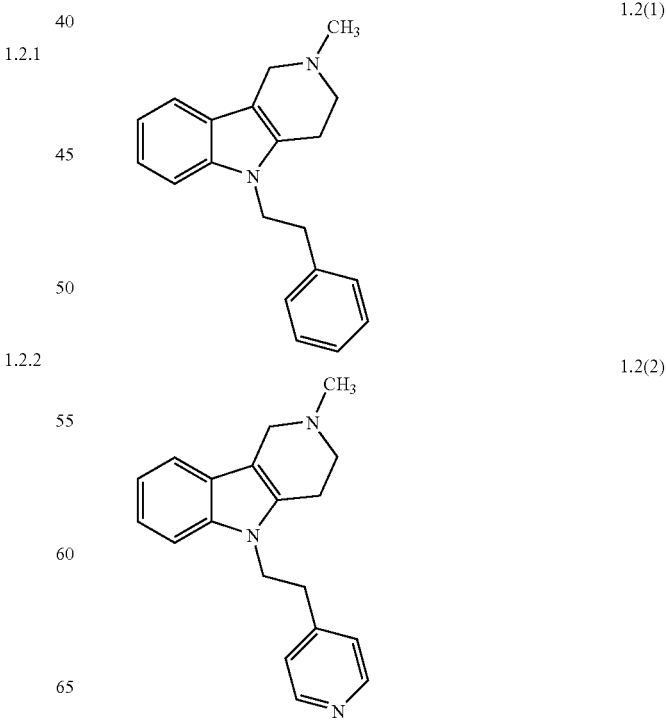

1.2(3)
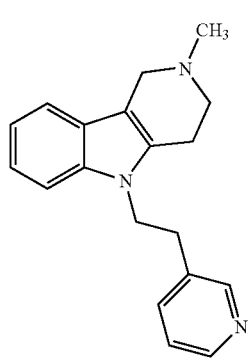
1.2(4)
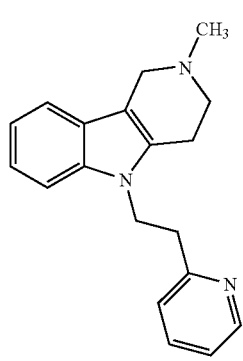
1.2(5)
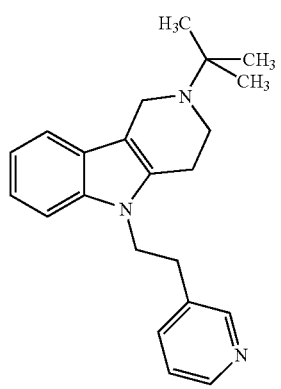
1.2(6)
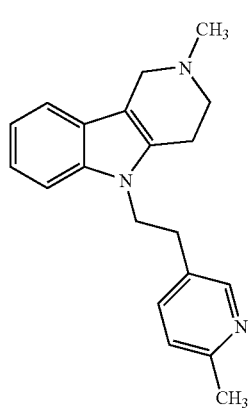
1.2.1(1)
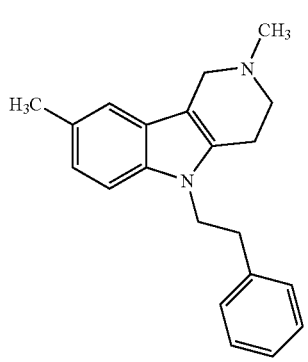
1.2.1(2)
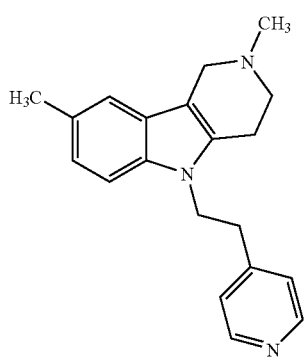
1.2.1(3)
1.2.1(4)
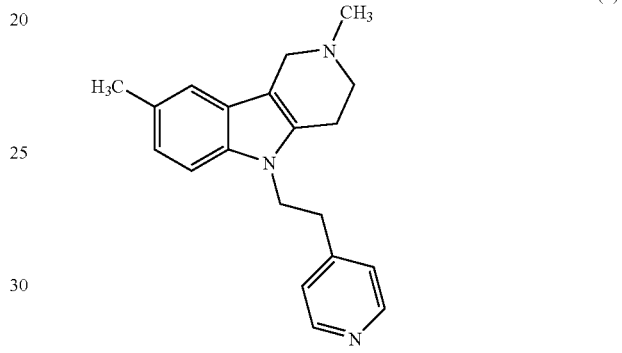

1.2.1(5)
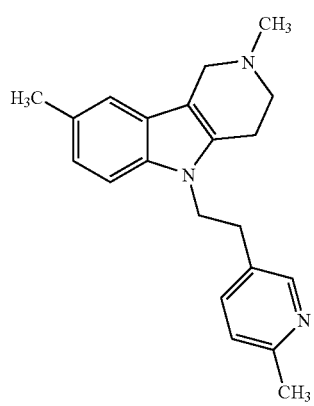
1.2.1(6)
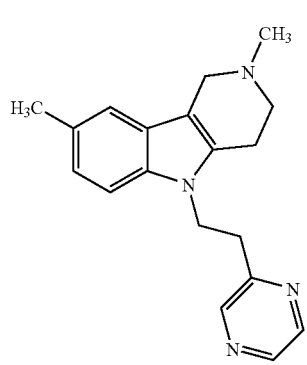
1.2.1(7)
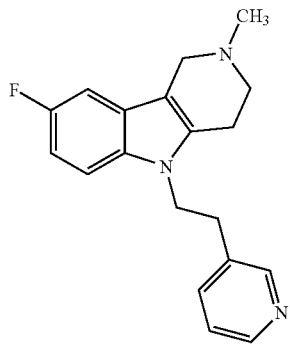
1.2.1(8)
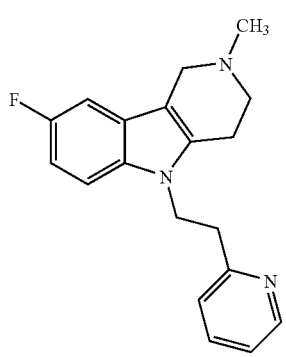
1.2.1(9)
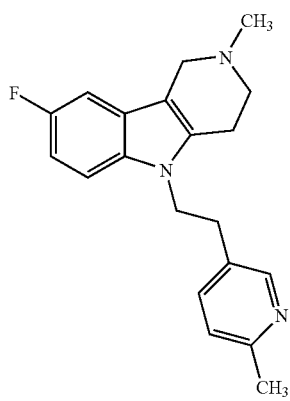
1.2.1(10)
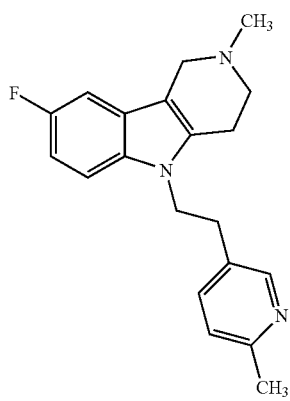
1.2.1(11)
1.2.1(12)
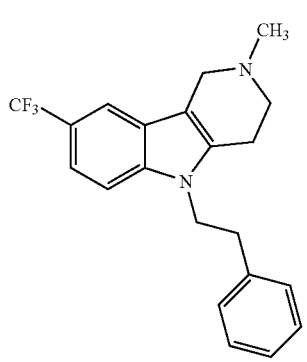

-continued 1.2.1(13)

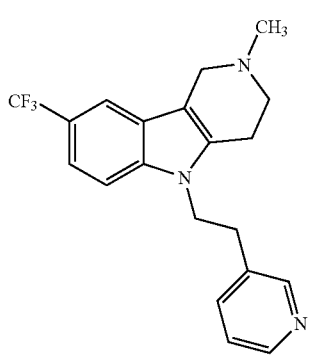

1.2.2(1)

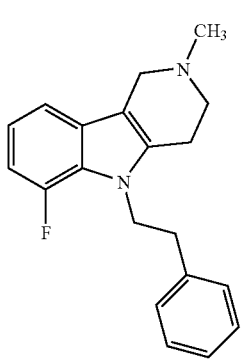

1.2.2(2)

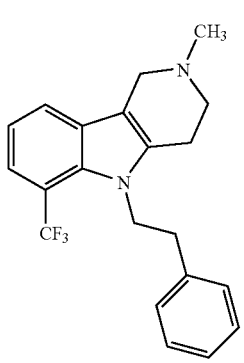

1.2.2(3)

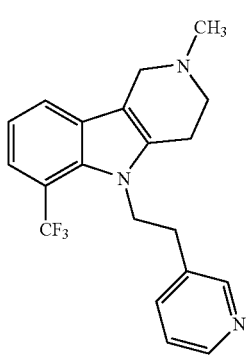

The preferred antagonists are substituted 5-ethynyl-2,3,4,5-tetrahydro-1H-pyrido[4,3-b]indoles of the general formula 1.3

1.3 wherein:
$R^1$, $R^2_i$ and Ar are all as defined above.

The preferred antagonists are substituted 5-ethynyl-2,3,4,5-tetrahydro-1H-pyrido[4,3-b]indoles of the general formulas 1.3.1, 1.3.2

1.3.1

1.3.2 wherein:
$R^2$ represents H, F, $CH_3$, $CF_3$, $OCF_3$ or $OCH_3$;
Ar has the meanings mentioned above.

The preferred antagonists of the general formula 1.3 are selected from the group consisting of 2-methyl-5-(phenylethynyl)-2,3,4,5-tetrahydro-1H-pyrido[4,3-b]indole 1.3(1), 2-methyl-5-(pyridin-2-ylethynyl)-2,3,4,5-tetrahydro-1H-pyrido[4,3-b]indole 1.3(2), 2-methyl-5-(pyridin-3-ylethynyl)-2,3,4,5-tetrahydro-1H-pyrido[4,3-b]indole 1.3(3), 2-methyl-5-(pyridin-4-ylethynyl)-2,3,4,5-tetrahydro-1H-pyrido[4,3-b]indole 1.3(4), 2-methyl-5-(pyrimidin-5-ylethynyl)-2,3,4,5-tetrahydro-1H-pyrido[4,3-b]indole 1.3(5), 2-methyl-5-(phenylethynyl)-8-fluoro-2,3,4,5-tetrahydro-1H-pyrido[4,3-b]indole 1.3.1(1), 2-methyl-5-(pyridin-2-ylethynyl)-8-fluoro-2,3,4,5-tetrahydro-1H-pyrido[4,3-b]indole 1.3.1(2), 2-methyl-5-(pyridin-3-ylethynyl)-8-fluoro-2,3,4,5-tetrahydro-1H-pyrido[4,3-b]indole 1.3.1(3), 2-methyl-5-(pyridin-4-ylethynyl)-8-fluoro-2,3,4,5-tetrahydro-1H-pyrido[4,3-b]indole 13.1(4), 2-methyl-5-(pyridin-3-ylethynyl)-6-fluoro-2,3,4,5-tetrahydro-1H-pyrido[4,3-b]indole 13.2(1), 2,8-dimethyl-5-(phenylethynyl)-2,3,4,5-tetrahydro-1H-pyrido[4,3-b]indole 1.3.1(5), 2,8-dimethyl-5-(pyridin-2-ylethynyl)-2,3,4,5-tetrahydro-1H-pyrido[4,3-b]indole 1.3.1(6), 2,8-dimethyl-5-(pyridin-3-ylethynyl)-2,3,4,5-tetrahydro-1H-pyrido[4,3-b]indole 1.3.1(7), 2,8-dimethyl-5-(pyridin-4-ylethynyl)-2,3,4,5-tetrahydro-1H-pyrido[4,3-b]indole 1.3.1(8), 2-methyl-5-(pyridin-3-ylethynyl)-8-(trifluoromethyl)-2,3,4,5-tetrahydro-1H-pyrido[4,3-b]indole 1.3.1(9), 2-methyl-5-[(4-methoxyphenyl)ethynyl]-8-fluoro-2,3,4,5-tetrahydro-1H-pyrido[4,3-b]indole 13.1(10), 2-methyl-51(4-fluorophenyl)ethynyl]-8-fluoro-2,3,4,5-tetrahydro-1H-pyrido[4,3-b]indole 1.3.1(11), 2-methyl-5-[(3-fluorophenyl)ethynyl]-8-fluoro-2,3,4,5-tetrahydro-1H-pyrido[4,3-b]indole 1.3.1(12), 2-methyl-5-[((4-trifluoromethyl)phenyl)ethynyl]-8-fluoro-2,3,4,5-tetrahydro-1H-pyrido[4,3-b]indole 1.3.1(13), 2-methyl-5-(pyridin-3-ylethynyl)-8-(trifluoromethyl)-2,3,4,5-tetrahydro-1H-pyrido[4,3-b]indole 1.3.1(14), 2,8-dimethyl-5-[(4-fluorophenyl)ethynyl]-2,3,4,5-tetrahydro-1H-pyrido[4,3-b]indole 1.3.1(15), 2,8-dimethyl-5-[(3-fluorophenyl)ethynyl]-2,3,4,5-tetrahydro-1H-pyrido[4,3-b]indole 1.3.1(16), 2,8-dimethyl-5-[((4-trifluoromethyl)phenyl)ethynyl]-2,3,4,5-tetrahydro-1H-pyrido[4,3-b]indole 1.3.1(17), 2,8-dimethyl-5-[((3-trifluoromethyl)phenyl)ethynyl]-2,3,4,5-tetrahydro-1H-pyrido[4,3-b]indole 1.3.1(18), 2,8-dimethyl-5-[((2-trifluoromethyl)phenyl)ethynyl]-2,3,4,5-tetrahydro-1H-pyrido[4,3-b]indole 1.3.1(19), 2,8-dimethyl-5-[(2-fluorophenyl)ethynyl]-2,3,4,5-tetrahydro-1H-pyrido[4,3-b]indole 1.3.1(20), 2,8-dimethyl-5-[(4-methoxyphenyl)ethynyl]-2,3,4,5-tetrahydro-1H-pyrido[4,3-b]indole 1.3.1(21), 2,8-dimethyl-5-[((4-dimethylamino)phenyl)ethynyl]-2,3,4,5-tetrahydro-1H-pyrido[4,3-b]indole 1.3.1(22), 2,8-dimethyl-5-[(3-methoxyphenyl)ethynyl]-2,3,4,5-tetrahydro-1H-pyrido[4,3-b]indole 1.3.1(23) or 2,8-dimethyl-5-[(2-methoxyphenyl)ethynyl]-2,3,4,5-tetrahydro-1H-pyrido[4,3-b]indole 1.3.1(24) corresponding to the formulas shown below or pharmaceutically acceptable salts thereof.

1.3(1)

1.3(2)

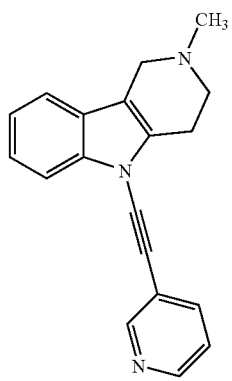

1.3(3)

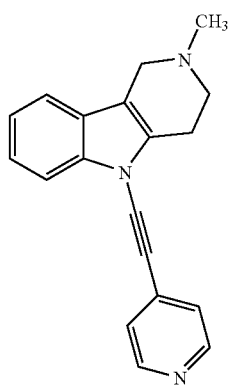

1.3(4)

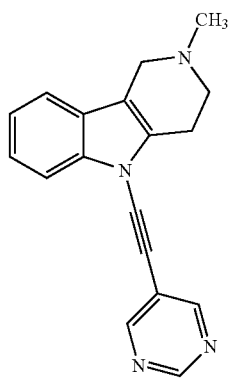

1.3(5)

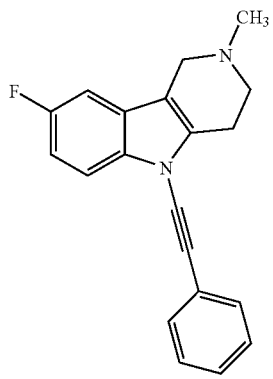

1.3.1(1)

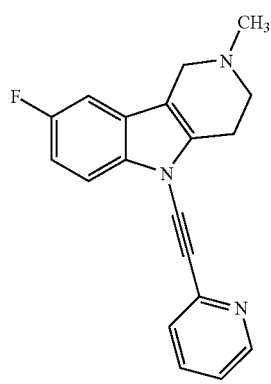
1.3.1(2)
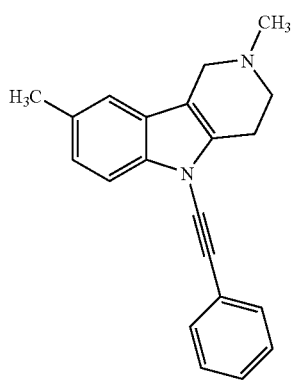
1.3.1(5)
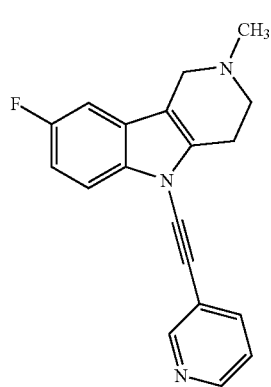
1.3.1(3)
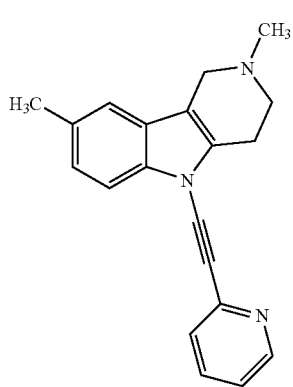
1.3.1(6)
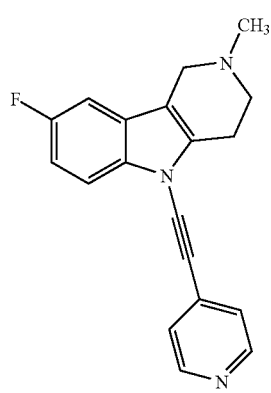
1.3.1(4)
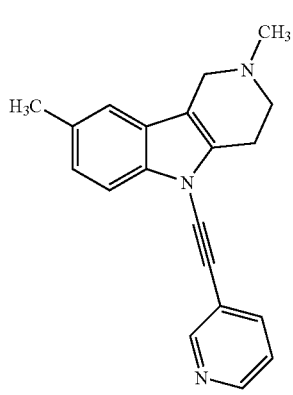
1.3.1(7)
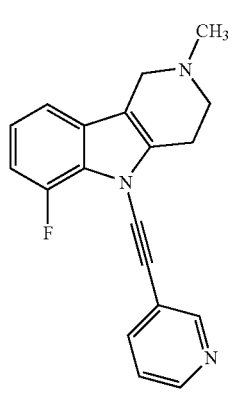
1.3.2(1)
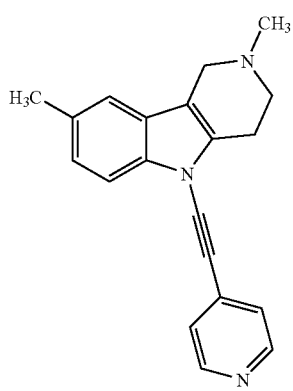
1.3.1(8)

-continued
1.3.1(9)
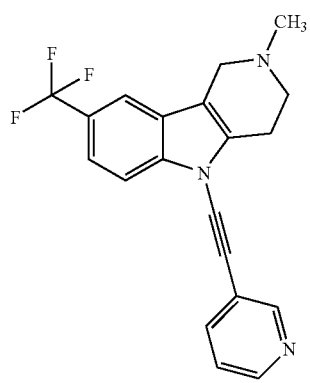
1.3.1(10)
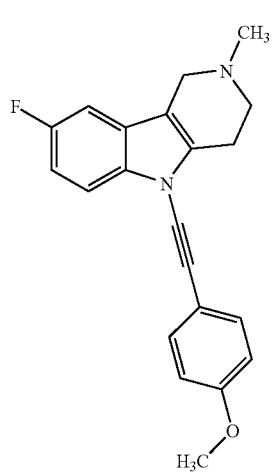
1.3.1(11)
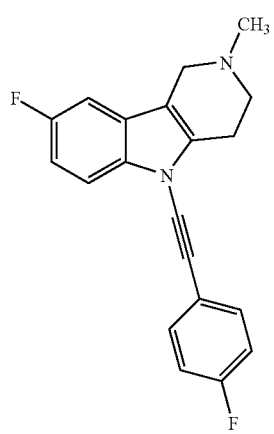
1.3.1(12)
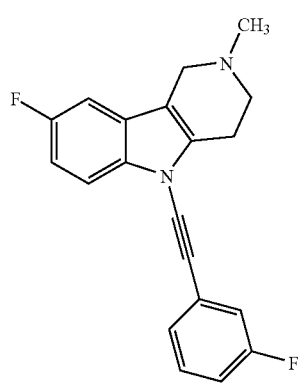
-continued
1.3.1(13)
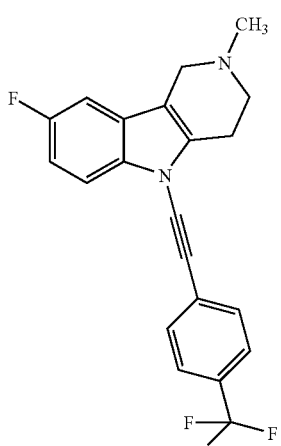
1.3.1(14)
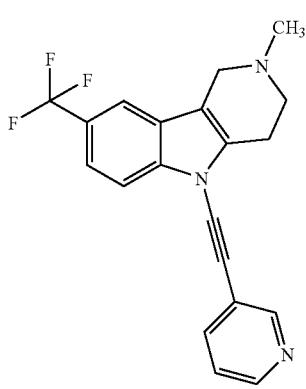
1.3.1(15)
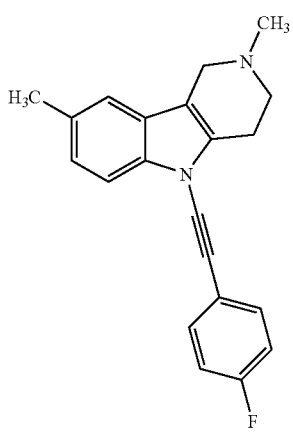
1.3.1(16)
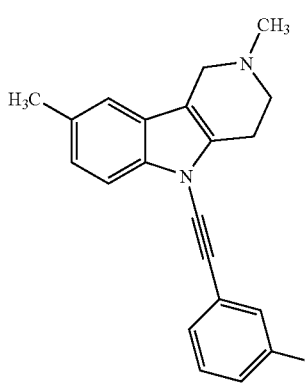

1.3.1(17)
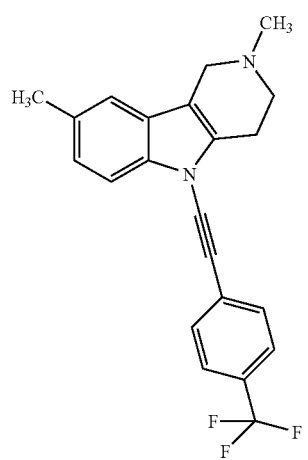
1.3.1(18)
1.3.1(19)
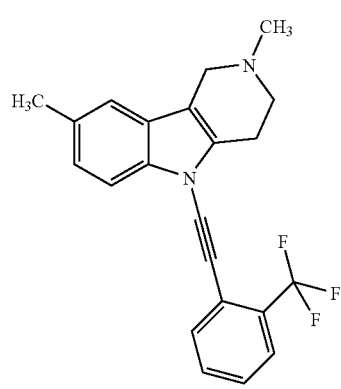
1.3.1(20)
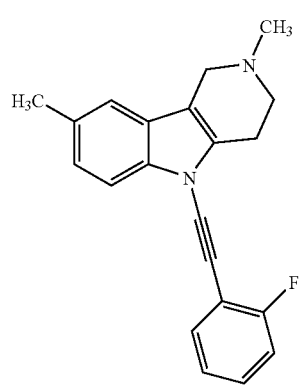
1.3.1(21)
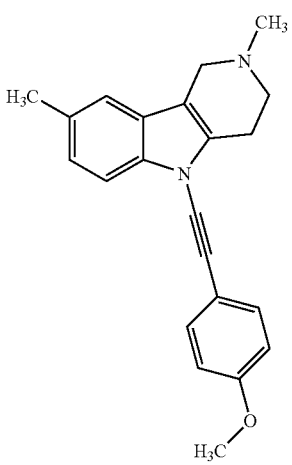
1.3.1(22)
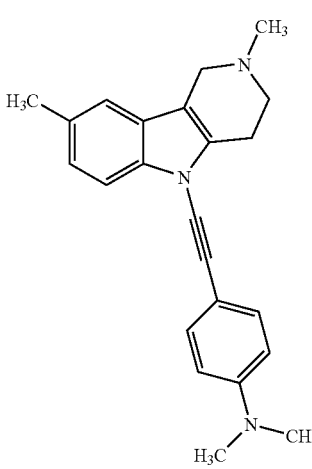
1.3.1(23)
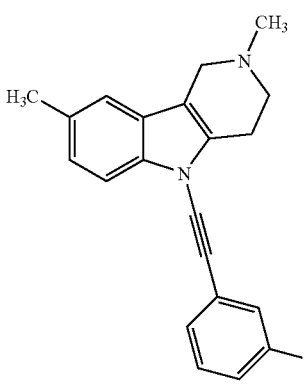

1.3.1(24)

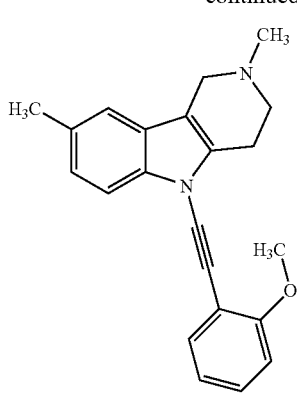

The purpose of the present invention is a new pharmaceutical composition, exhibiting properties of antagonist of 5-$HT_6$ receptors and simultaneously modulating $Ca^{+2}$ ions homeostasis in cells for preparation of various drug formulations.

The object in view is achieved by the pharmaceutical composition comprising as an active ingredient an effective amount of at least one antagonist of 5-$HT_6$ receptors selected from substituted 2,3,4,5-tetrahydro-1H-pyrido[4,3-b]indoles of the general formula 1 or pharmaceutically acceptable salt and/or hydrate thereof.

The preferable pharmaceutical composition is the composition comprising as an active ingredient at least one substituted 5-[2-aryl(or azaheterocyclyl)ethenyl]-2,3,4,5-tetrahydro-1H-pyrido[4,3-b]indole of the general formula 1.1.

The preferable pharmaceutical composition is the composition comprising as an active ingredient at least one substituted 5-[2-aryl(or azaheterocyclyl)ethyl]-2,3,4,5-tetrahydro-1H-pyrido[4,3-b]indole of the general formula 1.2.

The preferable pharmaceutical composition is the composition comprising as an active ingredient at least one substituted 5-[2-aryl(or azaheterocyclyl)ethynyl]-2,3,4,5-tetrahydro-1H-pyrido[4,3-b]indole of the general formula 1.3.

Pharmaceutical compositions may include pharmaceutically acceptable excipients. Pharmaceutically acceptable excipients mean diluents, auxiliary agents and/or carriers applied in the sphere of pharmaceutics. According to the invention the pharmaceutical composition together with substituted 2,3,4,5-tetrahydro-1H-pyrido[4,3-b]indoles of the general formula 1 may include other active ingredients provided that they do not cause undesirable effects. If required, according to the present invention, pharmaceutical compositions can be used in clinical practice in various formulations prepared by mixing the compositions with traditional pharmaceutical carries, for example, peroral forms (such as, tablets, gelatinous capsules, pills, solutions or suspensions); forms for injections (such as, solutions or suspensions for injections, or a dry powder for injections which requires only addition of water for injections before usage); local forms (such as, ointments or solutions).

The carriers used in pharmaceutical compositions, according to the present invention, include carriers which are applied in the sphere of pharmaceutics for preparation of the commonly used formulations including: binding agents, greasing agents, disintegrators, solvents, diluents, stabilizers, suspending agents, colorless agents, taste flavors are used for peroral forms; antiseptic agents, solubilizers, stabilizers are used in forms for injections; base materials, diluents, greasing agents, antiseptic agents are used in local forms.

The purpose of the present invention is also a method for preparation of pharmaceutical compositions.

The object in view is achieved by mixing at least one active ingredient which is an antagonist of 5-$HT_6$ receptors, selected from substituted 2,3,4,5-tetrahydro-1H-pyrido[4,3-b]indoles of the general formula 1 or pharmaceutically acceptable salt and/or hydrate thereof with pharmaceutically acceptable carriers, diluents or excipients.

The subject of the invention is medicaments in the form of tablets, capsules or injections, placed in a pharmaceutically acceptable packing intended for the prophylaxis and treatment of cognitive disorders and neurodegenerative diseases, pathogenesis of which is associated with 5-$HT_6$ receptors and excessive intracellular $Ca^{+2}$ ions concentration, which comprise effective amount of an antagonist selected from substituted 2,3,4,5-tetrahydro-1H-pyrido[4,3-b]indoles of the general formula 1 or pharmaceutically acceptable salts and/or hydrates thereof, with the exception of medicaments intended for prophylaxis and treatment of Alzheimer's disease and Huntington's disease comprising 2,8-dimethyl-5-[2-(6-methylpyridin-3-yl)ethyl]-2,3,4,5-tetrahydro-1H-pyrido[4,3-b]indole of the formula 1.2.1(5)HCl.

The preferable medicaments are the medicaments in the form of tablets, capsules or injections placed in a pharmaceutically acceptable packing intended for the prophylaxis and treatment of Alzheimer's disease and Huntington's disease, which comprise an effective amount of at least one antagonist of 5-$HT_6$ receptors selected from substituted 2,3,4,5-tetrahydro-1H-pyrido[4,3-b]indoles of the general formula 1 or pharmaceutically acceptable salts and/or hydrates thereof, with the exception of medicaments intended for prophylaxis and treatment of Alzheimer's disease and Huntington's disease comprising 2,8-dimethyl-5-[2-(6-methylpyridin-3-yl) ethyl]-2,3,4,5-terahydro-1H-pyrido[4,3-b]indole of the formula 1.2.1(5)HCl.

The preferable medicaments are the medicaments comprising 2,8-dimethyl-5-(2-phenyl ethyl)-2,3-tetrahydro-1H-pyrido[4,3-b]indole 1.2.1(1) as antagonist of 5-$HT_6$ receptors.

The purpose of the present invention is also medicaments in the form of tablets, capsules or injections placed in pharmaceutically acceptable packing intended for the prophylaxis and treatment of mental disorders and schizophrenia.

The object in view is achieved by medicaments in the form of tablets, capsules or injections placed in a pharmaceutically acceptable packing intended for the prophylaxis and treatment of mental disorders and schizophrenia, which comprise an effective amount of at least one antagonist of 5-$HT_6$ receptors selected from substituted 2,3,4,5-tetrahydro-1H-pyrido [4,3-b]indoles of the general formula 1 or pharmaceutically acceptable salts and/or hydrates thereof.

The preferable medicaments are the medicaments (antidepressants) intended for the prophylaxis and treatment of depressions which comprise an effective amount of at least one 5-$HT_6$ receptors antagonist selected from substituted 2,3,4,5-tetrahydro-1H-pyrido[4,3-b]indoles of the general formula 1 or pharmaceutically acceptable salts and/or hydrates thereof.

The preferable medicaments are antidepressants comprising an effective amount of 2,8-dimethyl-5-(2-phenylethyl)-2,3,4,5-tetrahydro-1H-pyrido[4,3-b]indole 1.2.1(1) or pharmaceutically acceptable salts thereof as antagonist of 5-$HT_6$ receptors.

The preferable medicaments are the medicaments (anxiolytics or tranquilizers) intended for the prophylaxis and treatment of anxious disorders which comprise an effective amount of at least one 5-$HT_6$ receptors antagonist selected from substituted 2,3,4,5-tetrahydro-1H-pyrido[4,3-b]indoles of the general formula 1 or pharmaceutically acceptable salts and/or hydrates thereof.

The preferable medicament is the anxiolytic (tranquilizer) comprising an effective amount of 2,8-dimethyl-5-[2-(6-methylpyridin-3-yl)ethyl]-2,3,4,5-tetrahydro-1H-pyrido[4,3-b]indole 1.2.1(5) or pharmaceutically acceptable salt thereof as antagonist of $5$-$HT_6$ receptors The preferable medicament is the anxiolytic (tranquilizer) comprising an effective amount of 2,8-dimethyl-5-(2-phenylethyl)-2,3,4,5-tetrahydro-1H-pyrido[4,3-b]indole 1.2.1(1) or pharmaceutically acceptable salt thereof as antagonist of $5$-$HT_6$ receptors The preferable medicaments are the medicaments (nootropics) intended for the prophylaxis and treatment of hyperkinetic disorders, in particular, cognition enhancing, which comprise an effective amount of at least one antagonist of $5$-$HT_6$ receptors selected from substituted 2,3,4,5-tetrahydro-1H-pyrido[4,3-b]indoles of the general formula 1 or pharmaceutically acceptable salts and/or hydrates thereof.

The more preferable medicament is the nootropic comprising an effective amount of 2,8-dim ethyl-5-[2-(6-methylpyridin-3-yl)ethyl]-2,3,4,5-tetrahydro-1H-pyrido[4,3-b]indole 1.2.1(5) or pharmaceutically acceptable salt thereof as antagonist of $5$-$HT_6$ receptors.

The preferable medicament is the nootropic comprising an effective amount of 2,8-dimethyl-5-(2-phenylethyl)-2,3,4,5-tetrahydro-1H-pyrido[4,3-b]indole 1.2.1(1) or pharmaceutically acceptable salt thereof as antagonist of $5$-$HT_6$ receptors.

The purpose of the present invention is also medicaments in the form of tablets, capsules, injections placed in a pharmaceutically acceptable packing intended for the prophylaxis and treatment of obesity.

The subject of this invention is also therapeutic cocktails intended for the prophylaxis and treatment of various diseases, associated with $5$-$HT_6$ receptors and excessive intracellular concentration of $Ca^{+2}$ ions in humans and animals, which comprise medicaments in the form of tablets, capsules or injections placed in a pharmaceutically acceptable packing on the basis of pharmaceutical compositions comprising at least one substituted 2,3,4,5-tetrahydro-1H-pyrido[4,3-b]indol of the general formula 1 or its pharmaceutically acceptable salt and/or hydrate as antagonist of serotonin $5$-$HT_6$ receptors.

Another subject of the invention is therapeutic cocktails intended for the prophylaxis and treatment of various diseases, pathogenesis of which associated with the excessive intracellular concentration of $Ca^{+2}$ ions, including neurological disorders, neurodegenerative and cognitive disorders in humans and animals, among them the prophylaxis and treatment of Alzheimer's disease, Huntington's disease, psychotic disorders and schizophrenia, hypoxia, ischemia, hypoglycemia, convulsions, brain injuries, latirism, amyotrophic lateral sclerosis, obesity and stroke, which comprise medicaments in the form of tablets, capsules or injections placed in pharmaceutically acceptable packing on the basis of pharmaceutical compositions comprising at least one substituted 2,3,4,5-tetrahydro-1H-pyrido[4,3-b]indol of the general formula 1 or its pharmaceutically acceptable salt and/or hydrate as antagonist of serotonin $5$-$HT_6$ receptors.

The therapeutic cocktails intended for the prophylaxis and treatment of various diseases, pathogenesis of which is associated with the excessive intracellular concentration of $Ca^{+2}$ ions in humans and animals, including neurological disorders, neurodegenerative and cognitive disorders, among them for the prophylaxis and treatment of Alzheimer's disease, Huntington's disease, psychotic disorders and schizophrenia, hypoxia, ischemia, hypoglycemia, convulsions, brain injuries, latirism, amyotrophic lateral sclerosis and stroke along with the medicaments disclosed in the invention, may include other medicaments, such as: non-steroidal anti-inflammatory drugs (Ortofen, Indometacin, Ibuprofen, etc.), inhibitors of acetylcholinesterase (Takrin, Amiridin, Fizostigmin, Arisept, Phenserine, etc.), estrogens (e.g., Estradiol), NMDA-receptor antagonists (e.g., Memantin, Neramexane); nootropic drugs (e.g., Piracetam, Fenibut, etc.); AMRA receptor modulators (e.g., Ampalex); antagonists of cannabinoid ST-1 receptors (for example, Rimonabant); monoaminooxidase MAO-B and/or MAO-A inhibitors (e.g., Rasagiline); anti-amiloidogen drugs (e.g., Tramiprosate); substances lowering beta-amyloid neurotoxicity (e.g., Indole-3-propionic acid), inhibitors of gamma- and/or beta-Sekretaza; agonists of M1 muscarine receptors (e.g., Cevimeline); metals helatories (e.g., Clioquinol); antagonists of GAMK (B) receptors (e.g., CGP-36742); monoclonal antibodies (e.g., Bapineuzumab); antioxidants; neurotrophic agents (e.g., Tserebrolizin); antidepressants (e.g., Imipramine, Sertralin etc.) and others.

Therapeutic cocktails for reducing overweight and obesity treating along with medicaments disclosed in the invention may also include other medicaments such as: anorexic drugs (e.g., Fepranon, Dezopimon, Mazindol), hormonal drugs (e.g., Tireoidin), hypolipidemic drugs, such as fibrates (e.g. Fenofibrat), statines (e.g., Lovastatin, Simvastatin, Pravastatin and Probukol), and also hypoglycemia drugs (sulfonylureas—for example, Butamid, Glibenklamid; biguanidines—for example, Buformin, Metmorfin), and drugs with other mechanism of action, such as antagonists of cannabinoid CB-1 receptors (Rimonabant), inhibitors of norepinephrine and serotonin reuptake (Sibutramine), inhibitors of enzymes of fatty acid synthesis (Orlistat), and others, along with antioxidants, food additives, etc.

According to the invention the method for prophylaxis and treatment of various diseases and conditions associated with $5$-$HT_6$ receptors and excessive concentration of $Ca^{+2}$ ions in cells at humans and animals consists in introduction to the said mammals an effective amount of medicament in the form of tablets, capsules or injections comprising as an active ingredient at least one antagonist of $5$-$HT_6$ receptors selected from substituted 2,3,4,5-tetrahydro-1H-pyrido[4,3-b]indoles of the general formula 1, or pharmaceutically acceptable salts and/or hydrates thereof, or therapeutic cocktail including these medicaments.

The medicaments could be administered perorally or parenterally (for example, intravenously, subcutaneously, intraperitoneally or locally). The clinical dosage of the antagonists of the general formula 1 could be corrected depending on: therapeutic efficiency and bioavailability of the active ingredient in the organism, rate of their exchange and deducing from organism, and depending on the age, gender and the severity of the patient's symptoms; the daily dosage for adults falls within the range of about 10 to about 500 mg of the active ingredient, preferably of about 50 to about 300 mg. Therefore, according to the present invention during the preparation of pharmaceutical compositions as units of dosage it is necessary to keep in mind the above effective dosage, so that each unit of dosage should contain of about 10 to about 500 mg of substituted 2,3,4,5-tetrahydro-1H-pyrido[4,3-b]indole of the general formula 1, preferably 50~300 mg. In accordance with the recommendation of a physician or pharmacist the above dosage can be taken several times during the definite time intervals (preferably—from one to six times).

The purpose of the present invention is novel substituted 2,3,4,5-tetrahydro-1H-pyrido[4,3-b]indoles exhibiting biological activity.

The object in view is achieved by substituted 2,3,4,5-tetrahydro-1H-pyrido[4,3-b]indoles of the general formula 1, pharmaceutically acceptable salts and/or hydrates thereof

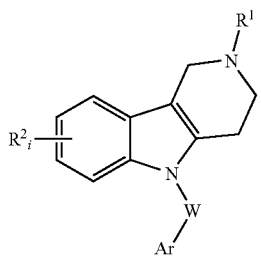

1 wherein:

$R^1$ is selected from optionally substituted $C_1$-$C_5$ alkyls;

$R^2_i$ represents one or more equal or different substituents selected from hydrogen, halogen, $C_1$-$C_3$ alkyl, $CF_3$, $OCF_3$ or $OCH_3$;

Ar represents unsubstituted phenyl or phenyl substituted with halogen, $C_1$-$C_6$ alkyl, $C_1$-$C_6$ alkoxy, optionally modified amino group or $CF_3$; or optionally substituted 6-membered aromatic heterocycle containing 1 or 2 nitrogen atom in the cycle;

W represents ethylene group —$CH_2$—$CH_2$—, ethenyl group —CH═CH— or ethynyl group —C≡C—;

with the exception of: 2-methyl-5-phenethyl-2,3,4,5-tetrahydro-1H-pyrido[4,3-b]indole, 2-methyl-5-[2-(pyridin-2-yl) ethyl)]-2,3,4,5-tetrahydro-1H-pyrido[4,3-b]indole, 2-methyl-5-[2-(pyridin-4-yl)ethyl)]-2,3,4,5-tetrahydro-1H-pyrido[4,3-b]indole, 2,8-dimethyl-5-[2-(pyridin-4-yl) ethyl)]-2,3,4,5-tetrahydro-1H-pyrido[4,3-b]indole, 2-methyl-8-(trifluoromethyl)-5-[2-(pyridin-4-yl)ethyl)]-2,3,4,5-tetrahydro-1H-pyrido[4,3-b]indole, 2-methyl-8-carboxy-5-[2-(pyridin-4-yl)ethyl)]-2,3,4,5-tetrahydro-1H-pyrido[4,3-b]indole, 2-methyl-8-ethyloxycarbonyl-5-[2-(pyridin-4-yl)ethyl)]-2,3,4,5-tetrahydro-1H-pyrido[4,3-b] indole, 2-$C_1$-$C_5$ alkyl-5-[2-(6-methylpyridin-3-yl)ethyl]-2,3,4,5-tetrahydro-1H-pyrido[4,3-b]indoles, 2-$C_1$-$C_5$ alkyl-8-methyl-5-[2-(6-methylpyridin-3-yl)ethyl]-2,3,4,5-tetrahydro-1H-pyrido[4,3-b]indoles, 2-benzyl-5-[2-(6-methylpyridin-3-yl)ethyl]-2,3,4,5-tetrahydro-1H-pyrido[4,3-b]indole, 2-benzyl-8-chloro-5-[2-(6-methylpyridin-3-yl)ethyl]-2,3,4,5-tetrahydro-1H-pyrido[4,3-b]indole, 2-benzyl-8-methyl-5-[2-(6-methylpyridin-3-yl)ethyl]-2,3,4,5-tetrahydro-1H-pyrido[4,3-b]indole, 2,7-dimethyl-5-[2-(6-methylpyridin-3-yl)ethyl]-2,3,4,5-tetrahydro-1H-pyrido[4,3-b]indole, 7-chloro-2-methyl-5-[2-(6-methylpyridin-3-yl) ethyl]-2,3,4,5-tetrahydro-1H-pyrido[4,3-b]indole, 7-(trifluoromethyl)-2-methyl-5-[2-(6-methylpyridin-3-yl) ethyl]-2,3,4,5-tetrahydro-1H-pyrido[4,3-b]indole, 2,8-dimethyl-5-[2-(6-methylpyridin-3-yl)ethyl]-2,3,4,5-tetrahydro-1H-pyrido[4,3-b]indole, 8-bromo-2-methyl-5-[2-(6-methylpyridin-3-yl)ethyl]-2,3,4,5-tetrahydro-1H-pyrido[4,3-b]indole, 8-chloro-2-methyl-5-[2-(6-methylpyridin-3-yl) ethyl]-2,3,4,5-tetrahydro-1H-pyrido[4,3-b]indole, 8-trifluoromethyl-2-methyl-5-[2-(6-methylpyridin-3-yl) ethyl]-2,3,4,5-tetrahydro-1H-pyrido[4,3-b]indole, 2,6-dimethyl-8-chloro-5-[2-(6-methylpyridin-3-yl)ethyl]-2,3,4,5-tetrahydro-1H-pyrido[4,3-b]indole, 2,7,8-trimethyl-5-[2-(6-methylpyridin-3-yl)ethyl]-2,3,4,5-tetrahydro-1H-pyrido[4,3-b]indole, 7,8-dichloro-2-methyl-5-[2-(6-methylpyridin-3-yl)ethyl]-2,3,4,5-tetrahydro-1H-pyrido[4,3-b]indole, 2,8-dimethyl-7-chloro-5-[2-(6-methylpyridin-3-yl)ethyl]-2,3,4,5-tetrahydro-1H-pyrido[4,3-b]indole, 2,7-dimethyl-8-chloro-5-[2-(6-methylpyridin-3-yl)ethyl]-2,3,4,5-tetrahydro-1H-pyrido[4,3-b]indole, 2,8,9-trimethyl-5-[2-(6-methylpyridin-3-yl)ethyl]-2,3,4,5-tetrahydro-1H-pyrido[4,3-b]indole, 2-methyl-8-chloro-5-[2-(pyridin-3-yl)ethyl]-2,3,4,5-tetrahydro-1H-pyrido[4,3-b]indole and 2-methyl-5-[2-(2-methylpyridin-3-yl)ethyl]-2,3,4,5-tetrahydro-1H-pyrido[4,3-b] in dole or pharmaceutically acceptable salts thereof.

The preferred pyrido[4,3-b]indoles are substituted 5-ethenyl-2,3,4,5-tetrahydro-1H-pyrido[4,3-b]indoles of the general formula 1.1

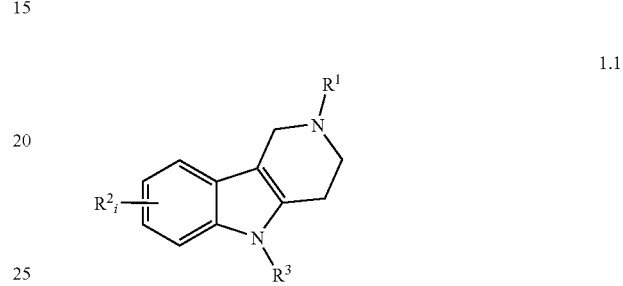

1.1 wherein:

$R^1$ and $R^2_i$ are all as defined above;

$R^3$ represents —CH═CH—Ar group, wherein Ar has the meanings mentioned above.

The preferred pyrido[4,3-b]indoles are substituted cis-5-ethenyl-2,3,4,5-tetrahydro-1H-pyrido[4,3-b]indoles of the general formulas 1.1.1, 1.1.2 and substituted trans-5-ethenyl-2,3,4,5-tetrahydro-1H-pyrido[4,3-b]indoles of the general formulas 1.1.3, 1.1.4

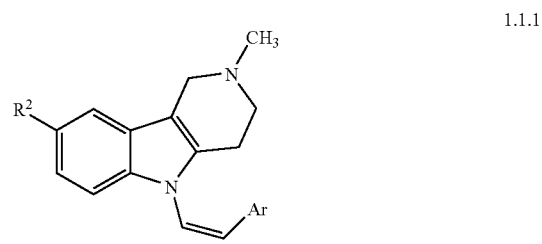

1.1.1

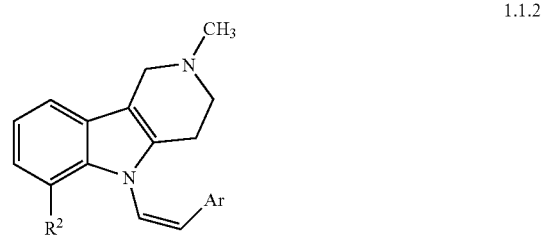

1.1.2

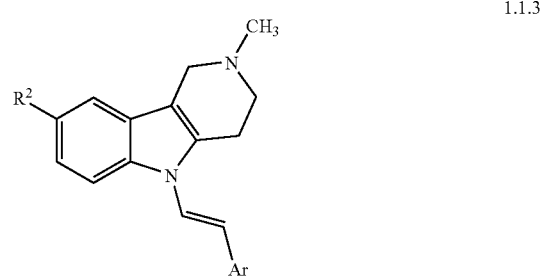

1.1.3

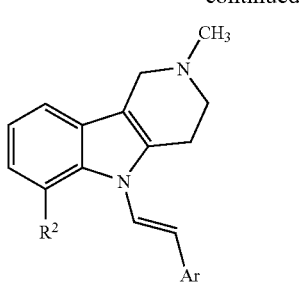

1.1.4

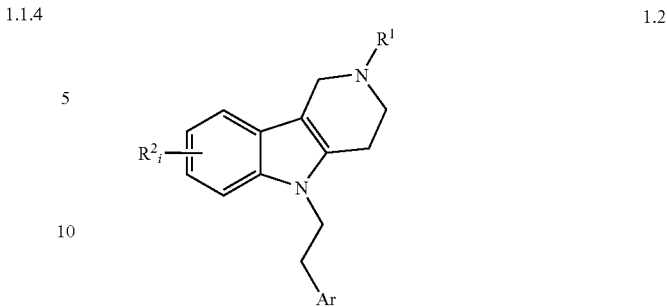

1.2 wherein:

R² represents H, F, CH₃, CF₃, OCF₃ or OCH₃;

Ar is optionally substituted phenyl, optionally substituted pyridyl.

The preferred pyrido[4,3-b]indoles of the general formula 1.1 are selected from the group consisting of cis-2-methyl-5-styryl-2,3,4,5-tetrahydro-1H-pyrido[4,3-b]indole 1.1(1), trans-2-methyl-5-styryl-2,3,4,5-tetrahydro-1H-pyrido[4,3-b]indole 1.1(2), trans-2-methyl-5-[2-(pyridin-4-yl)vinyl]-2,3,4,5-tetrahydro-1H-pyrido[4,3-b]indole 1.1(3), cis-2-methyl-5-[2-(pyridin-3-yl)vinyl]-2,3,4,5-tetrahydro-1H-pyrido[4,3-b]indole 1.1(4), trans-2-methyl-5-[2-(pyridin-2-yl)vinyl]-2,3,4,5-tetrahydro-1H-pyrido[4,3-b]indole 1.1(5), cis-2-tert-butyl-5-[2-(pyridin-3-yl)vinyl]-2,3,4,5-tetrahydro-1H-pyrido[4,3-b]indole 1.1(6), cis-2-methyl-5-styryl-8-fluoro-2,3,4,5-tetrahydro-1H-pyrido[4,3-b]indole 1.1.1(1), trans-2-methyl-5-styryl-8-fluoro-2,3,4,5-tetrahydro-1H-pyrido[4,3-b]indole 1.1.3(1), trans-2-methyl-5-[2-(pyridin-4-yl)vinyl]-8-fluoro-2,3,4,5-tetrahydro-1H-pyrido[4,3-b]indole 1.1.3(2), cis-2-methyl-5-[2-(pyridin-3-yl)vinyl]-8-fluoro-2,3,4,5-tetrahydro-1H-pyrido[4,3-b]indole 1.1.1(2), trans-2-methyl-5-(pyridin-2-yl)vinyl]-8-fluoro-2,3,4,5-tetrahydro-1H-pyrido[4,3-b]indole 1.1.3(3), cis-2,8-dimethyl-5-styryl-2,3,4,5-tetrahydro-1H-pyrido[4,3-b]indole 1.1.1(3), trans-2,8-dimethyl-5-styryl-2,3,4,5-tetrahydro-1H-pyrido[4,3-b]indole 1.1.3(4), cis-2,8-dimethyl-5-[2-(pyridin-3-yl)vinyl]-2,3,4,5-tetrahydro-1H-pyrido[4,3-b]indole 1.1.1(4), trans-2,8-dimethyl-5-[2-(pyridin-4-yl)vinyl]-2,3,4,5-tetrahydro-1H-pyrido[4,3-b]indole 1.1.3(5), cis-2-benzyl-8-methyl-5-[2-(pyridin-3-yl)vinyl]-2,3,4,5-tetrahydro-1H-pyrido[4,3-b]indole 1.1.1(5), trans-2-methyl-5-(4-fluorostyryl)-8-fluoro-2,3,4,5-tetrahydro-1H-pyrido[4,3-b]indole 1.1.3(6), cis-2-methyl-5-(3-fluorostyryl)-8-fluoro-2,3,4,5-tetrahydro-1H-pyrido[4,3-b]indole 1.1.1(6), trans-2,8-dimethyl-5-[4-(trifluoromethyl)styryl]-2,3,4,5-tetrahydro-1H-pyrido[4,3-b]indole 1.1.3(7), cis-2,8-dimethyl-5-[3-(trifluoromethyl)styryl)]-2,3,4,5-tetrahydro-1H-pyrido[4,3-b]indole 1.1.1(7), trans-2-methyl-5-[4-(trifluoromethyl)styryl)]-8-fluoro-2,3,4,5-tetrahydro-1H-pyrido[4,3-b]indole 1.1.3(8), cis-2-methyl-5-(4-methoxystyryl)-8-fluoro-2,3,4,5-tetrahydro-1H-pyrido[4,3-b]indole 1.1.1(8), cis-2-methyl-5-[4-(dimethylamino)styryl]-8-fluoro-2,3,4,5-tetrahydro-1H-pyrido[4,3-b]indole 1.1.1(9) or trans-2,8-dimethyl-5-(4-fluoro styryl)-2,3,4,5-tetrahydro-1H-pyrido[4,3-b]indole 1.1.3(9), or pharmaceutically acceptable salts thereof.

The preferred pyrido[4,3-b]indoles are substituted 5-ethyl-2,3,4,5-tetrahydro-1H-pyrido[4,3-b]indoles of the general formula 1.2, wherein:

R¹, R²ᵢ and Ar are as defined above.

The preferred pyrido[4,3-b]indoles are substituted 5-ethyl-2,3,4,5-tetrahydro-1H-pyrido[4,3-b]indoles of the general formulas 1.2.1, 1.2.2,

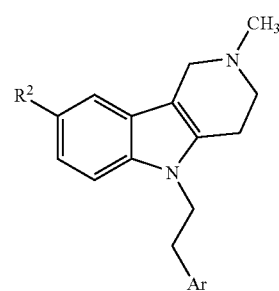

1.2.1

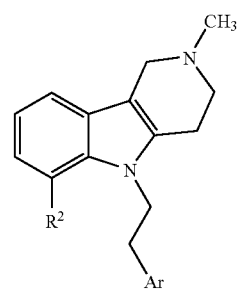

1.2.2 wherein:

R² is selected from H, F, CH₃, CF₃, OCF₃ or OCH₃;

Ar has the meanings mentioned above.

The preferred pyrido[4,3-b]indoles of the general formula 1.2 are selected from the group consisting of 2,8-dimethyl-5-(2-phenethyl)-2,3,4,5-tetrahydro-1H-pyrido[4,3-b]indole 1.2.1(1), 2,8-dimethyl-5-[2-(pyridin-2-yl)ethyl]-2,3,4,5-tetrahydro-1H-pyrido[4,3-b]indole 1.2.1(4), 2,8-dimethyl-5-[2-(pyrazin-2-yl)ethyl]-2,3,4,5-tetrahydro-1H-pyrido[4,3-b]indole 1.2.1(6), 2-methyl-5-(2-phenethyl)-8-fluoro-2,3,4,5-tetrahydro-1H-pyrido[4,3-b]indole 1.2.1(7), 2-methyl-5-[2-(pyridin-4-yl)ethyl]-8-fluoro-2,3,4,5-tetrahydro-1H-pyrido[4,3-b]indole 1.2.1(8), 2-methyl-5-[2-(pyridin-3-yl)ethyl]-8-fluoro-2,3,4,5-tetrahydro-1H-pyrido[4,3-b]indole 1.2.1(9), 2-methyl-5-[2-(pyridin-2-yl)ethyl]-8-fluoro-2,3,4,5-tetrahydro-1H-pyrido[4,3-b]indole 1.2.1(10), 2-methyl-5-[2-(6-methylpyridin-3-yl)ethyl]-8-fluoro-2,3,4,5-tetrahydro-1H-pyrido[4,3-b]indole 1.2.1(11), 2-methyl-5-(2-phenethyl)-8-trifluoromethyl-2,3,4,5-tetrahydro-1H-pyrido[4,3-b]indole 1.2.1(12), 2-methyl-5-[2-(pyridin-3-yl)ethyl]-8-trifluoromethyl-2,3,4,5-tetrahydro-1H-pyrido[4,3-b]indole 1.2.1(13), 2-methyl-5-(2-phenethyl)-6-fluoro-2,3,4,5-tetrahydro-1H-pyrido[4,3-b]indole 1.2.2(1), 2-methyl-5-(2-phenethyl)-6- trifluoromethyl-2,3,4,5-tetrahydro-1H-pyrido[4,3-b]indole 1.2.2(2) or 2-methyl-5-[2-(pyridin-3-yl)ethyl]-6-trifluoromethyl-2,3,4,5-tetrahydro-1H-pyrido[4,3-b]indole 1.2.2(3) or pharmaceutically acceptable salts thereof.

The preferred pyrido[4,3-b]indoles are substituted 5-ethynyl-2,3,4,5-tetrahydro-1H-pyrido[4,3-b]indoles of the general formula 1.3,

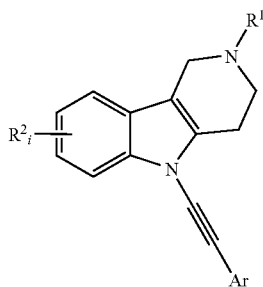

1.3 wherein:
R¹, R²$_i$ and Ar are all as defined above.

The preferred pyrido[4,3-b]indoles are substituted 5-ethynyl-2,3,4,5-tetrahydro-1H-pyrido[4,3-b]indoles of the general formulas 1.3.1, 1.3.2,

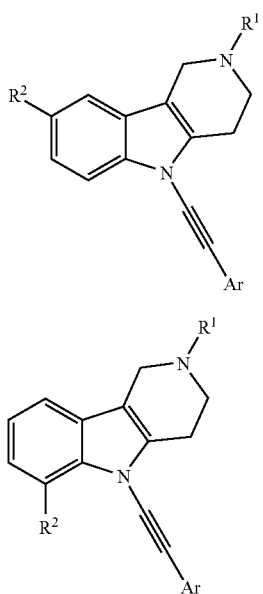

1.3.1

1.3.2 wherein:
R² is selected from H, F, CH$_3$, CF$_3$, OCF$_3$ or OCH$_3$;
R¹ and Ar are all as defined above.

The preferred pyrido[4,3-b]indoles of the general formula 1.3 are selected from the group consisting of 2-methyl-5-(phenylethynyl)-2,3,4,5-tetrahydro-1H-pyrido[4,3-b]indole 1.3(1), 2-methyl-5-(pyridin-2-ylethynyl)-2,3,4,5-tetrahydro-1H-pyrido[4,3-b]indole 1.3(2), 2-methyl-5-(pyridin-3-ylethynyl)-2,3,4,5-tetrahydro-1H-pyrido[4,3-b]indole 13(3), 2-methyl-5-(pyridin-4-ylethynyl)-2,3,4,5-tetrahydro-1H-pyrido[4,3-b]indole 1.3(4), 2-methyl-5-(pyrimidin-5-ylethynyl)-2,3,4,5-tetrahydro-1H-pyrido[4,3-b]indole 1.3(5), 2-methyl-5-(phenylethynyl)-8-fluoro-2,3,4,5-tetrahydro-1H-pyrido[4,3-b]indole 13.1(1), 2-methyl-5-(pyridin-2-yl-ethynyl)-8-fluoro-2,3,4,5-tetrahydro-1H-pyrido[4,3-b]indole 1.3.1(2), 2-methyl-5-(pyridin-3-ylethynyl)-8-fluoro-2,3,4,5-tetrahydro-1H-pyrido[4,3-b]indole 1.3.1(3), 2-methyl-5-(pyridin-4-yl ethynyl)-8-fluoro-2,3,4,5-tetrahydro-1H-pyrido[4,3-b]indole 1.3.1(4), 2-methyl-5-(pyridin-3-yl ethynyl)-6-fluoro-2,3,4,5-tetrahydro-1H-pyrido[4,3-b]indole 1.3.2(1), 2,8-dimethyl-5-(phenylethynyl)-2,3,4,5-tetrahydro-1H-pyrido[4,3-b]indole 1.3.1(5), 2,8-dimethyl-5-(pyridin-2-ylethynyl)-2,3,4,5-tetrahydro-1H-pyrido[4,3-b]indole 1.3.1(6), 2,8-dimethyl-5-(pyridin-3-ylethynyl)-2,3,4,5-tetrahydro-1H-pyrido[4,3-b]indole 1.3.1(7), 2,8-dimethyl-5-(pyridin-4-ylethynyl)-2,3,4,5-tetrahydro-1H-pyrido[4,3-b]indole 1.3.1(8), 2-methyl-5-(pyridin-3-ylethynyl)-8-(trifluoromethyl)-2,3,4,5-tetrahydro-1H-pyrido[4,3-b]indole 1.3.1(9), 2-methyl-5-[(4-methoxyphenyl)ethynyl]-8-fluoro-2,3,4,5-tetrahydro-1H-pyrido[4,3-b]indole 1.3.1(10), 2-methyl-5-[(4-fluorophenyl)ethynyl]-8-fluoro-2,3,4,5-tetrahydro-1H-pyrido[4,3-b]indole 1.3.1(11), 2-methyl-5-[(3-fluorophenyl)ethynyl]-8-fluoro-2,3,4,5-tetrahydro-1H-pyrido[4,3-b]indole 1.3.1(12), 2-methyl-5-[((4-trifluoromethyl)phenyl)ethynyl]-8-fluoro-2,3,4,5-tetrahydro-1H-pyrido[4,3-b]indole 1.3.1(13), 2-methyl-5-(pyridin-3-ylethynyl)-8-(trifluoromethyl)-2,3,4,5-tetrahydro-1H-pyrido[4,3-b]indole 1.3.1(14), 2,8-dimethyl-5-[(4-fluorophenyl)ethynyl]-2,3,4,5-tetrahydro-1H-pyrido[4,3-b]indole 1.3.1(15), 2,8-dimethyl-5-[(3-fluorophenyl)ethynyl]-2,3,4,5-tetrahydro-1H-pyrido[4,3-b]indole 1.3.1(16), 2,8-dimethyl-5-[((4-trifluoromethyl)phenyl)ethynyl]-2,3,4,5-tetrahydro-1H-pyrido[4,3-b]indole 1.3.1(17), 2,8-dimethyl-5-[((3-trifluoromethyl)phenyl)ethynyl]-2,3,4,5-tetrahydro-1H-pyrido[4,3-b]indole 1.3.1(18), 2,8-dimethyl-5-[((2-trifluoromethyl)phenyl)ethynyl]-2,3,4,5-tetrahydro-1H-pyrido[4,3-b]indole 1.3.1(19), 2,8-dimethyl-5-[(2-fluorophenyl)ethynyl]-2,3,4,5-tetrahydro-1H-pyrido[4,3-b]indole 1.3.1(20), 2,8-dimethyl-5-[(4-methoxyphenyl)ethynyl]-2,3,4,5-tetrahydro-1H-pyrido[4,3-b]indole 1.3.1(21), 2,8-dimethyl-5-[((4-dimethylamino)phenyl)ethynyl]-2,3,4,5-tetrahydro-1H-pyrido[4,3-b]indole 1.3.1(22), 2,8-dimethyl-5-[(3-methoxyphenyl)ethynyl]-2,3,4,5-tetrahydro-1H-pyrido[4,3-b]indole 1.3.1(23) or 2,8-dimethyl-5-[(2-methoxyphenyl)ethynyl]-2,3,4,5-tetrahydro-1H-pyrido[4,3-b]indole 1.3.1(24) or pharmaceutically acceptable salts thereof.

The purpose of the present invention is also methods for the synthesis of substituted 2,3,4,5-tetrahydro-1H-pyrido[4,3-b]indoles of the general formula 1, pharmaceutically acceptable salts and/or hydrates thereof.

According to the invention the method for synthesis of substituted 5-ethenyl-2,3,4,5-tetrahydro-1H-pyrido[4,3-b]indoles of the general formula 1.1 consists in interaction of 2,3,4,5-tetrahydro-1H-pyrido[4,3-b]indoles of the general formula 2 with the corresponding acetylenes of the general formula 3 according to scheme 1.

Scheme 1

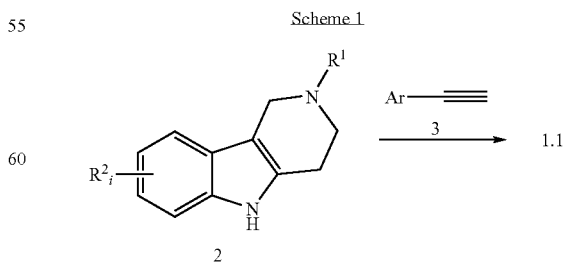

wherein:
R¹, R²$_i$ and Ar are all as defined above.

According to the invention the method for synthesis of substituted 5-[2-aryl(or heterocyclyl)ethyl]-2,3,4,5-tetrahydro-1H-pyrido[4,3-b]indoles of the general formula 1.2 consists in hydrogenation of substituted 5-ethenyl-2,3,4,5-tetrahydro-1H-pyrido[4,3-b]indoles of the general formula 1.1 according to scheme 2.

Scheme 2

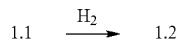

According to the invention the method for synthesis of substituted 5-[2-aryl(or heterocyclyl)ethyl]-2,3,4,5-tetrahydro-1H-pyrido[4,3-b]indoles of the general formula 1.2 consists in interaction of 2,3,4,5-tetrahydro-1H-pyrido[4,3-b]indoles of the general formula 2 with substituted ethylene of the general formula 4 according to scheme 3.

Scheme 3

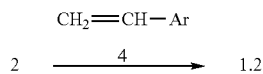

wherein:

Ar represents optionally substituted phenyl or optionally substituted 6-membered aromatic heterocycle containing 1 or 2 nitrogen atom in the cycle.

According to the invention the method for synthesis of 5-ethynyl-2,3,4,5-tetrahydro-1H-pyrido[4,3-b]indoles of the general formula 1.3 consists in interaction of 2,3,4,5-tetrahydro-1H-pyrido[4,3-b]indoles of the general formula 2 with the corresponding halogen acetylenes of the general formula 5 according to the following scheme 4.

Scheme 4

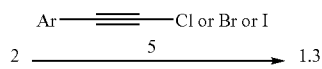

wherein:

Hal are Cl, Br or I;

Ar represents optionally substituted phenyl or optionally substituted 6-membered aromatic heterocycle containing 1 or 2 nitrogen atom in the cycle.

The starting 2,3,4,5-tetrahydro-1H-pyrido[4,3-b]indoles of the general formula 2 are prepared by the methods known in the art for the preparation of analogous compounds.

The starting 2,3,4,5-tetrahydro-1H-pyrido[4,3-b]indoles of the general formula 2 with various substituents in 2 and 8 positions are prepared by known Fisher indole synthesis. The reaction involves the interaction of substituted phenylhydrazine 2.1 (or their salts) and 1-substituted piperidine-4-ones 5, with the subsequent cyclization of the intermediate product as described in [N. Barbulescu, C. Bornaz, C. si Greff—Rev. Chim. (Bucuresti), 1971, v. 22, p. 269] according to scheme 5.

Scheme 5

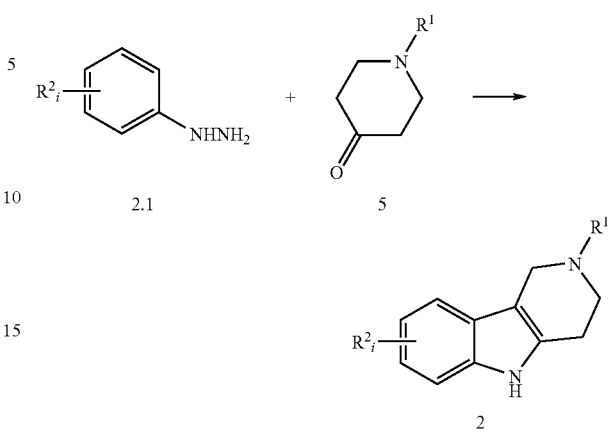

wherein:

$R^1$ and $R^2_i$ are all as defined above; in addition to, $R^1$ may represent ethoxycarbonyl or tert-butyloxycarbonyl.

The starting compounds of the general formula 2 may also be prepared by interaction of 2,3,4,5-tetrahydro-1H-pyrido [4,3-b]indoles of the general formula 2.2 with isocyanates 2.3, isothiocyanates 2.4 or sulfonyl chlorides 2.5 according to scheme 6.

Scheme 6

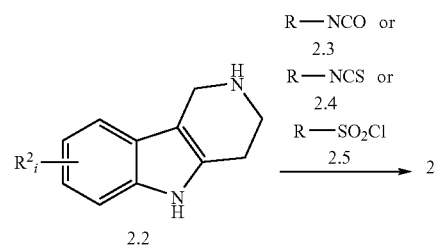

wherein:

$R^2_i$ is as defined above; R represents the corresponding substituent.

Substituted 2,3,4,5-tetrahydro-1H-pyrido[4,3-b]indoles of the general formula 1 may form hydrates and pharmaceutically acceptable salts. Both organic and mineral acids could be used for salts preparation, for example, hydrochloric acid, hydrobromic acid, hydriodic acid, sulfuric acid, phosphoric acid, formic acid, acetic acid, propionic acid, trifluoroacetic acid, maleic acid, tartaric acid, methanesulphonic acid, benzenesulfonic acid, p-toluenesulfonic acid. Hydrates are usually formed during recrystallization of compounds of the general formula 1 or their salts from water or water containing solvents.

BEST EMBODIMENT OF THE INVENTION

The invention is illustrated by the following figures:

FIG. 1. The dependencies of the inhibition of serotonin stimulated production of intracellular cAMP by the tested compounds. ■—1.1(1), □—1.1(2), ○—1.2.1(1)HCl, ●—1.3.1(1).

Figure 2:
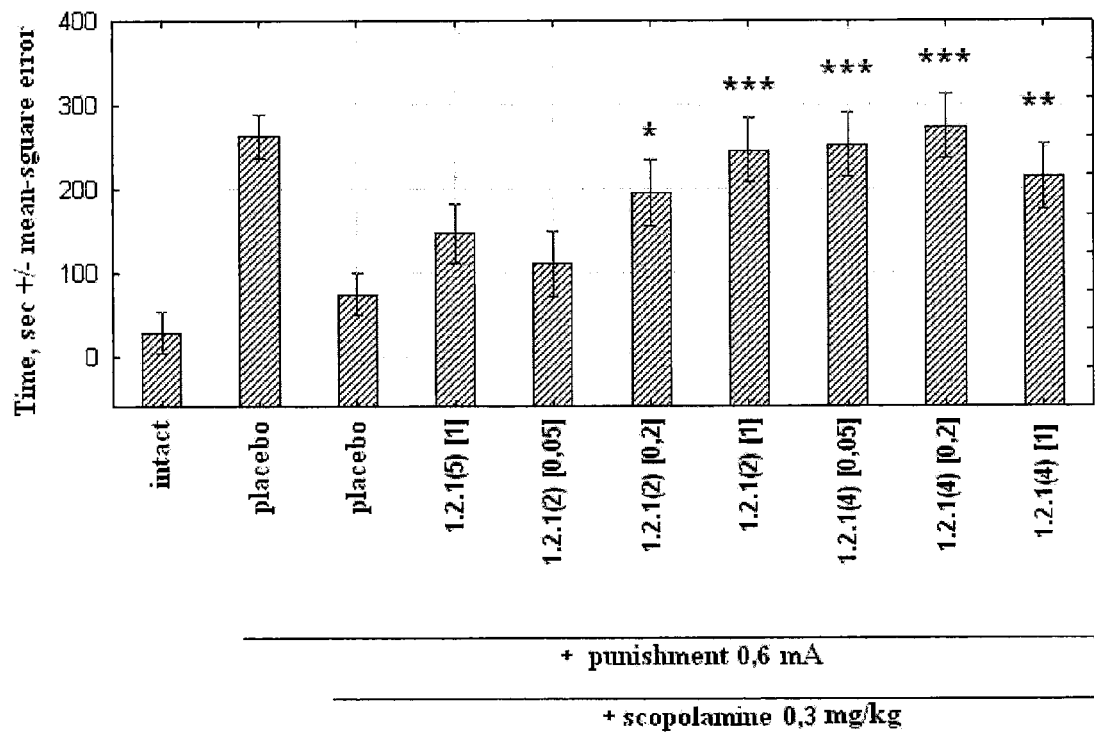

FIG. 2. The influence of 5-$HT_6$ receptors antagonists 1.2.1 (2)HCl, 1.2.1(4)HCl and 1.2.1(5)HCl on the latent period of the first entry into the dark section of the shuttle chamber in the test of passive avoidance with BALB/c mail mice. The figures in brackets mean the dosages of the tested compounds in mg/kg: *—the statistically significant difference from the group of animals received placebo at $p<0.05$, —at $p<0.01$, *—at $p<0.001$.

Figure 3:
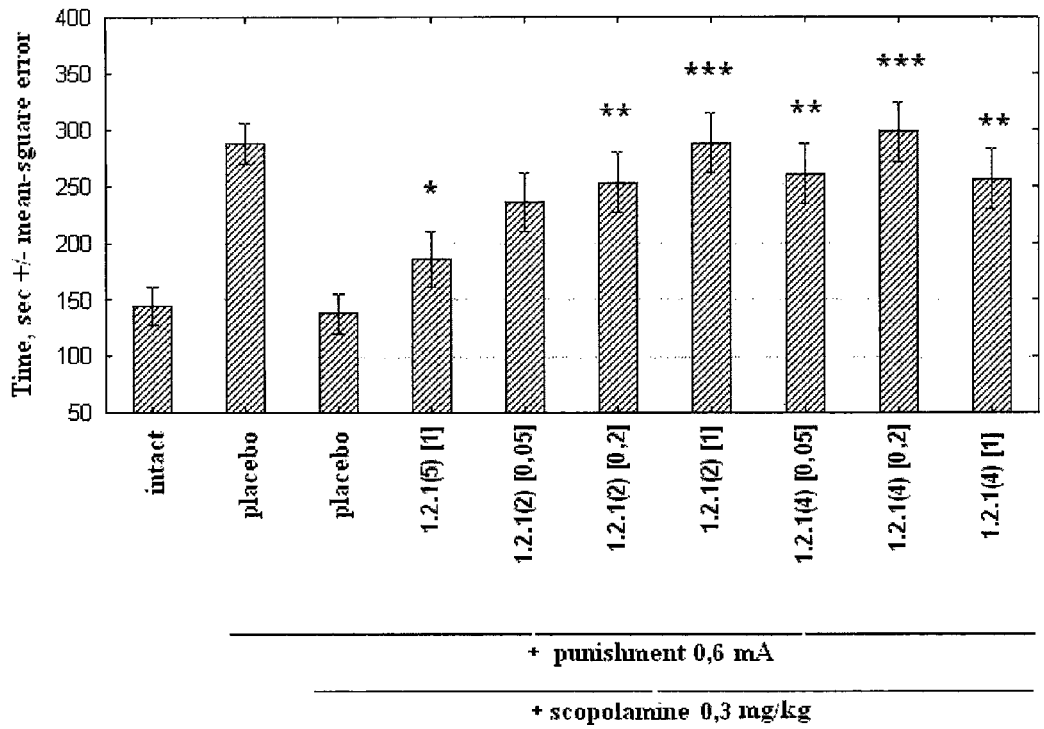

FIG. 3. The influence of 5-$HT_6$ receptors antagonists 1.2.1 (2)HCl, 1.2.1(4)HCl and 1.2.1(5)HCl on the time BALB/c male mice spent in the light section of the shuttle chamber in the test of passive avoidance. The figures in brackets mean the dosages of the tested compounds in mg/kg: *—the statistically significant difference from the group of animals received placebo at $p<0.05$, —at $p<0.01$, *—at $p<0.001$.

Figure 4:
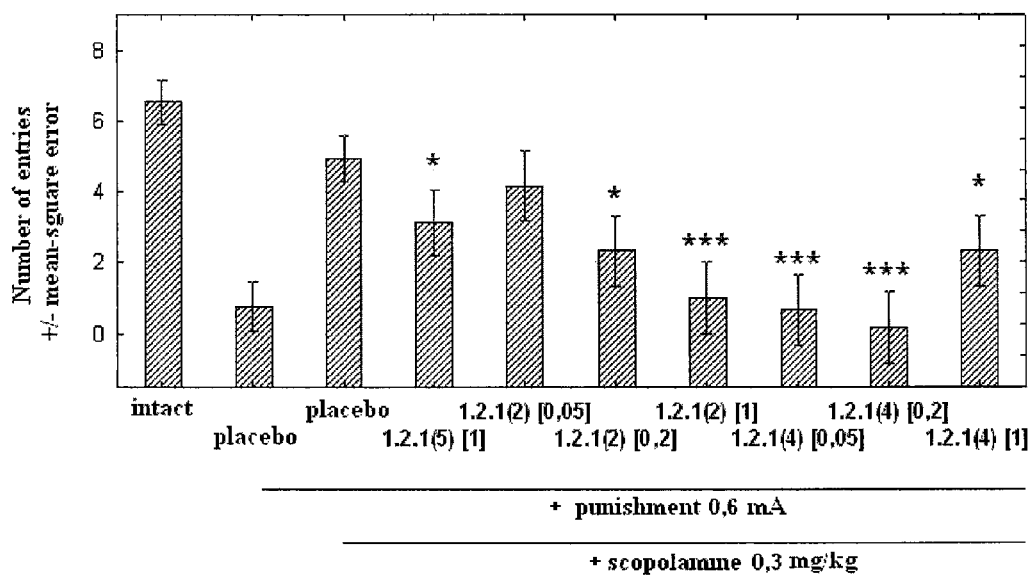

FIG. 4. The influence of 5-$HT_6$ receptors antagonists 1.2.1 (2)HCl, 1.2.1(4)HCl and 1.2.1(5)HCl on the number of entries into the dark section of the shuttle chamber in the test of passive avoidance with BALB/c male mice The figures in brackets mean the dosages of the tested compounds in mg/kg. *—the statistically significant difference from the group of animals receiving a placebo at $p<0.05$, ***—at $p<0.001$.

Figure 5:
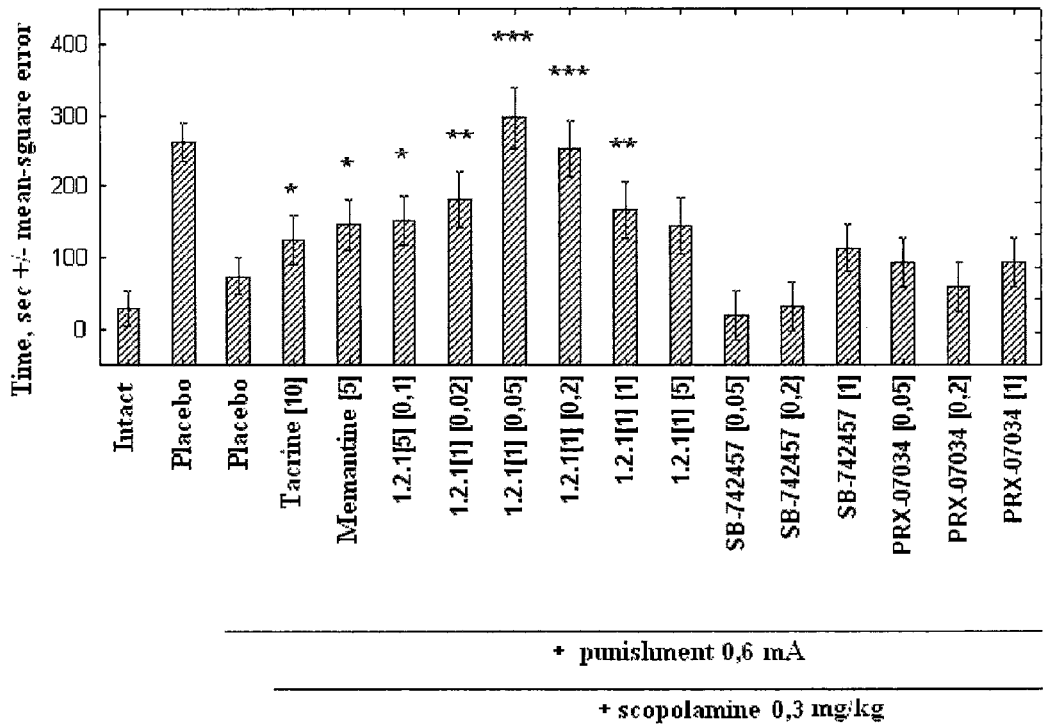

FIG. 5. The latent period of the first entry into the dark section of the shuttle chamber in the test of passive avoidance with BALB/c male mice. The figures in brackets mean the dosages of the tested compounds in mg/kg: *—the statistically significant difference from the group of animals receiving Scopolamine at $p<0.05$, —at $p<0.01$, *—at $p<0.001$.

Figure 6:
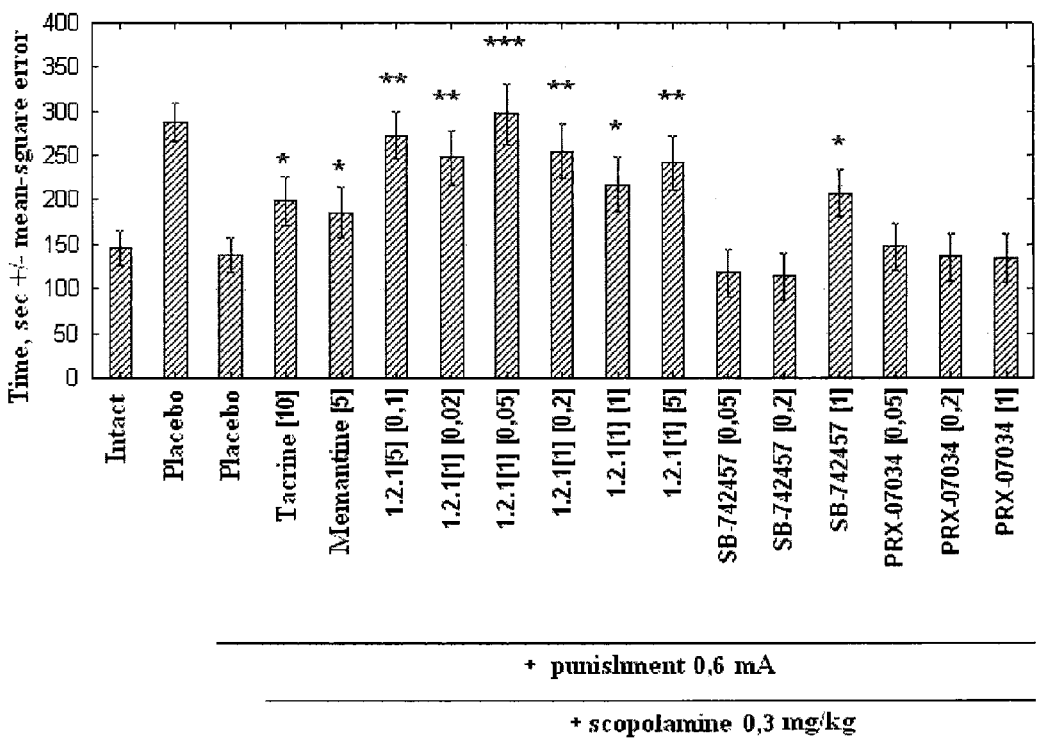

FIG. 6. The time spent by BALB/c male mice in the light section of the shuttle chamber in the test of passive avoidance. The figures in brackets mean the dosages of the tested compounds in mg/kg: *—the statistically significant difference from the group of animals received Scopolamine at $p<0.05$, —at $p<0.01$, *—at $p<0.001$.

Figure 7:
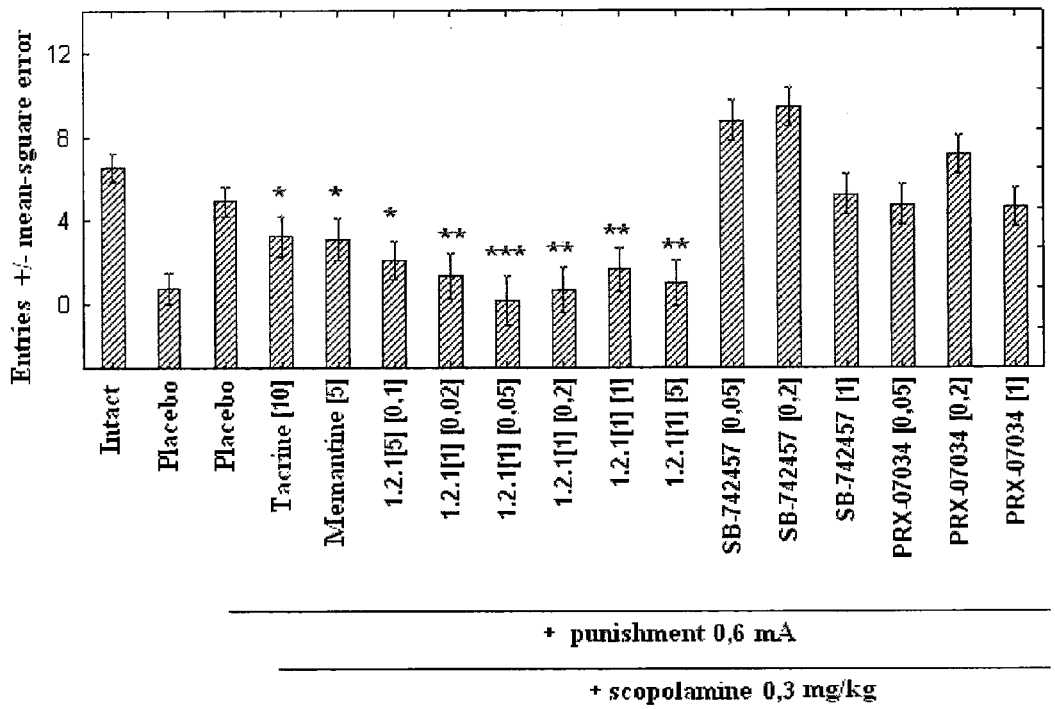

FIG. 7. The number of entries into the dark section of the shuttle chamber in the test of passive avoidance with BALB/c male mice. The figures in brackets mean the dosages of the tested compounds in mg/kg: *—the statistically significant difference from the group of animals received Scopolamine at $p<0.05$, ***—at $p<0.001$.

Figure 8:
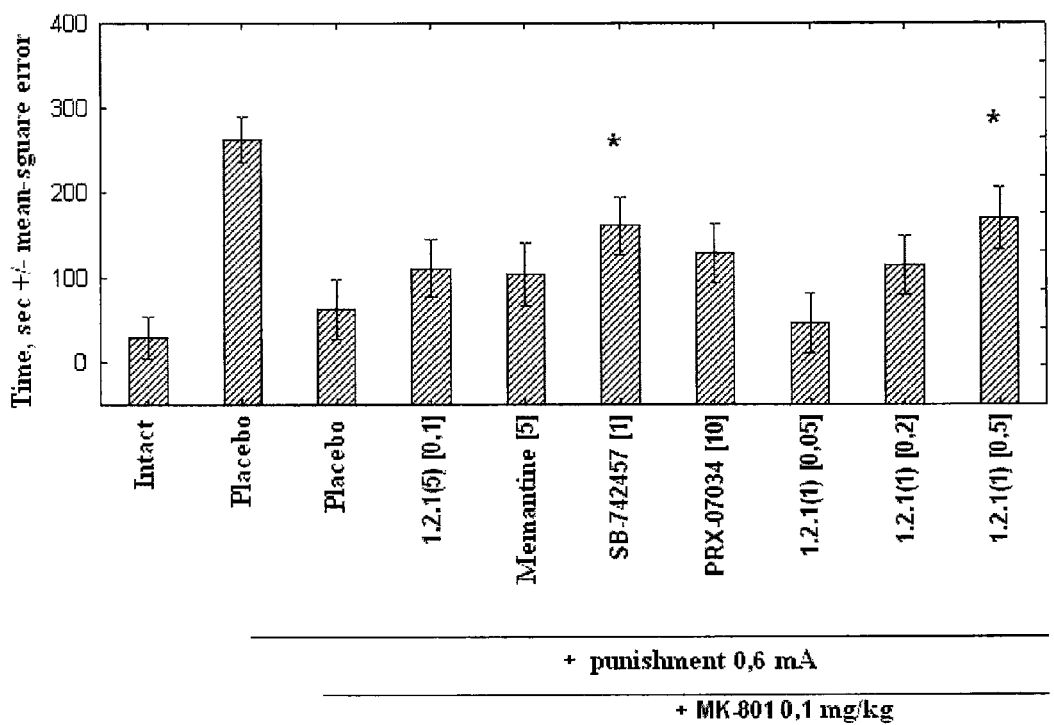

FIG. 8. The latent period of the first entry into the dark section of the shuttle chamber in the test of passive avoidance with BALB/c male mice. The figures in brackets mean the dosages of the tested compounds in mg/kg: *—the statistically significant difference from the group of animals received MK-801 at $p<0.05$.

Figure 9:
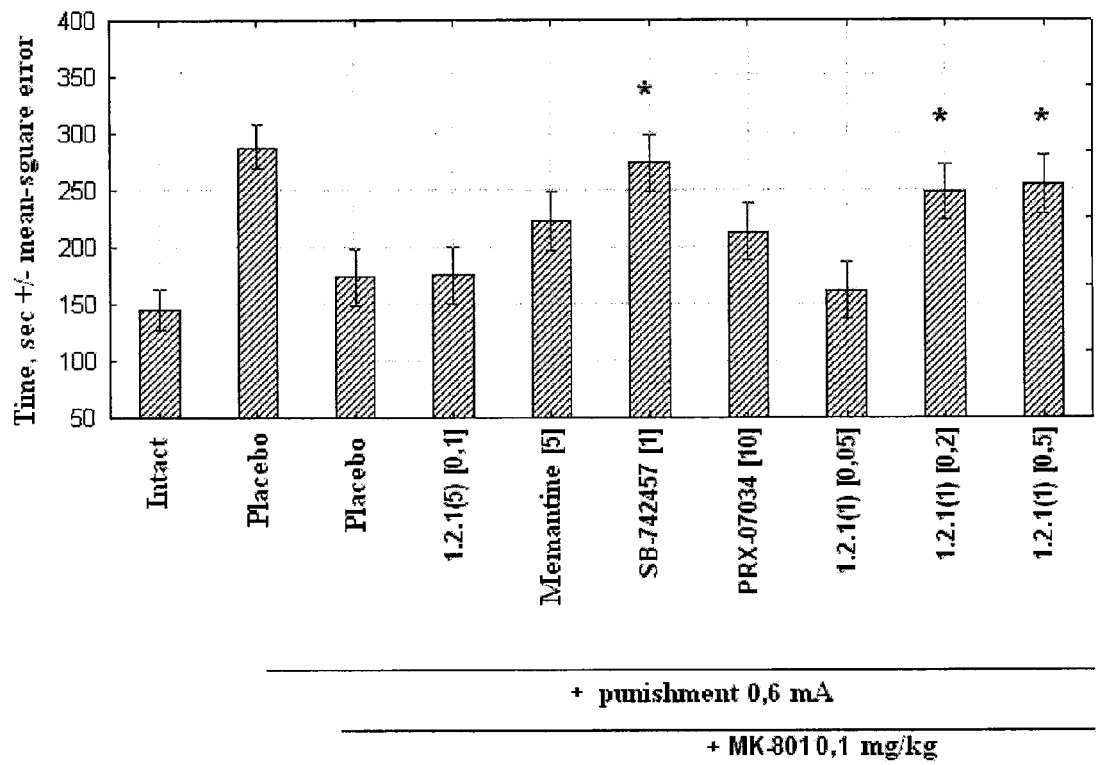

FIG. 9. The time spent in the light section of the shuttle chamber in the test of passive avoidance with BALB/c male mice. The figures in brackets mean the dosages of the tested compounds in mg/kg. *—the statistically significant difference from the group of animals received MK-801 at $p<0.05$.

Figure 10:
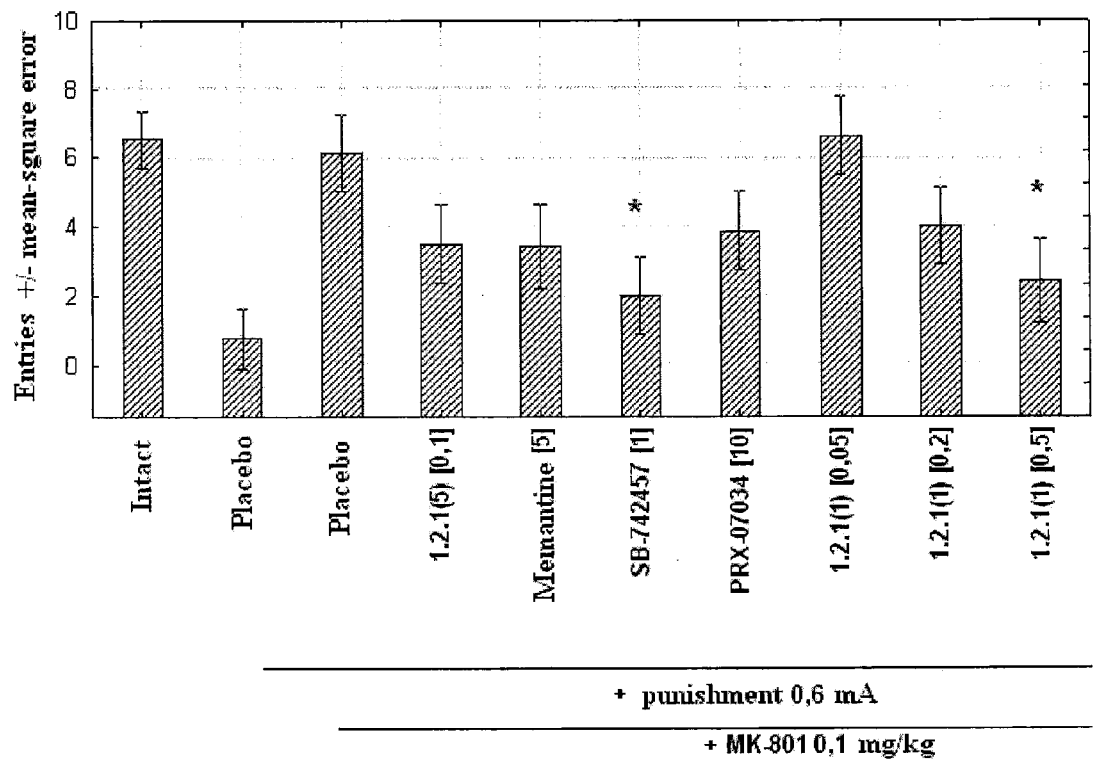

FIG. 10. The number of entries into the dark section of the shuttle chamber in the test of passive avoidance with BALB/c male mice. The figures in brackets mean the dosages of the tested compounds in mg/kg: *—the statistically significant difference from the group of animals received MK-801 at $p<0.05$.

Figure 11:
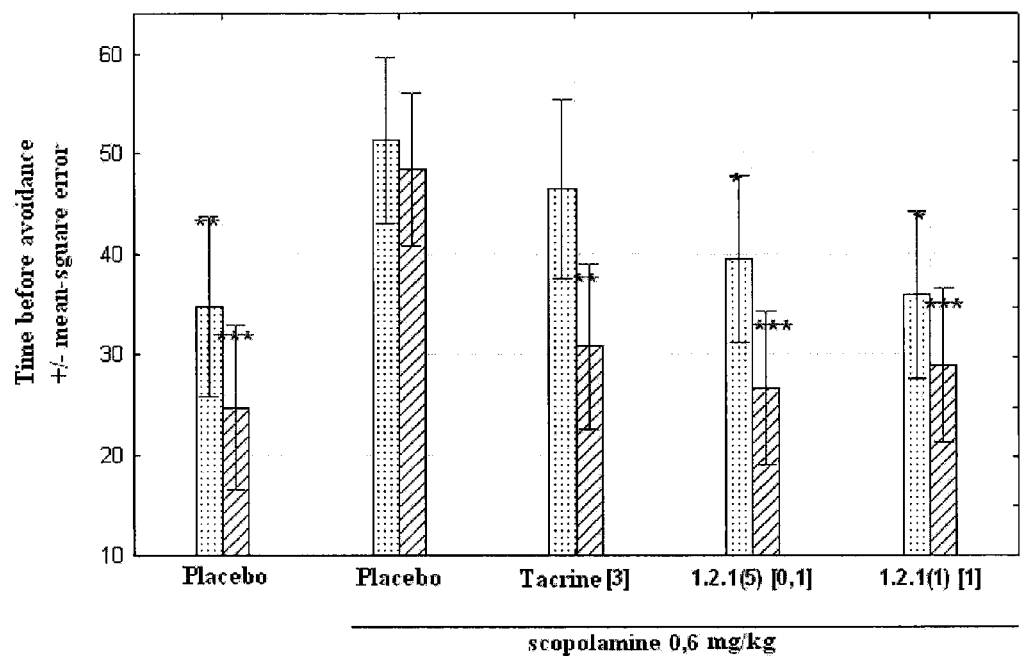

FIG. 11. The latent period of avoidance of climbing on the platform, (average value of 0.4 experiments during one day) in the first 2 days of mice training in the test of Morris water Maze. The figures in brackets mean the dosages of the tested compounds in mg/kg: Day 1 Day 2; *—the statistically significant difference from the group of animals received Scopolamine at $p<0.05$, —at $p<0.01$; *—at $p<0.001$.

Figure 12:
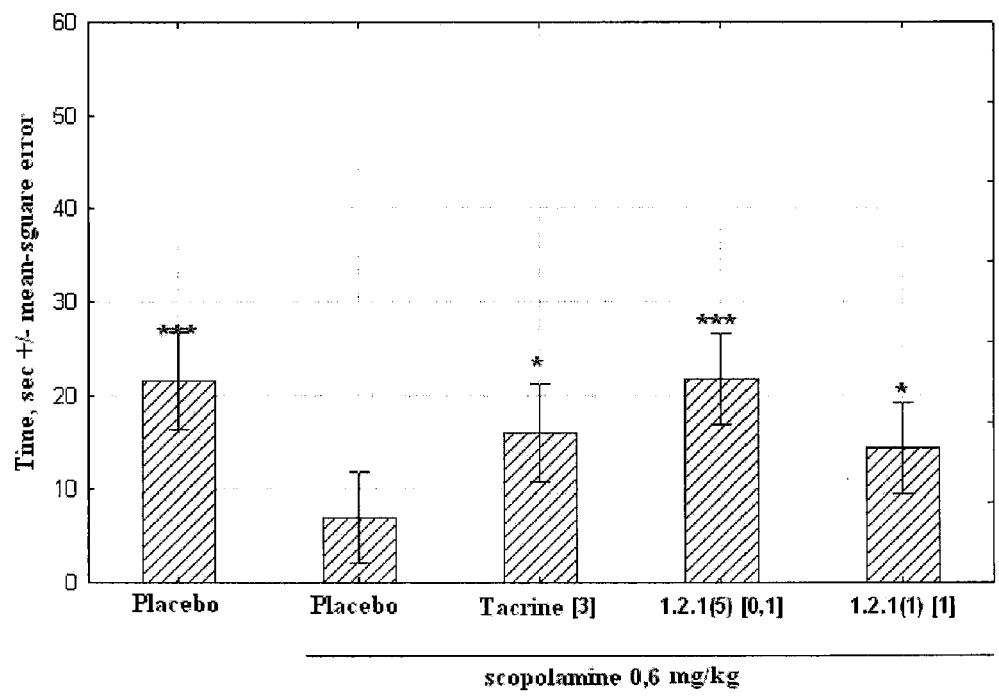

FIG. 12. The time spent by mice in the area of the platform after two days of training in the Morris water Maze. The figures in brackets mean the dosages of the tested compounds in mg/kg. The difference from the group of animals received Scopolamine: *—at $p<0.05$, ***—at $p<0.001$.

Figure 13:
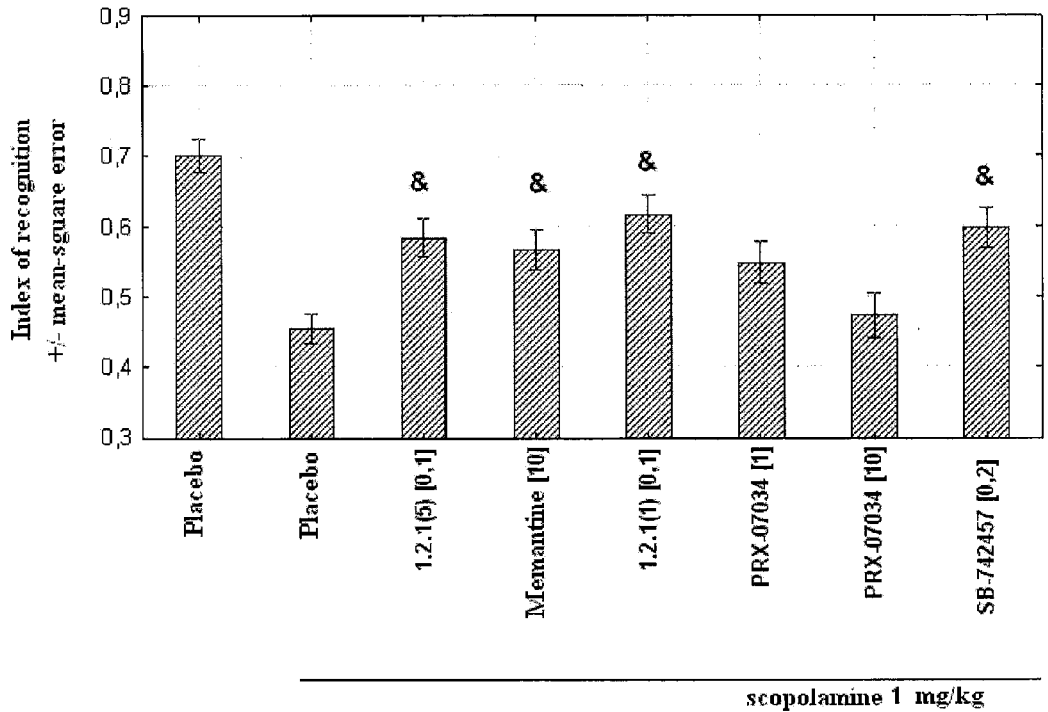

FIG. 13. Index of novel object recognition at SHK male mice. The numbers in brackets mean the dosages of the tested compounds in mg/kg. &—statistically significant difference from the group of animals received Scopolamine at $p<0.05$.

Figure 14:
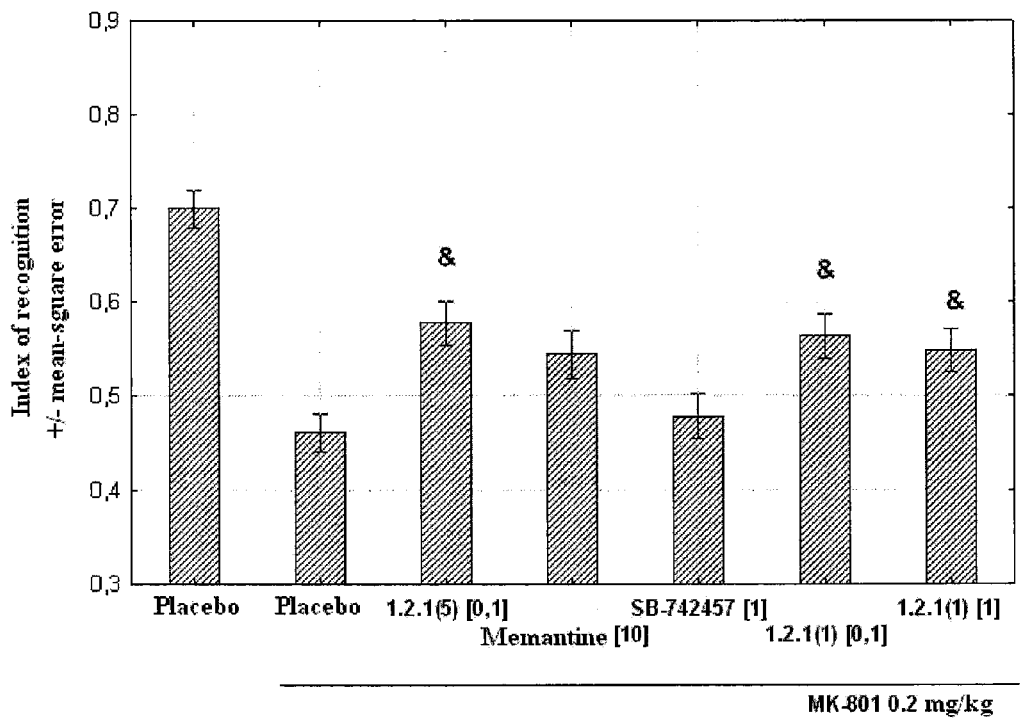

FIG. 14. Index of novel object recognition at SHK male mice. The numbers in brackets mean the dosages of the tested compounds in mg/kg. &—statistically significant difference from the group of animals received Scopolamine at $p<0.05$.

Figure 15:
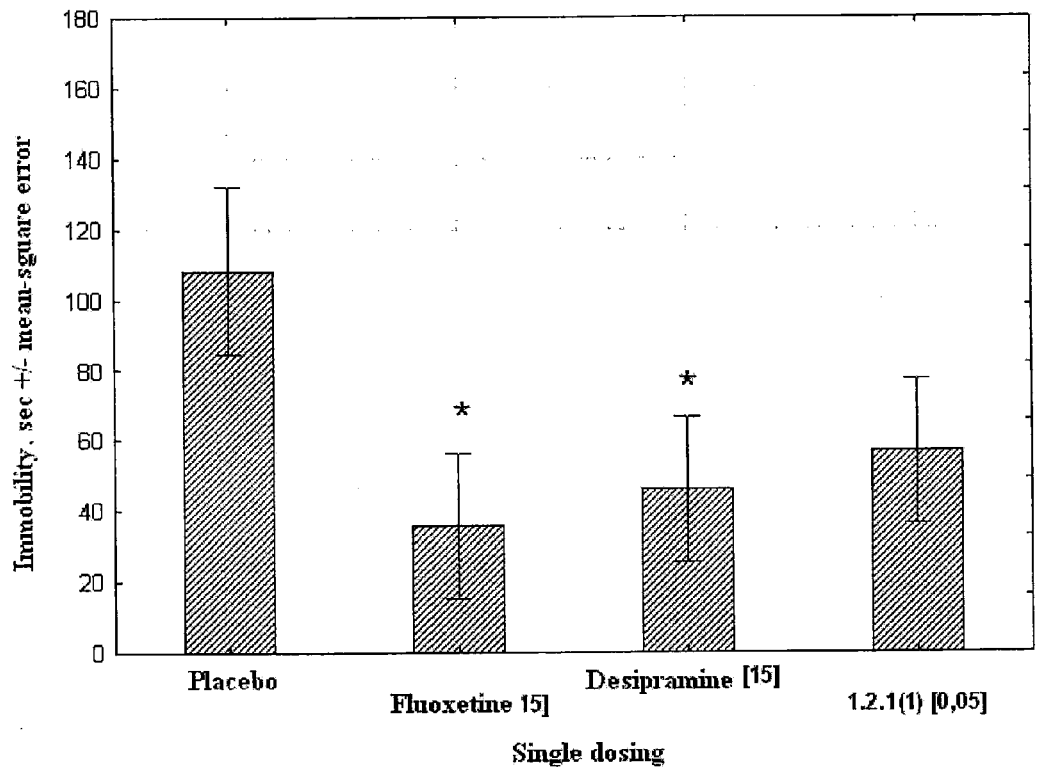

FIG. 15. The influence of standard antidepressants Fluoksetine, Dezipramine and 5-$HT_6$ receptors antagonist 1.2.1(1) HCl on the total time of mice immobility in the Porsolt test. The figures in brackets mean the dosages of the used compounds in mg/kg. *—statistically significant difference from the group of animals received placebo at $p<0.05$.

Figure 16:
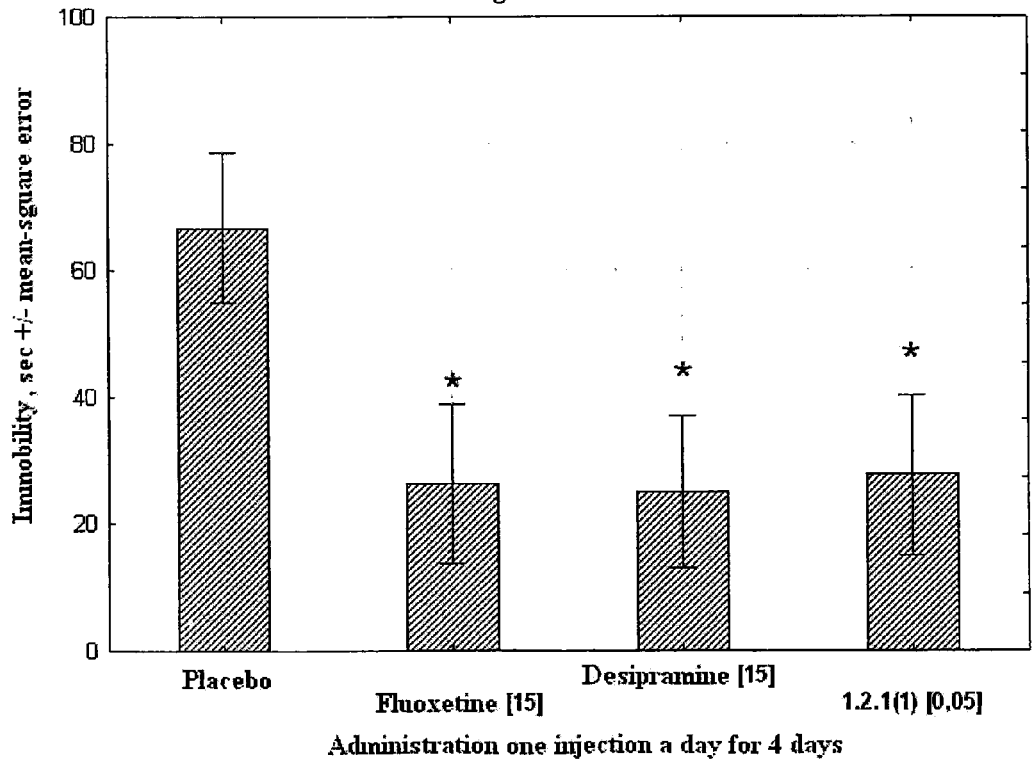

FIG. 16. The influence of standard antidepressants Fluoksetine, Dezipramine and 5-$HT_6$ receptors antagonist 1.2.1(1) HCl on the total time of mice immobility in the Porsolt test with BALB/c male mice. The figures in brackets mean the dosages of the used compounds in mg/kg. *—statistically significant difference from the group of animals received placebo at $p<0.05$.

Figure 17:
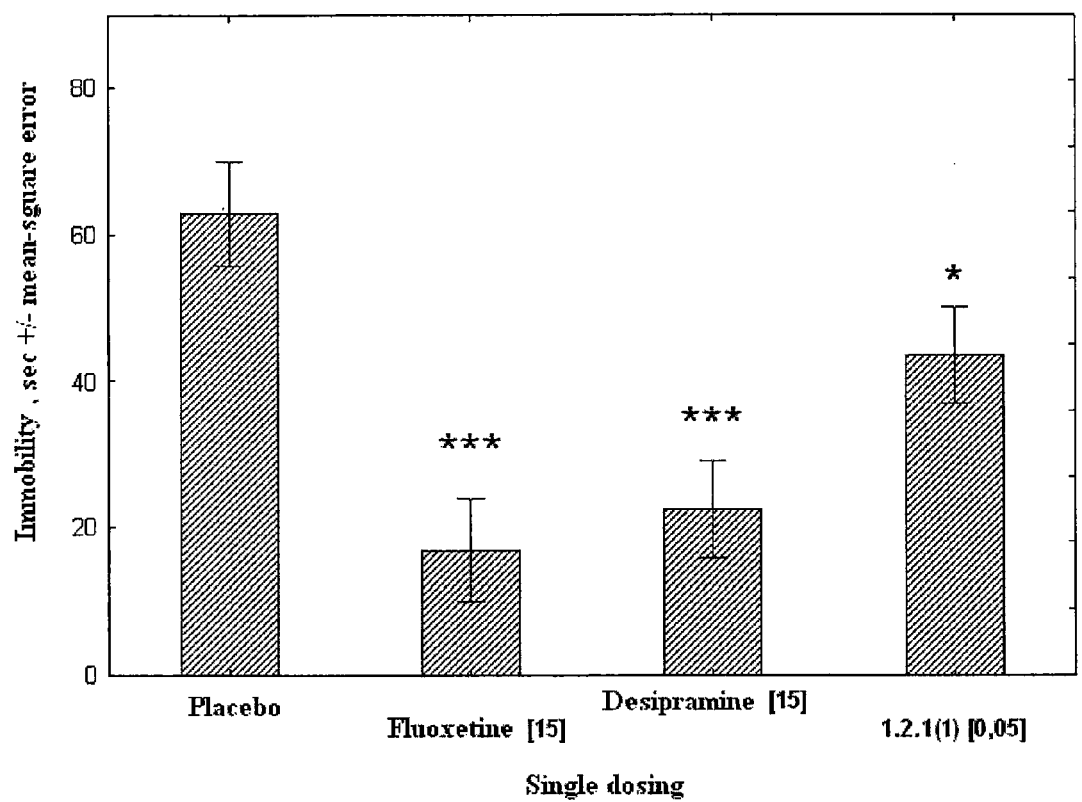

FIG. 17. The influence of standard antidepressants Fluoksetine, Dezipramine and 5-$HT_6$ receptors antagonist 1.2.1(1) HCl on the total time of mice immobility in the tail suspension test with male mice of BALB/c line. The figures in brackets mean the dosages of the used compounds in mg/kg. *—statistically significant difference from the group of animals received placebo at $p<0.05$; ***—at $p<0.001$.

Figure 18:
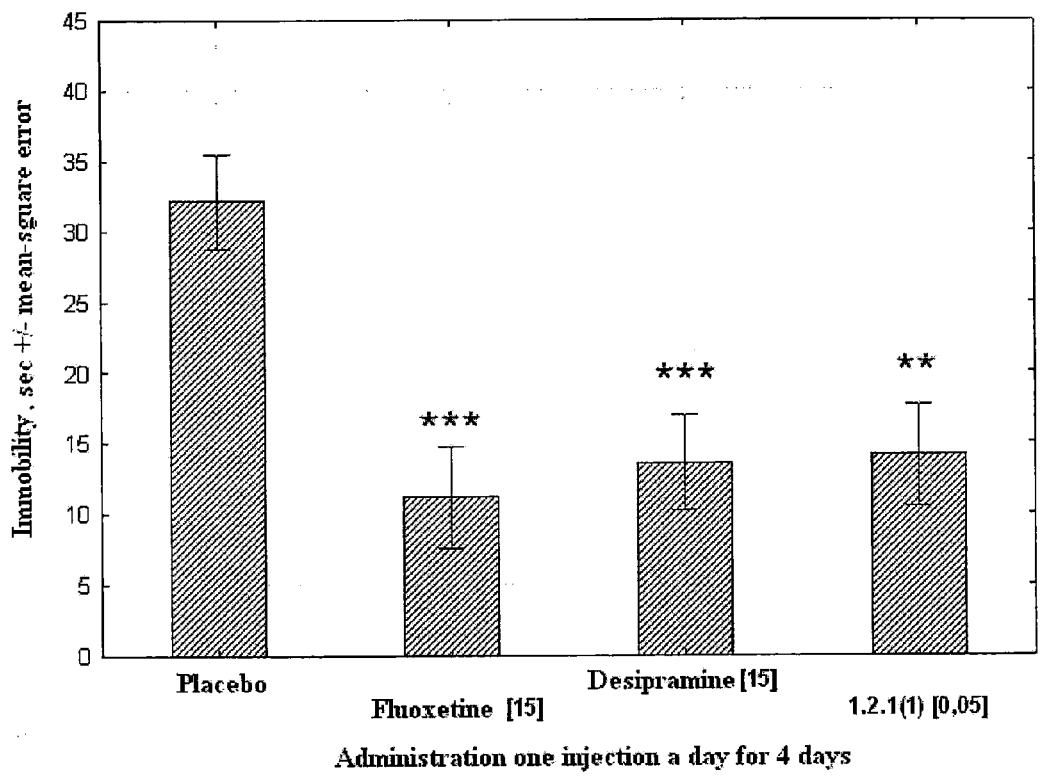

FIG. 18. The influence of standard antidepressants Fluoksetine, Dezipramine and 5-$HT_6$ receptors antagonist 1.2.1(1) HCl on the total time of mice immobility in the tail suspension test with male mice of BALB/c line. The figures in brackets mean the dosages of the used compounds in mg/kg. —statistically significant difference from the group with male mice of BALB/c line received placebo at $p<0.01$; *—at $p<0.001$.

Figure 19:
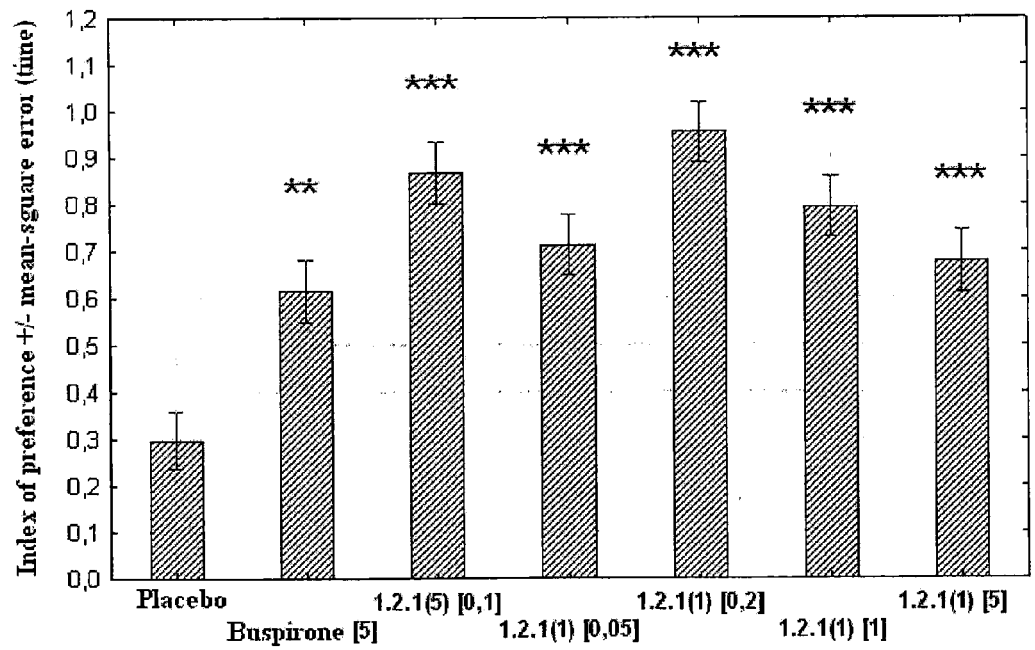

FIG. 19. The influence of standard anxiolytic (tranquilizer) Buspirone, and 5-$HT_6$ receptors antagonists 1.2.1(1)HCl and of 1.2.1(5)HCl on the preference index calculated on the time spent by BALB/c male mice in the open arms of the Maze. The figures in brackets mean the dosages of the used compounds in mg/kg. —statistically significant difference from the group of animals received placebo at $p<0.05$; *—at $p<0.001$.

Figure 20:
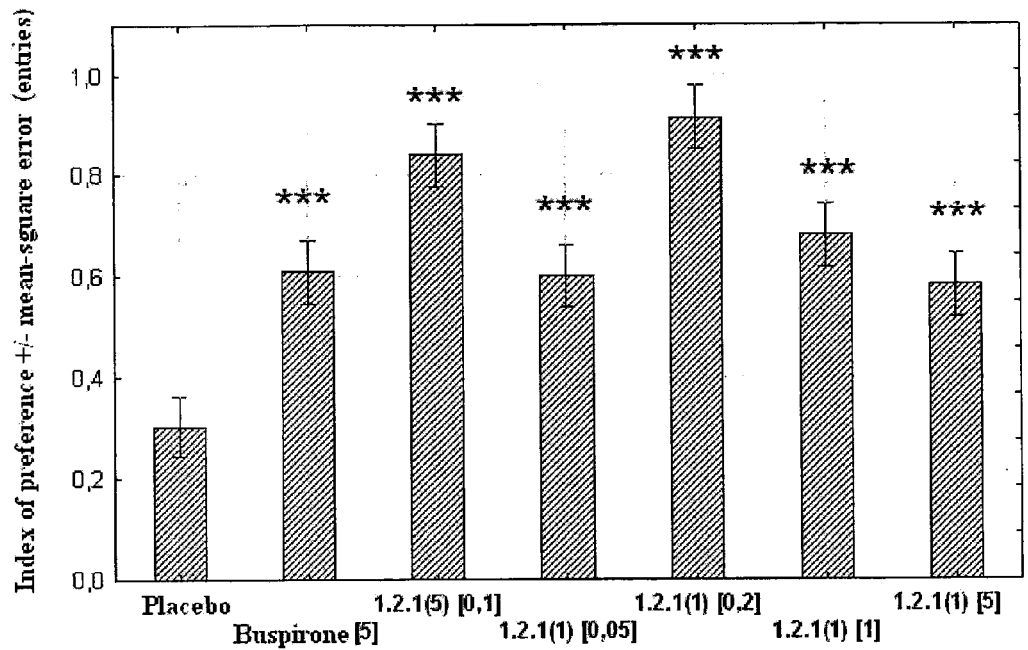
Figure 21:
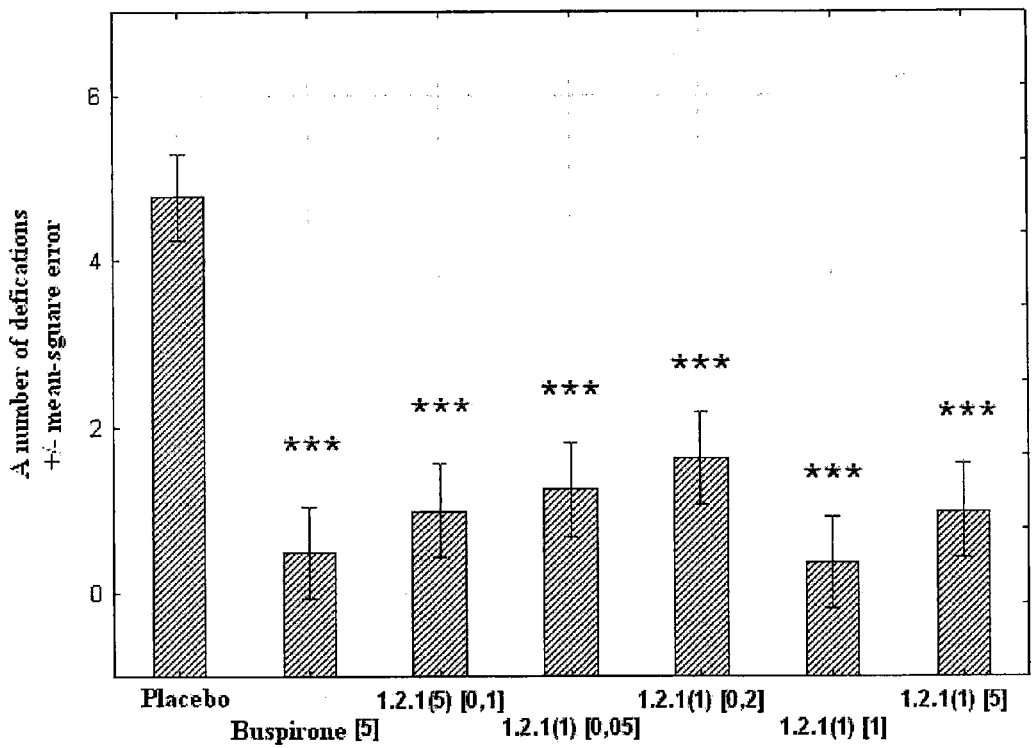

FIG. 20. The influence of standard anxiolytic (tranquilizer) Buspirone and 5-$HT_6$ receptors antagonists 1.2.1(1)HCl and 1.2.1(5)HCl on the preference index calculated on the number of entries made by BALB/c male mice to the open arms of the Maze. The figures in brackets mean the dosages of the tested compounds in mg/kg. *—statistically significant difference from the group of animals received placebo at $p<0.001$ FIG. 21. The influence of standard anxiolytic (tranquilizer) Buspirone and 5-$HT_6$ receptor antagonists 1.2.1(1)HCl and 1.2.1(5)HCl on the number of defecations made by BALB/c male mice in the Maze. The figures in brackets mean the dosages of the tested compounds in mg/kg. *—statistically significant difference from the group of animals received placebo at $p<0.001$ Below the invention is described by means of specific examples, which illustrate but not limit the scope of the invention.

EXAMPLE 1

General method for preparation of 5-[2-aryl(or azaheterocyclyl)ethenyl]-2,3,4,5-tetrahydro-1H-pyrido[4,3-b]indoles of the general formula 1.1

1 A mixture of mmol of 2,3,4,5-tetrahydro-1H-pyrido[4,3-b]indole 2, 1.5-2 mmol of aryl(or azaheterocyclyl)acetylene 3, 1 ml of dimethylsulfoxide, 3 ml of 60% water KOH solution and 100 mkl of 50% $(Bu_4N)_2SO_4$ water solution is stirred vigorously under argon atmosphere for 6-12 h at 20-80° C. Monitoring of the reaction is carried out by means of LCMS. Upon completion of the reaction the mixture is diluted with dichloromethane and washed with water. Organic layer is separated, dried over $Na_2SO_4$, and evaporated. The residue is purified by chromatography on silica gel impregnated with triethylamine [eluent-hexane-chloroform-$Et_3N$ mixture (6:3:1)]. 5-[2-Aryl(or azaheterocyclyl)ethenyl]-2,3,4,5-tetrahydro-1H-pyrido[4,3-b]indoles of the general formula 1.1 are prepared, among them: cis-2-methyl-5-styryl-2,3,4,5-tetrahydro-1H-pyrido[4,3-b]indole 1.1(1), LCMS: m/z 289 [M+H], $^1H$ NMR (400 MHz, DMSO-$d_6$): 7.46-7.43 (m, 1H), 7.23-7.19 (m, 3H), 7.12-7.05 (m, 3H), 6.99-6.95 (m, 2H), 6.97-6.95 (d, 1H, J=8.66 Hz), 6.71-6.69 (d, 1H, J=8.66 Hz), 3.60 (s, 2H), 2.65-2.62 (m, 2H), 2.55-2.54 (m, 2H), 2.43 (s, 3H); trans-2-methyl-5-styryl-2,3,4,5-tetrahydro-1H-pyrido[4,3-b]indole 1.1(2), LCMS: m/z 289 [M+H], $^1H$ NMR (400 MHz, DMSO-$d_6$): 7.88-7.85 (m, 1H), 7.84-7.80 (d, 1H, J=14.65 Hz), 7.68-7.66 (m, 2H), 7.47-7.40 (m, 3H), 7.30-7.23 (m, 2H), 7.18-7.14 (m, 1H), 6.90-6.87 (d, 1H, J=14.65 Hz), 3.59 (s, 2H), 3.06-3.04 (m, 2H), 2.80-2.77 (m, 2H), 2.49 (s, 3H); trans-2-methyl-5-[2-(pyridin-4-yl)vinyl]-2,3,4,5-tetrahydro-1H-pyrido[4,3-b]indole 1.1(3), LCMS: m/z 290 [M+H], $^1H$ NMR (400 MHz, DMSO-$d_6$): 8.55-8.53 (m, 2H), 8.12-8.08 (d, 1H, J=15.02 Hz), 7.98-7.96 (m, 1H), 7.66-7.65 (m, 2H), 7.49-7.47 (m, 1H), 7.30-7.18 (m, 2H), 6.87-6.83 (d, 1H, J=15.02 Hz), 3.60 (s, 2H), 3.10-3.07 (m, 2H), 2.82-2.79 (m, 2H), 2.49 (s, 3H); cis-2-methyl-5-[2-(pyridin-3-yl)vinyl]-2,3,4,5-tetrahydro-1H-pyrido[4,3-b]indole 1.1(4), LCMS: m/z 290 [M+H], $^1H$ NMR (400 MHz, DMSO-$d_6$): 8.59-8.57 (m, 1H), 8.24-8.20 (d, 1H, J=14.65 Hz), 7.92-7.88 (m, 1H), 7.82-7.77 (m, 1H), 7.58-7.56 (m, 1H), 7.30-7.23 (m, 2H), 7.12-7.07 (m, 1H), 7.00-6.96 (d, 1H, J=14.65 Hz), 3.55 (s, 2H), 3.05-3.03 (m, 2H), 2.81-2.78 (m, 2H), 2.48 (s, 3H); trans-2-methyl-5-[2-(pyridin-2-yl)vinyl]-2,3,4,5-tetrahydro-1H-pyrido[4,3-b]indole 1.1(5), LCMS: m/z 290 [M+H], $^1H$ NMR (400 MHz, DMSO-$d_6$): 8.59-8.58 (m, 1H), 8.29-8.25 (d, 1H, J=14.28 Hz), 7.91-7.89 (m, 1H), 7.81-7.77 (m, 1H), 7.58-7.56 (m, 1H), 7.49-7.48 (m, 1H), 7.31-7.18 (m, 3H), 7.00-6.97 (d, 1H, J=14.28 Hz), 3.60 (s, 2H), 3.07-3.05 (m, 2H), 2.82-2.80 (m, 2H), 2.49 (s, 3H); cis-2-tert.butyl-5-[2-(pyridin-3-yl)vinyl]-2,3,4,5-tetrahydro-1H-pyrido[4,3-b]indole 1.1(6), LCMS: m/z 332 [M+H]; cis-2-methyl-5-styryl-8-fluoro-2,3,4,5-tetrahydro-1H-pyrido[4,3-b]indole 1.1.1(1), LCMS: m/z 289 [M+H]; trans-2-methyl-5-styryl-8-fluoro-2,3,4,5-tetrahydro-1H-pyrido[4,3-b]indole 1.1.3(1), LC-MS: m/z 289 [M+H]; trans-2-methyl-5-[2-(pyridin-4-yl)vinyl]-8-fluoro-2,3,4,5-tetrahydro-1H-pyrido[4,3-b]indole 1.1.3(2), LC-MS: m/z 290 [M+H], $^1H$ NMR (400 MHz, DMSO-$d_6$): 8.54-8.53 (m, 2H), 8.08-8.04 (d, 1H, J=14.65 Hz), 7.98-7.95 (m, 1H), 7.65-7.63 (m, 2H), 7.29-7.26 (m, 1H), 7.12-7.07 (m, 1H), 6.86-6.82 (d, 1H, J=14.65 Hz), 3.55 (s, 2H), 3.08-3.06 (m, 2H), 2.80-2.78 (m, 2H), 2.48 (s, 3H); cis-2-methyl-5-[2-(pyridin-3-yl)vinyl]-8-fluoro-2,3,4,5-tetrahydro-1H-pyrido[4,3-b]indole 1.1.1(2), LCMS: m/z 290 [M+H], $^1H$ NMR (400 MHz, DMSO-$d_6$): 8.40-8.38 (m, 1H), 8.22-8.21 (m, 1H), 7.27-7.17 (m, 3H), 7.13-7.11 (d, 1H, J=8.43), 7.02-7.98 (m, 1H), 6.90-6.85 (m, 1H), 6.77-6.75 (d, 1H, J=8.43 Hz), 3.57 (s, 2H), 2.69-2.66 (m, 2H), 2.60-2.55 (m, 2H), 2.44 (s, 3H); trans-2-methyl-5-[2-(pyridin-2-yl)vinyl]-8-fluoro-2,3,4,5-tetrahydro-1H-pyrido[4,3-b]indole 1.1.3(3), LCMS: m/z 290 [M+H], NMR (400 MHz, DMSO-$d_6$): 8.59-8.57 (m, 1H), 8.24-8.20 (d, 1H, J=14.65 Hz), 7.92-7.88 (m, 1H), 7.82-7.77 (m, 1H), 7.58-7.56 (m, 1H), 7.30-7.23 (m, 2H), 7.12-7.07 (m, 1H), 7.00-6.96 (d, 1H, J=14.65 Hz), 3.55 (s, 2H), 3.05-3.03 (m, 2H), 2.81-2.78 (m, 2H), 2.48 (s, 3H); cis-2,8-dimethyl-5-styryl-2,3,4,5-tetrahydro-1H-pyrido[4,3-b]indole 1.1.1(3), LCMS: m/z 303 [M+H]; trans-2,8-dimethyl-5-styryl-2,3,4,5-tetrahydro-1H-pyrido[4,3-b]indole 1.1.3(4), LCMS: m/z 303 [M+H]; cis-2,8-dimethyl-5-[2-(pyridin-3-yl)vinyl]-2,3,4,5-tetrahydro-1H-pyrido[4,3-b]indole 1.1.1(4), LCMS: m/z 304 [M+H]; trans-2,8-dimethyl-5-[2-(pyridin-4-yl)vinyl]-2,3,4,5-tetrahydro-1H-pyrido[4,3-b]indole 1.1.3(5), LCMS: m/z 304 [M+H]; cis-2-benzyl-8-methyl-5-[2-(pyridin-2-yl)vinyl]-2,3,4,5-tetrahydro-1H-pyrido[4,3-b]indole 1.1.1(5), LCMS: m/z 380 [M+H]; trans-2-methyl-5-(4-fluorostyryl)-8-fluoro-2,3,4,5-tetrahydro-1H-pyrido[4,3-b]indole 1.1.3(6), LCMS: m/z 325 [M+H]; cis-2-methyl-5-(3-fluorostyryl)-8-fluoro-2,3,4,5-tetrahydro-1H-pyrido[4,3-b]indole 1.1.1(6), LCMS: m/z 325 [M+H]; trans-2,8-dimethyl-5-[4-(trifluoromethyl)styryl]-2,3,4,5-tetrahydro-1H-pyrido[4,3-b]indole 1.1.3(7), LCMS: m/z 371 [M+H]; cis-2,8-dimethyl-5-[3-(trifluoromethyl)styryl]-2,3,4,5-tetrahydro-1H-pyrido[4,3-b]indole 1.1.1(7), LCMS: m/z 371 [M+H]; trans-2-methyl-5-[4-(trifluoromethyl)styryl]-8-fluoro-2,3,4,5-tetrahydro-1H-pyrido[4,3-b]indole 1.1.3(8), LCMS: m/z 375 [M+H]; cis-2-methyl-5-(4-methoxystyryl)-8-fluoro-2,3,4,5-tetrahydro-1H-pyrido[4,3-b]indole 1.1.1(8), LCMS: m/z 337 [M+H]; cis-2-methyl-5-[4-(dimethylamino)styryl]-8-fluoro-2,3,4,5-tetrahydro-1H-pyrido[4,3-b]indole 1.1.1(9), LCMS: m/z 350 [M+H]; trans-2,8-dimethyl-5-(4-fluorostyryl)-2,3,4,5-tetrahydro-1H-pyrido[4,3-b]indole 1.1.3(9), LCMS: m/z 321 [M+H] and others.

EXAMPLE 2

General method for preparation of 5-[2-aryl(or azaheterocyclyl)ethyl]-2,3,4,5-tetrahydro-1H-pyrido[4,3-b]indoles of the general formula 1.2

A. 200 mg of $PtO_2$ is added to a solution of 2 mmol of 5-[2-aryl(or azaheterocyclyl)ethenyl]-2,3,4,5-tetrahydro-1H-pyrido[4,3-b]indole of the general formula 1.1 in 40 ml of ethanol and the resultant mixture is hydrogenated by hydrogen at stirring and room temperature for 24 hs. Upon completion of the reaction (LCMS monitoring) the mixture is filtered or centrifugated. Filtrate is evaporated in vacuo, and the residue is purified by chromatography on silica gel impregnated with triethylamine eluting with $CHCl_3$-hexane-$Et_3N$ mixture (3:6:1) or recrystallized from the proper solvent. 5-[2-Aryl(or azaheterocyclyl)ethyl]-2,3,4,5-tetrahydro-1H-pyrido[4,3-b] indoles of the general formular 1.2 are prepared.

B. A solution of 2,3,4,5-tetrahydro-1H-pyrido[4,3-b]indole 2 (7.5 mmol), 7.5 mmol of tetramethylguanidine and 15.0 mmol of aryl(or azaheterocyclyl)ethylene 4 in 7.5 ml of dimethylsulfoxide is stirred vigorously under argon atmosphere at 90° C. for 12 h. The mixture is diluted with water and extracted with benzene. The extract is washed with 5% $K_2CO_3$ water solution, dried over $Na_2SO_4$ and evaporated in vacuo. Product is washed with the proper solvent, recrystallised from a suitable solvent or purified by chromatography eluting with dichloromethane-THF-triethylamine mixture. 5-[2-Aryl(or azaheterocyclyl)ethyl]-2,3,4,5-tetrahydro-1H-pyrido[4,3-b]indoles of the general formula 1.2. are prepared, among them: 2-methyl-5-(2-phenethyl)-2,3,4,5-tetrahydro-1H-pyrido[4,3-b]indole 1.2(1), LCMS: m/z 291 [M+H]; 2-methyl-5-[2-(pyridin-4-yl)ethyl]-2,3,4,5-tetrahydro-1H-pyrido[4,3-b]indole 1.2(2), LCMS: m/z 292 [M+H]; 2-methyl-5-[2-(pyridin-3-yl)ethyl]-2,3,4,5-tetrahydro-1H-pyrido[4,3-b]indole 1.2(3), LCMS: m/z 292 [M+H]; 2-methyl-5-[2-(pyridin-2-yl)ethyl]-2,3,4,5-tetrahydro-1H-pyrido[4,3-b]indole 1.2(4), LCMS: m/z 292 [M+H]; 2-tert-butyl-5-[2-

(pyridin-3-yl)ethyl]-2,3,4,5-tetrahydro-1H-pyrido[4,3-b]indole 1.2(5), LCMS: m/z 333 [M+H]; 2-methyl-5-[2-(6-methylpyridin-3-yl)ethyl]-2,3,4,5-tetrahydro-1H-pyrido[4,3-b]indole 1.2(6), LCMS: m/z 306 [M+H]; 2,8-dimethyl-5-(2-phenethyl)-2,3,4,5-tetrahydro-1H-pyrido[4,3-b]indole 1.2.1(1), LCMS: m/z 305 [M+H]; 2,8-dimethyl-5-[2-(pyridin-4-yl)ethyl]-2,3,4,5-tetrahydro-1H-pyrido[4,3-b]indole 1.2.1(2), LCMS: m/z 306 [M+H]; 2,8-dimethyl-5-[2-(pyridin-3-yl)ethyl]-2,3,4,5-tetrahydro-1H-pyrido[4,3-b]indole 1.2.1(3), LCMS: m/z 306 [M+H]; 2,8-dimethyl-5-[2-(pyridin-2-yl)ethyl]-2,3,4,5-tetrahydro-1H-pyrido[4,3-b]indole 1.2.1(4), LCMS: m/z 306 [M+H]; 2,8-dimethyl-5-[2-(6-methylpyridin-3-yl)ethyl]-2,3,4,5-tetrahydro-1H-pyrido[4,3-b]indole 1.2.1(5), LCMS: m/z 320 [M+H]; 2,8-dimethyl-5-[2-(pyrazin-2-yl)ethyl]-2,3,4,5-tetrahydro-1H-pyrido[4,3-b]indole 1.2.1(6), LCMS: m/z 305 [M+H]; 2-methyl-5-(2-phenethyl)-8-fluoro-2,3,4,5-tetrahydro-1H-pyrido[4,3-b]indole 1.2.1(7), LCMS: m/z 309 [M+H]; 2-methyl-5-[2-(pyridin-4-yl)ethyl]-8-fluoro-2,3,4,5-tetrahydro-1H-pyrido[4,3-b]indole 1.2.1(8), LCMS: m/z 310 [M+H]; 2-methyl-5-[2-(pyridin-3-yl)ethyl]-8-fluoro-2,3,4,5-tetrahydro-1H-pyrido[4,3-b]indole 1.2.1(9), LCMS: m/z 310 [M+H]; 2-methyl-5-[2-(pyridin-2-yl)ethyl]-8-fluoro-2,3,4,5-tetrahydro-1H-pyrido[4,3-b]indole 1.2.1(10), LCMS: m/z 310 [M+H]; 2-methyl-5-[2-(6-methylpyridin-3-yl)ethyl]-8-fluoro-2,3,4,5-tetrahydro-1H-pyrido[4,3-b]indole 1.2.1(11), LCMS: m/z 324 [M+H]; 2-methyl-5-(2-phenethyl)-8-(trifluoromethyl)-2,3,4,5-tetrahydro-1H-pyrido[4,3-b]indole 1.2.1(12), LCMS: m/z 309 [M+H]; 2-methyl-5-[2-(pyridin-3-yl)ethyl]-8-(trifluoromethyl)-2,3,4,5-tetrahydro-1H-pyrido[4,3-b]indole 1.2.1(13), LCMS: m/z 310 [M+H]; 2-methyl-5-(2-phenethyl)-6-fluoro-2,3,4,5-tetrahydro-1H-pyrido[4,3-b]indole 1.2.2(1), LCMS: m/z 310 [M+H]; 2-methyl-5-(2-phenethyl)-6-(trifluoromethyl)-2,3,4,5-tetrahydro-1H-pyrido[4,3-b]indole 1.2.2(2), LCMS: m/z 310 [M+H]; 2-methyl-5-[2-(pyridin-3-yl)ethyl]-6-(trifluoromethyl)-2,3,4,5-tetrahydro-1H-pyrido[4,3-b]indole 1.2.2(3), LCMS: m/z 324 [M+H] and others.

EXAMPLE 3

General method for preparation of 5-[2-aryl(or azaheterocyclyl)ethynyl]-2,3,4,5-tetrahydro-1H-pyrido[4,3-b]indoles of the general formula 1.3

50 mg (0.2 mmol) of CuSO4×5H2O, 74 mg (0.4 mmol) of 1,10-phenanthroline, 890 mg of dry powdered $K_3PO_4$ and 2.2 mmol of halogen acetylene 5 is added consecutively to a solution of 2 mmol of ,3,4,5-tetrahydro-1H-pyrido[4,3-b]indole 2 in 3 ml of toluene under argon atmosphere. The mixture is stirred at temperature 80-85° C. for 12 hr. Monitoring of the reaction was carried out by means of LCMS. Upon completion of the reaction the mixture is diluted with ether and filtered. The solvent is evaporated, the residue is purified by chromatography on silica gel impregnated with triethylamine eluting with hexane-chloroform-Et3N mixture (6:3:1). 5-[2-Aryl(or azaheterocyclyl)ethynyl]-2,3,4,5-tetrahydro-1H-pyrido[4,3-b]indoles 1.3 are prepared, among them: 2-methyl-5-(phenylethynyl)-2,3,4,5-tetrahydro-1H-pyrido[4,3-b]indole 1.3(1), LCMS: m/z 287 [M+H], $^1$H NMR (400 MHz, DMSO-$d_6$): 7.65-7.63 (m, 3H), 7.52-7.44 (m, 4H), 7.32-7.30 (m, 1H), 7.26-7.23 (m, 1H), 3.57 (br. s, 2H), 2.93-2.91 (m, 2H), 2.83-2.81 (m, 2H), 2.48 (s, 3H); 2-methyl-5-(pyridin-2-ylethynyl)-2,3,4,5-tetrahydro-1H-pyrido[4,3-b]indole 1.3(2), LCMS: m/z 288 [M+H]; 2-methyl-5-(pyridin-3-ylethynyl)-2,3,4,5-tetrahydro-1H-pyrido[4,3-b]indole 1.3(3), LCMS: m/z 288 [M+H]; 2-methyl-5-(pyridin-4-ylethynyl)-2,3,4,5-tetrahydro-1H-pyrido[4,3-b]indole 13(4), LCMS: m/z 288 [M+H]; 2-methyl-5-(pyrimidin-5-ylethynyl)-2,3,4,5-tetrahydro-1H-pyrido[4,3-b]indole 1.3(5), LCMS: m/z 289 [M+H]; 2-methyl-5-(phenylethynyl)-8-fluoro-2,3,4,5-tetrahydro-1H-pyrido[4,3-b]indole 1.3.1(1), LC-MS: m/z 305 [M+H], $^1$H NMR (400 MHz, DMSO-$d_6$): 7.65-7.61 (m, 3H), 7.50-7.45 (m, 3H), 7.35-7.32 (m, 1H), 7.17-7.12 (m, 1H), 3.54 (br. s, 2H), 2.93-2.91 (m, 2H), 2.83-2.81 (m, 2H), 2.48 (s, 3H); 2-methyl-5-(pyridin-2-ylethynyl)-8-fluoro-2,3,4,5-tetrahydro-1H-pyrido[4,3-b]indole 1.3.1(2), LCMS: m/z 306 [M+H]; 2-methyl-5-(pyridin-3-ylethynyl)-8-fluoro-2,3,4,5-tetrahydro-1H-pyrido[4,3-b]indole 1.3.1(3), LCMS: m/z 306 [M+H], $^1$H NMR (400 MHz, DMSO-$d_6$): 8.85-8.84 (m, 1H), 8.62-8.60 (m, 1H), 8.06-8.03 (m, 1H), 7.69-7.66 (m, 1H), 7.52-7.49 (m, 1H), 7.36-7.33 (m, 1H), 7.18-7.13 (m, 1H), 3.53 (s, 2H), 2.94-2.92 (m, 2H), 2.81-2.80 (m, 2H), 2.48 (s, 3H); 2-methyl-5-(pyridin-4-ylethynyl)-8-fluoro-2,3,4,5-tetrahydro-1H-pyrido[4,3-b]indole 1.3.1(4), LCMS: m/z 306 [M+H]; 2-methyl-5-(pyridin-3-ylethynyl)-6-fluoro-2,3,4,5-tetrahydro-1H-pyrido[4,3-b]-indole 1.3.2(1), LCMS: m/z 306 [M+H]; 2,8-dimethyl-5-(phenylethynyl)-2,3,4,5-tetrahydro-1H-pyrido[4,3-b]indole 1.3.1(5), LCMS: m/z 301 [M+H]; 2,8-dimethyl-5-(pyridin-2-ylethynyl)-2,3,4,5-tetrahydro-1H-pyrido[4,3-b]indole 1.3.1(6), LCMS: m/z 302 [M+H]; 2,8-dimethyl-5-(pyridin-3-ylethynyl)-2,3,4,5-tetrahydro-1H-pyrido[4,3-b]indole 1.3.1(7), LCMS: m/z 302 [M+H]; 2,8-dim ethyl-5-(pyridin-4-ylethynyl)-2,3,4,5-tetrahydro-1H-pyrido[4,3-b]indole 1.3.1(8), LCMS: m/z 302 [M+H]; 2-methyl-5-(pyridin-3-ylethynyl)-8-(trifluoromethyl)-2,3,4,5-tetrahydro-1H-pyrido[4,3-b]indole 1.3.1(9), LCMS: m/z 352 [M+H]; 2-methyl-5-[(4-methoxyphenyl)ethynyl]-8-fluoro-2,3,4,5-tetrahydro-1H-pyrido[4,3-b]indole 1.3.1(10), LCMS: m/z 335 [M+H]; 2-methyl-5-[(4-fluorophenyl)ethynyl]-8-fluoro-2,3,4,5-tetrahydro-1H-pyrido[4,3-b]indole 1.3.1(11), LCMS: m/z 323 [M+H]; 2-methyl-5-[(3-fluorophenyl)ethynyl]-8-fluoro-2,3,4,5-tetrahydro-1H-pyrido[4,3-b]indole 1.3.1(12), LCMS: m/z 323 [M+H]; 2-methyl-5-(4-trifluoromethylphenylethynyl)-8-fluoro-2,3,4,5-tetrahydro-1H-pyrido[4,3-b]indole 1.3.1(13), LCMS: m/z 373 [M+H]; 2-methyl-5-(pyridin-3-ylethynyl)-8-trifluoromethyl-2,3,4,5-tetrahydro-1H-pyrido[4,3-b]indole 1.3.2(14), LCMS: m/z 356 [M+H]; 2,8-dimethyl-5-[(4-fluorophenyl)ethynyl]-2,3,4,5-tetrahydro-1H-pyrido[4,3-b]indole 1.3.1(15), LCMS: m/z 319 [M+H]; 2,8-dimethyl-5-[(3-fluorophenyl)ethynyl]-2,3,4,5-tetrahydro-1H-pyrido[4,3-b]indole 1.3.1(16), LCMS: m/z 319 [M+H]; 2,8-dimethyl-5-[((4-trifluoromethyl)phenyl)ethynyl]-2,3,4,5-tetrahydro-1H-pyrido[4,3-b]indole 1.3.1(17), LCMS: m/z 369 [M+H]; 2,8-dimethyl-5-[((3-trifluoromethyl)phenyl)ethynyl]-2,3,4,5-tetrahydro-1H-pyrido[4,3-b]indole 1.3.1(18), LCMS: m/z 369 [M+H]; 2,8-dimethyl-5-[((2-trifluoromethyl)phenyl)ethynyl]-2,3,4,5-tetrahydro-1H-pyrido[4,3-b]indole 1.3.1(19), LCMS: m/z 369 [M+H]; 2,8-dimethyl-5-[(2-fluorophenyl)ethynyl]-2,3,4,5-tetrahydro-1H-pyrido[4,3-b]indole 1.3.1(20), LCMS: m/z 319 [M+H]; 2,8-dimethyl-5-[(4-methoxyphenyl)ethynyl]-2,3,4,5-tetrahydro-1H-pyrido[4,3-b]indole 13.1(21), LCMS: m/z 331 [M+H]; 2,8-dimethyl-5-[((4-dimethylamino)phenyl)ethynyl]-2,3,4,5-tetrahydro-1H-pyrido[4,3-b]indole 1.3.1(22), LCMS: m/z 344 [M+H]; 2,8-dimethyl-5-[(3-methoxyphenyl)ethynyl]-2,3,4,5-tetrahydro-1H-pyrido[4,3-b]indole 1.3.1(23), LCMS: m/z 331 [M+H]; 2,8-dimethyl-5-[(2-methoxyphenyl)ethynyl]-2,3,4,5-tetrahydro-1H-pyrido[4,3-b]indole 1.3.1(24), LCMS: m/z 331 [M+H] and others.

EXAMPLE 4

General method for preparation of 2,3,4,5-tetrahydro-1H-pyrido[4,3-b]indoles of the general formulas 1.1, 1.2 in the form of salts. To a solution of 1 mmol of 2,3,4,5-tetrahydro-1H-pyrido[4,3-b]indole of the general formulas 1.1 or 1.2 in ether, dioxane or methanol 0.76 ml (2.1 mmol) of dioxane or methanol solution of HCl or HBr is added. The precipitated white solid is separated, washed with acetone and/or ether, dried in vacuo. It gives 2,3,4,5-tetrahydro-1H-pyrido[4,3-b] indoles of the general formulas 1.1, 1.2 in the form of salts, among them: cis-2-methyl-5-styryl-2,3,4,5-tetrahydro-1H-pyrido[4,3-b]indole hydrochloride 1.1(1)HCl, LCMS: m/z 289 [M+H]; trans-2-methyl-5-styryl-2,3,4,5-tetrahydro-1H-pyrido[4,3-b]indole hydrochloride 1.1(2)HCl, LCMS: m/z 289 [M+H]; trans-2-methyl-5-[2-(pyridin-4-yl)vinyl]-2,3,4,5-tetrahydro-1H-pyrido[4,3-b]indole hydrochloride 1.1(3)HCl, LCMS: m/z 290 [M+H]; cis-2-methyl-5-[2-(pyridin-3-yl)vinyl]-2,3,4,5-tetrahydro-1H-pyrido[4,3-b]indole hydrochloride 1.1(4)HCl, LCMS: m/z 290 [M+H]; trans-2-methyl-5-[2-(pyridin-2-yl)vinyl]-2,3,4,5-tetrahydro-1H-pyrido[4,3-b]indole hydrochloride 1.1(5)HCl, LCMS: m/z 290 [M+H]; cis-2-tert-butyl-5-[2-(pyridin-3-yl)vinyl]-2,3,4,5-tetrahydro-1H-pyrido[4,3-b]indole hydrochloride 1.1(6)HCl, LCMS: m/z 332 [M+H]; cis-2-methyl-5-styryl-8-fluoro-2,3,4,5-tetrahydro-1H-pyrido[4,3-b]indole hydrochloride 1.1.1(1)HCl, LCMS: m/z 289 [M+H]; trans-2-methyl-5-styryl-8-fluoro-2,3,4,5-tetrahydro-1H-pyrido[4,3-b] indole hydrochloride 1.1.3(1)HCl, LCMS: m/z 289 [M+H]; trans-2-methyl-5-[2-(pyridin-4-yl)vinyl]-8-fluoro-2,3,4,5-tetrahydro-1H-pyrido[4,3-b]indole hydrochloride 1.1.3(2)HCl, LCMS: m/z 290 [M+H]; cis-2-methyl-5-[2-(pyridin-3-yl)vinyl]-8-fluoro-2,3,4,5-tetrahydro-1H-pyrido[4,3-b]indole hydrochloride 1.1.1(2)HCl, LCMS: m/z 290 [M+H]; trans-2-methyl-5-[2-(pyridin-2-yl)vinyl]-8-fluoro-2,3,4,5-tetrahydro-1H-pyrido[4,3-b]indole hydrochloride 1.1.3(3)HCl, LCMS: m/z 290 [M+H]; cis-2,8-dimethyl-5-styryl-2,3,4,5-tetrahydro-1H-pyrido[4,3-b]indole hydrochloride 1.1.1(3)HCl, LCMS: m/z 303 [M+H]; trans-2,8-dimethyl-5-styryl-2,3,4,5-tetrahydro-1H-pyrido[4,3-b] indole hydrochloride 1.1.3(4)HCl, LCMS: m/z 303 [M+H]; cis-2,8-dimethyl-5-[2-(pyridin-3-yl)vinyl]-2,3,4,5-tetrahydro-1H-pyrido[4,3-b]indole hydrochloride 1.1.1(4)HCl, LCMS: m/z 304 [M+H]; trans-2,8-dimethyl-5-[2-(pyridin-4-yl)vinyl]-2,3,4,5-tetrahydro-1H-pyrido[4,3-b]indole hydrochloride 1.1.3(5)HCl, LCMS: m/z 304 [M+H]; trans-2-methyl-5-(4-fluorostyryl)-8-fluoro-2,3,4,5-tetrahydro-1H-pyrido[4,3-b]indole hydrochloride 1.1.3(6)HCl, LCMS: m/z 325 [M+H]; cis-2-methyl-5-(3-fluorostyryl)-8-fluoro-2,3,4,5-tetrahydro-1H-pyrido[4,3-b]indole hydrochloride 1.1.1(6) HCl, LCMS: m/z 325 [M+H]; trans-2,8-dimethyl-5-[(4-trifluoromethyl)styryl]-2,3,4,5-tetrahydro-1H-pyrido[4,3-b] indole hydrochloride 1.1.3(7)HCl, LCMS: m/z 371 [M+H]; cis-2,8-dimethyl-5-[(3-trifluoromethyl)styryl]-2,3,4,5-tetrahydro-1H-pyrido[4,3-b]indole hydrochloride 1.1.1(7)HCl, LCMS: m/z 371 [M+H]; trans-2-methyl-5-[(4-trifluoromethyl)styryl]-8-fluoro-2,3,4,5-tetrahydro-1H-pyrido[4,3-b] indole hydrochloride 1.1.3(8)HCl, LCMS: m/z 375 [M+H]; cis-2-methyl-5-(4-methoxystyryl)-8-fluoro-2,3,4,5-tetahydro-1H-pyrido[4,3-b]indole hydrochloride 1.1.1(8)HCl, LCMS: m/z 337 [M+H]; cis-2-methyl-5-[(4-dimethylamino) styryl]-8-fluoro-2,3,4,5-tetrahydro-1H-pyrido[4,3-b]indole hydrochloride 1.1.1(9)HCl, LCMS: m/z 350 [M+H]; trans-2,8-dimethyl-5-(4-fluorostyryl)-2,3,4,5-tetrahydro-1H-pyrido[4,3-b]indole hydrochloride 1.1.3(9)HCl, LCMS: m/z 321 [M+H]; 2-methyl-5-(2-phenethyl)-2,3,4,5-tetrahydro-1H-pyrido[4,3-b]indole hydrochloride 1.2(1)HCl, LCMS: m/z 291 [M+H]; 2-methyl-5-(2-phenethyl)-2,3,4,5-tetrahydro-1H-pyrido[4,3-b]indole hydrobromide 1.2(1)HBr, LCMS: m/z 291 [M+H]; 2-methyl-5-[2-(pyridin-4-yl)ethyl]-2,3,4,5-tetrahydro-1H-pyrido[4,3-b]indole hydrochloride 1.2(2)HCl, LCMS: m/z 292 [M+H]; 2-methyl-5-[2-(pyridin-3-yl)ethyl]-2,3,4,5-tetrahydro-1H-pyrido[4,3-b]indole hydrochloride 1.2(3)HCl, LCMS: m/z 292 [M+H]; 2-methyl-5-[2-(pyridin-2-yl)ethyl]-2,3,4,5-tetrahydro-1H-pyrido[4,3-b]indole hydrochloride 1.2(4)HCl, LCMS: m/z 292 [M+H]; 2-methyl-5-[2-(6-methylpyridin-3-yl)ethyl]-2,3,4,5-tetrahydro-1H-pyrido[4,3-b]indole hydrochloride 1.2(6)HCl, LCMS: m/z 306 [M+H]; 2,8-dimethyl-5-(2-phenethyl)-2,3,4,5-tetrahydro-1H-pyrido[4,3-b]indole hydrochloride 1.2.1(1)HCl, LCMS: m/z 305 [M+H]; 2,8-dimethyl-5-(2-phenethyl)-2,3,4,5-tetrahydro-1H-pyrido[4,3-b]indole hydrobromide 1.2.1(1)HBr, LCMS: m/z 305 [M+H]; 2,8-dimethyl-5-[2-(pyridin-4-yl)ethyl]-2,3,4,5-tetrahydro-1H-pyrido[4,3-b]indole hydrochloride 1.2.1(2)HCl, LCMS: m/z 306 [M+H]; 2,8-dimethyl-5-[2-(pyridin-3-yl)ethyl]-2,3,4,5-tetrahydro-1H-pyrido[4,3-b]indole hydrochloride. 1.2.1(3)HCl, LCMS: m/z 306 [M+H]; 2,8-dimethyl-5-[2-(pyridin-2-yl)ethyl]-2,3,4,5-tetrahydro-1H-pyrido[4,3-b]indole hydrochloride 1.2.1(4)HCl, LCMS: m/z 306 [M+H]; 2,8-dimethyl-5-[2-(6-methylpyridin-3-yl)ethyl]-2,3,4,5-tetrahydro-1H-pyrido[4,3-b]indole hydrochloride 1.2.1(5)HCl, LCMS: m/z 320 [M+H]; 2,8-dimethyl-5-[2-(pyrazin-2-yl) ethyl]-2,3,4,5-tetrahydro-1H-pyrido[4,3-b]indole hydrochloride 1.2.1(6)HCl, LCMS: m/z 305 [M+H]; 2-methyl-5-(2-phenethyl)-8-fluoro-2,3,4,5-tetrahydro-1H-pyrido[4,3-b] indole hydrochloride 1.2.1(7)HCl, LCMS: m/z 309 [M+H]; 2-methyl-5-(2-phenethyl)-8-fluoro-2,3,4,5-tetrahydro-1H-pyrido[4,3-b]indole hydrobromide 1.2.1(7)HBr, LCMS: m/z 309 [M+H]; 2-methyl-5-[2-(pyridin-4-yl)ethyl]-8-fluoro-2, 3,4,5-tetrahydro-1H-pyrido[4,3-b]indole hydrochloride 1.2.1(8)HCl, LCMS: m/z 310 [M+H]; 2-methyl-5-[2-(pyridin-3-yl)ethyl]-8-fluoro-2,3,4,5-tetrahydro-1H-pyrido[4,3-b]indole hydrochloride 1.2.1(9)HCl, LCMS: m/z 310 [M+H]; 2-methyl-5-[2-(pyridin-2-yl)ethyl]-8-fluoro-2,3,4, 5-tetrahydro-1H-pyrido[4,3-b]indole hydrochloride 1.2.1(10)HCl, LCMS: m/z 310 [M+H]; 2-methyl-5-[2-(6-methylpyridin-3-yl)ethyl]-8-fluoro-2,3,4,5-tetrahydro-1H-pyrido[4,3-b]indole hydrochloride 1.2.1(11)HCl, LCMS: m/z 324 [M+H]; 2-methyl-5-(2-phenethyl)-8-(trifluoromethyl)-2,3,4,5-tetrahydro-1H-pyrido[4,3-b]indole hydrochloride 1.2.1(12)HCl, LCMS: m/z 309 [M+H] and others.

EXAMPLE 5

The biological activity test of the compounds of the general formula 1. The compounds of the general formula 1 were tested as potential antagonists of H1 histamine receptor and as regulators of calcium $Ca^{+2}$ ions cytosolic concentration in the cells by means of blocking the calcium canals regulated by the intracellular calcium depot. SK-N-SH Cells (ATCC, USA) were grown in DMEM medium (Invitrogen, USA) containing 10% fetal calf serum (FBS) and Penicillin-Streptomycin antibiotics, in $CO_2$ incubator (5% $CO_2$) until getting the cell density $1*10^5$ cells/cm$^2$. The cells were removed from the surface of the flask with TrypLE Express reagent (Invitrogen, USA), then collected by means of centrifugation and resuspended in Hybridoma Serum Free Medium (HSFM, Sigma, USA) providing the concentration of $4*10^6$ cells/ml. For measuring the intracellular concentration of calcium the cells were loaded with the calcium-sensitive fluorescent dye Fura 2 AM (Invitrogen, USA) by incubating their suspension with the dye for 30 minutes at room temperature. Again, the cells were collected by centrifugation, resuspended in HSFM; incubated for 15 minutes, recollected by centrifugation, washed twice with HSFM and resuspended in HSFM setting up the concentration $4*10^6$ cells/ml. The cells were diluted with an operating buffer (NaCl 0.145 M, KCl 0.0054 M, $NaH_2PO_4$ 0.001 M, $MgSO_4$ 0.0008 M, $CaCl_2$ 0.0018 M, HEPES 0.03 M, D-glucose 0.0112 M pH 7.4) to the concentration of 1*10⁵ cells/ml in a measuring cell with a magnet stirrer, after that the fluorescence registration was carried out in the mode of two-wavelength excitement (340 and 380 nm, respectively) with an emission wavelength of 510 nm (F1 and F2, respectively). In 20 seconds after the beginning of registration, 10 mM of histamine water solution was added (a final concentration is 10 μM). After the intracellular concentration of calcium had reached its maximum, in another 30 seconds, DMSO solution of the tested compound was added, and registration was continued for additional 3 minutes. In order to estimate the biological activity of the compounds, their serial DMSO dilutions were prepared and the correlation between the influence of the compound on the histamine induced calcium stream and its concentration was determined. The transforming fluorescent signal into calcium concentration was carried out by means of the equation built in the program Super Ion Probe (Shimadzu) software. For this purpose the maximum concentration of free calcium was determined by adding 0.1 mg/ml of digitonine (Sigma, USA) up to 0.1 mg/ml, while the zero calcium concentration—by adding of ethylene-diamin-tetraacetate (EDTA) up to 10 mM. Kinetic curves of lowering intracellular calcium concentration after the addition of the tested compound in the presence of histamine were calculated with a single-phase exponential model using the Prism 4 software (GraphPad Software, Inc.):

$$[Ca]=[Ca]_{max}*\exp(-K*T)+[Ca]_{min}$$

where T is the time after the tested compound was added, $[Ca]_{max}$ and $[Ca]_{min}$ are the maximum (the peak value after the addition of histamine) and the minimum (the equilibrium level the curve approached after the addition of the tested compound) concentrations of intracellular calcium, K is the rate constant of intracellular calcium concentration lowering calculated by minimization of least square deviations.

The calculated rate constants of calcium concentration lowering (K) were used to determine their dependence on the tested compound concentration (C); and by means of the program Prism 4 using this dependence the values of $EC_{50}$ (the concentration of the tested compound corresponding to half-maximum increasing of the rate constant of intracellular calcium concentration lowering) were determined by virtue of four parameter equation $$K = K_{Bkg} + \frac{K_{max}C^N}{EC_{50}^N + C^N},$$

where $K_{Bkg}$ and $K_{max}$ are the rate constants of calcium concentration lowering without and in the presence of infinitely large concentration of the tested compound, respectively; N is Hill's coefficient. Below table 3 presents the $EC_{50}$ values for some of the tested compounds of the general formula 1.

TABLE 3

Biological activity of antagonists of serotonin 5-HT₆ receptors and regulators of homeostasis of calcium ions of the general formula 1.

| No comp. | Fomula | EC50, μM (Phase 1) | EC50, μM (Phase 2) |
|---|---|---|---|
| 1.2.1(5)HCl Dimebon | 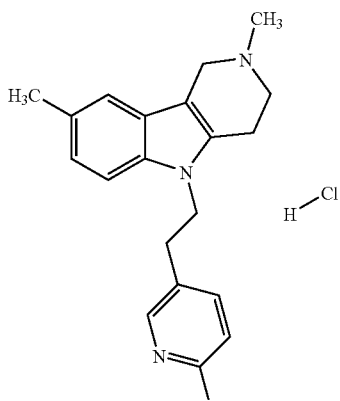 | 0.16 | 1.58 |
| 1.1(1) | 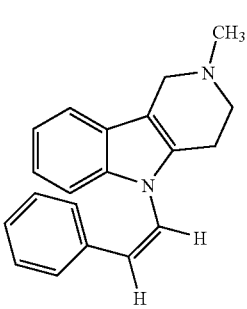 [SMILES: CN1CCc2c(c3ccccc3n2/C=C\c2ccccc2)C1] | 0.03 | 0.18 |

TABLE 3-continued
Biological activity of antagonists of serotonin 5-HT$_6$ receptors and regulators of homeostasis of calcium ions of the general formula 1.
| No comp. | Fomula | EC50, μM (Phase 1) | EC50, μM (Phase 2) |
|---|---|---|---|
| 1.1(2) | 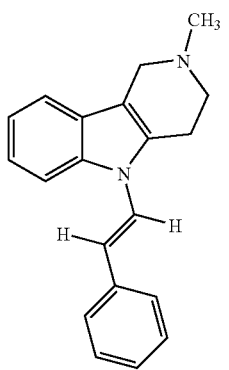 [SMILES: CN1CCc2c(c3ccccc3n2/C=C/c2ccccc2)C1] | 0.35 | 2.13 |
| 1.1(3) | 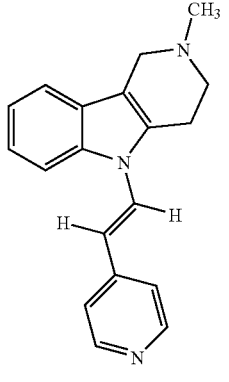 [SMILES: CN1CCc2c(c3ccccc3n2/C=C/c2ccncc2)C1] | >10 | >10 |
| 1.1(4) | 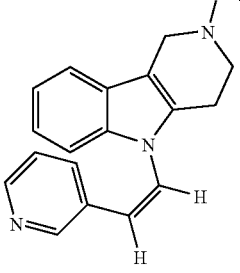 | >10 | >10 |
| 1.1(5) | 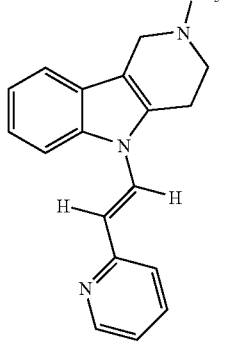 | >10 | >10 |

TABLE 3-continued

Biological activity of antagonists of serotonin 5-HT$_6$ receptors and regulators of homeostasis of calcium ions of the general formula 1.

| No comp. | Fomula | EC50, μM (Phase 1) | EC50, μM (Phase 2) |
|---|---|---|---|
| 1.1.1(1) | [structure] | 0.02 | 0.15 |
| 1.1.1(2) | [structure] | >10 | >10 |
| 1.1.1(3) | [structure] | 0.07 | 0.154 |
| 1.1.1(6) | [structure] | 0.035 | 0.19 |
| 1.2(2)HCl | [structure] | 0.12 | 0.5 |

TABLE 3-continued
Biological activity of antagonists of serotonin 5-HT$_6$ receptors and regulators of homeostasis of calcium ions of the general formula 1.
| No comp. | Fomula | EC50, μM (Phase 1) | EC50, μM (Phase 2) |
|---|---|---|---|
| 1.2(3)HCl | 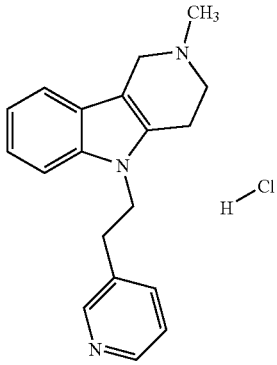 [SMILES: CN1CCc2c(c3ccccc3n2CCc2cccnc2)C1 ; Cl] | 0.10 | 0.412 |
| 1.2(4)HCl | 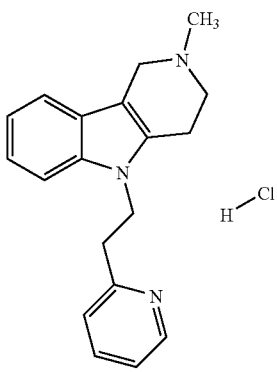 [SMILES: CN1CCc2c(c3ccccc3n2CCc2ccccn2)C1 ; Cl] | 1.82 | 0.93 |
| 1.2.1(1)HCl | 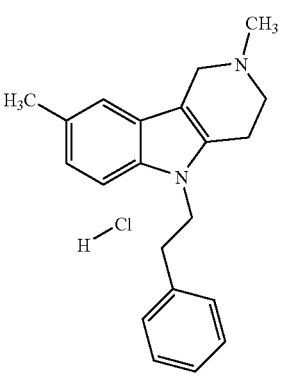 | 0.04 | 0.15 |
| 1.2.1(2)HCl | 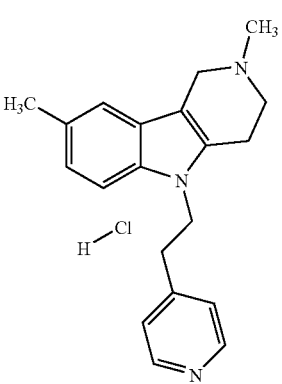 | 0.16 | 3.98 |

TABLE 3-continued
Biological activity of antagonists of serotonin 5-HT$_6$ receptors and regulators of homeostasis of calcium ions of the general formula 1.
| No comp. | Fomula | EC50, μM (Phase 1) | EC50, μM (Phase 2) |
|---|---|---|---|
| 1.2.1(3)HCl | 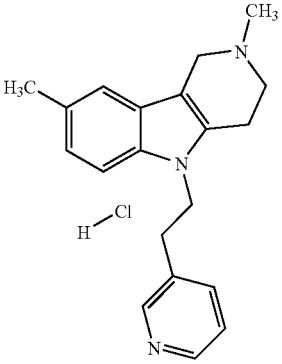 | 0.083 | 0.579 |
| 1.2.1(4)HCl | 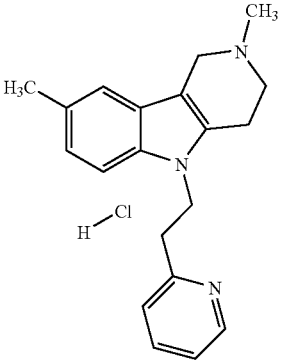 | 0.5 | 10 |
| 1.2.1(6) | 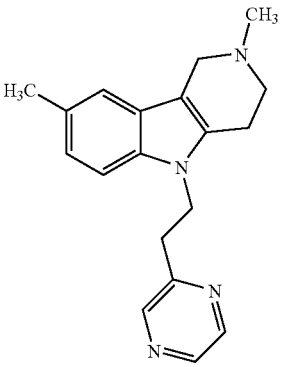 [SMILES: Cc1ccc2c(c1)c1c(n2CCc2cnccn2)CCN(C)C1] | 0.32 | 7.94 |
| 1.2.1(7)HCl | 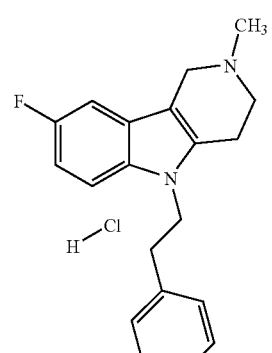 | 0.04 | 0.13 |

TABLE 3-continued
Biological activity of antagonists of serotonin 5-HT$_6$ receptors and regulators of homeostasis of calcium ions of the general formula 1.
| No comp. | Fomula | EC50, µM (Phase 1) | EC50, µM (Phase 2) |
|---|---|---|---|
| 1.2.1(8)HCl | 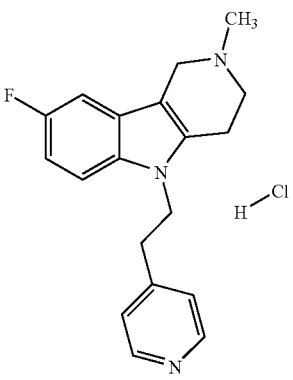 [SMILES: CN1CCc2c(c3cc(F)ccc3n2CCc2ccncc2)C1 ; Cl] | 0.12 | 0.47 |
| 1.2.1(9)HCl | 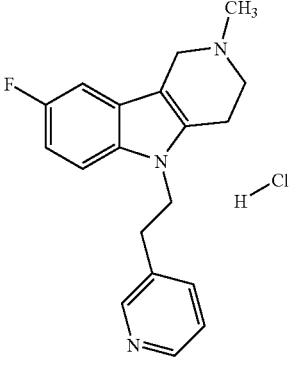 [SMILES: CN1CCc2c(c3cc(F)ccc3n2CCc2cccnc2)C1 ; Cl] | 0.09 | 0.297 |
| 1.2.1(10)HCl | 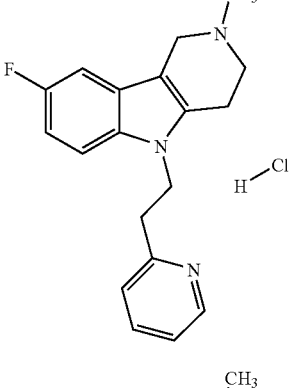 | 0.94 | 0.61 |
| 1.2.1(11)HCl | 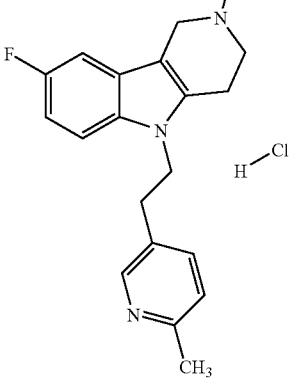 | 0.113 | 0.73 |

TABLE 3-continued
Biological activity of antagonists of serotonin 5-HT$_6$ receptors and regulators of homeostasis of calcium ions of the general formula 1.
| No comp. | Fomula | EC50, µM (Phase 1) | EC50, µM (Phase 2) |
|---|---|---|---|
| 1.2.2(1)HCl | 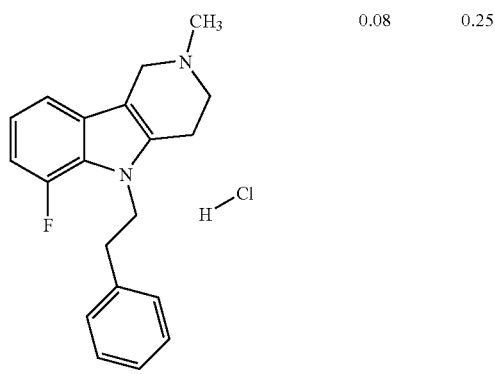 | 0.08 | 0.25 |
| 1.3(1) | 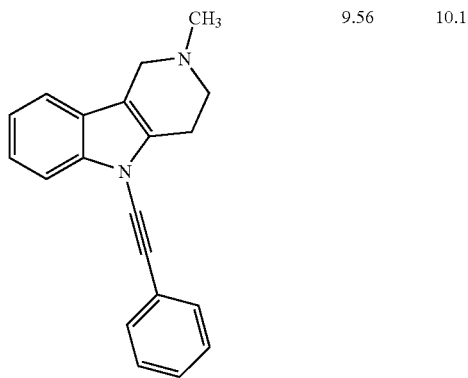 | 9.56 | 10.1 |
| 1.3(3) | 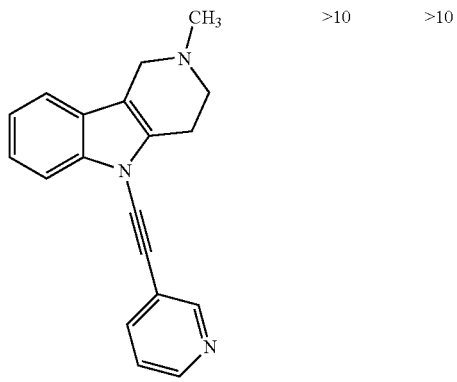 | >10 | >10 |
| 1.3.1(1) | 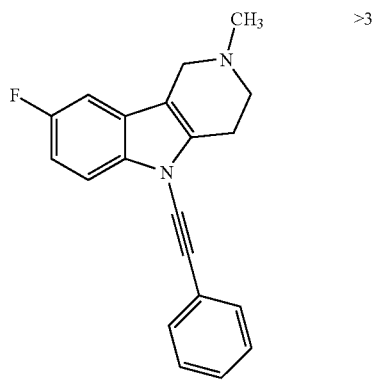 | >3 | |

TABLE 3-continued

Biological activity of antagonists of serotonin 5-HT$_6$ receptors and regulators of homeostasis of calcium ions of the general formula 1.

| No comp. | Fomula | EC50, μM (Phase 1) | EC50, μM (Phase 2) |
|---|---|---|---|
| 1.3.1(3) | 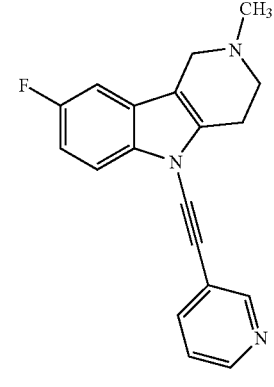 [SMILES: CN1CCc2c(c3cc(F)ccc3n2C#Cc2cccnc2)C1] | >10 | >10 |
| 1.3.1(5) | 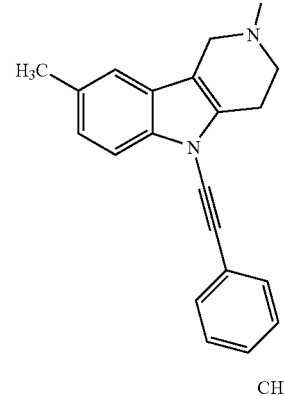 | >10 | >10 |
| 1.3.1(7) | 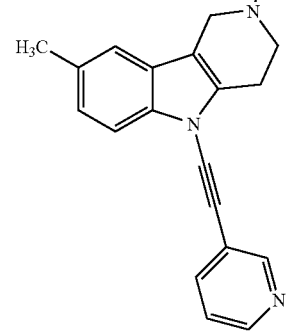 | >10 | >10 |

As can be seen from table 3 compounds of the general formula 1 are effective blockers of the histamine receptor (Phase 1; the compounds block calcium ions from entering the cells as a result of their antagonistic action on H1-receptors), and facilitate the removing of intraplasmatic calcium (Phase 2), which is indicative of their anti-histamine (EC$_{50}$, μM (Phase 1)), neuroprotective and cognitive-stimulating effects (EC$_{50}$, μM (Фа3а 2)).

EXAMPLE 6

The biological activity test of the compounds of the general formula 1. Compounds of the general formula 1 were tested for their ability to prevent the activation of 5-HT$_6$ receptors by serotonin. The cells HEK 293 (kidney cells of a human embryon) with an artificially expressed 5-HT$_6$ receptor, activation of which with serotonin results in intracellular cAMP increasing, were used. The concentration of intracellular cAMP was determined using a LANCE cAMP reagent (PerkinElmer) by the method described by the manufacturer: [http://las.perkinelmer.com/content/Manuals/MAN_LANCEcAMP384KitUser.pdf].

The effectiveness of the compounds was estimated on the basis of their ability to reduce the concentration of intracellular cAMP induced by serotonin, FIG. 1. IC50 values for some of the compounds of the general formula 1 are represented in table 4

TABLE 4
The ability of the compounds of the general formula 1 to prevent the activation of 5-HT$_6$ receptors by serotonin.
| No comp. | Formula | IC$_{50}$, μM |
|---|---|---|
| 1.1(1) | 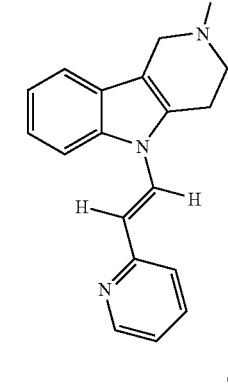 | 7.2 |
| 1.1(2) | | 3.79 |
| 1.1(3) | | 26.7 |
| 1.1(4) | | >30 |
| 1.1(5) | 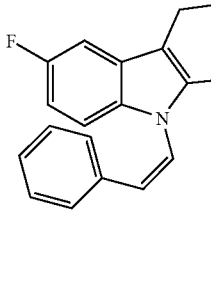 | 45.9 |
| 1.1.1(1) | 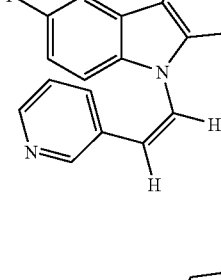 | 14.6 |
| 1.1.1(2) | | >30 |
| 1.1.1(3) | 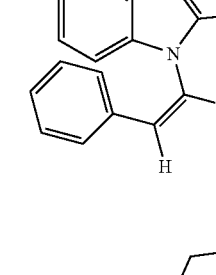 | 0.172 |
| 1.1.1(4) | 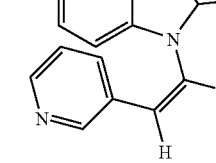 | 2.13 |

TABLE 4-continued

The ability of the compounds of the general formula 1 to prevent the activation of 5-HT$_6$ receptors by serotonin.

| No comp. | Formula | IC$_{50}$, μM |
|---|---|---|
| 1.1.3(1) | [structure: 8-fluoro-2-methyl-tetrahydro-β-carboline N-styryl] | 4.94 |
| 1.1.3(2) | [structure: 8-fluoro-2-methyl-tetrahydro-β-carboline with N-(2-(pyridin-4-yl)vinyl)] | 6.16 |
| 1.1.3(3) | [structure: 8-fluoro-2-methyl-tetrahydro-β-carboline with N-(2-(pyridin-2-yl)vinyl)] | 25.3 |
| 1.1.3(4) | [structure: 8-methyl-2-methyl-tetrahydro-β-carboline N-styryl] | 4.84 |
| 1.1.3(5) | [structure: 8-methyl-2-methyl-tetrahydro-β-carboline with N-(2-(pyridin-4-yl)vinyl)] | >30 |
| 1.2(1)HCl | [structure: 2-methyl-tetrahydro-β-carboline N-(2-phenylethyl) HCl] | 1.10 |
| 1.2.1(1)HCl | [structure: 8-methyl-2-methyl-tetrahydro-β-carboline N-(2-phenylethyl) HCl] | 0.303 |
| 1.2.1(2)HCl | [structure: 8-methyl-2-methyl-tetrahydro-β-carboline N-(2-(pyridin-4-yl)ethyl) HCl] | 0.43 |

TABLE 4-continued

The ability of the compounds of the general formula 1 to prevent the activation of 5-HT$_6$ receptors by serotonin.

| No comp. | Formula | IC$_{50}$, μM |
|---|---|---|
| 1.2.1(3)HCl | | 1.15 |
| 1.2.1(7)HCl | | 1.99 |
| 1.2.1(8)HCl | | 12.0 |
| 1.2.1(10)HCl | | 24.8 |
| 1.2.1(11)HCl | | 51.6 |
| 1.2.1(5)HCl Dimebone | | 4.4 |
| 1.3(3) | | >30 |

TABLE 4-continued

The ability of the compounds of the general formula 1
to prevent the activation of 5-HT$_6$ receptors by serotonin.

| No comp. | Formula | IC$_{50}$, µM |
|---|---|---|
| 1.3.1(1) | | 5.77 |
| 1.3.1(3) | | >30 |
| 1.3.1(5) | | 8.71 |
| 1.3.1(7) | 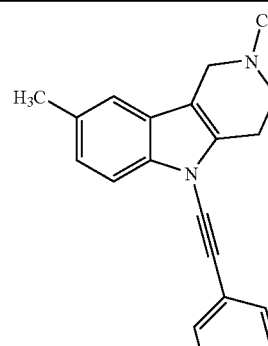 | >30 |

As can be seen from table 4 the compounds of the general formula 1 are effective antagonists of 5-HT6 serotonin receptors that proves the possibility of their use for treatment of Alzheimer's disease and other cognitive disorders.

EXAMPLE 7

The nootropic action (memory enhancement disturbed by scopolamine) of antagonists of 5-HT$_6$ receptors of the formulas 1.2.1(2)HCl, 1.2.1(4)HCl and 1.2.1(5)HCl in the test "Passive Avoidance of Mice in a Shuttle Chamber". A shuttle chamber (Ugo Basile, Italy) consisted of two sections was used. The walls of one section were opaque while the second section had a transparent cover. The sections were connected through a hole which could be shut with a vertical door. The floor was made of transverse metal bars on which DC current impulses could be fed. Experiments were carried out in aged male mice of BALB/c line weighing 20-24 grams.

On the first day of the experiment 30 minutes before training the mice were injected intraintestinally with physiological solution of scopolamine (0.3 mg/kg) or Scopolamine in combination with antagonists of 5-HT6 receptors 1.2.1(2)HCl, 1.2.1(4)HCl or 1.2.1(5)HCl. Each group consisted of at least 8 animals. The animals were placed in the light section, and the latent period of the first entry into the dark chamber was registered. Then the vertical door was shut and the animal was punished by 0.6 mA DC current for 3 seconds. After that the animal was returned to its living cage. In 22-24 hours the same animal was placed again in the light section of the shuttle chamber and the latent period of its first entry into the dark section, the total time of its stay in the light section and the number of entries into the dark section were registered. Each observation lasted for 5 minutes.

The experiment was carried out during the day time in an isolated laboratory using white noise at a level of about 70 decibel above the human hearing threshold.

Scopolamine causes the disturbance of training (memory loss) which results in an increased latent period of the first entry into the dark section, a longer stay in the light section and a decreased number of entries into the dark section.

The fact that 5-HT$_6$ receptor antagonists can improve the learning ability that has been disturbed by scopolamine is regarded as evidence for their nootropic effect.

The obtained results (see FIGS. 2-4) confirm that 1.2.1(2)HCl, 1.2.1(4)HCl and 1.2.1(5)HCl antagonists of 5-HT$_6$ receptors exhibit a nootropic action which is the most prominent for 1.2.1(2)HCl and 1.2.1(4)HCl antagonists.

EXAMPLE 8

The nootropic action (enhancement of memory disturbed by scopolamine) of antagonists of 5-HT$_6$ receptors of the formulas 1.2.1(1)HCl and 1.2.1(5)HCl in the test "Passive Avoidance of Mice in the Shuttle Chamber". The experiment was carried out as in example 7. On the first day of the experiment 30 minutes before training the mice were injected intraintestinally with a physiological solution of scopolamine (0.3 mg/kg) or MK-801(0.1 mg/kg). Concurrently, before training the mice in the control groups were injected intraintestinally with a physiological solution of scopolamine in combination with antagonists of 5-HT$_6$ receptors 1.2.1(1)HCl, 1.2.1(5)HCl, and scopolamine in combination with control antagonists of 5-HT$_6$ receptors SB-742457 (1 mg/kg, 15 minutes before training) and PRX-07034 (10 mg/kg, 30 minutes before training).

The results obtained (FIGS. 5-10) testify the ability of anatagonists of 5-HT$_6$ receptors 1.2.1(1)HCl and 1.2.1(5)HCl to act as nootropic; the effect is the most prominent for 1.2.1 (1)HCl and 1.2.1(5)HCl antagonists. Besides the test demonstrated the highest activity for 1.2.1(1)HCl antagonist, while the control antagonist SB-742457 proved to be inactive.

EXAMPLE 9

The nootropic action (enhancement of memory disturbed by Scopolamine) of antagonists of 5-HT$_6$ receptors of the formulas 1.2.1(1)HCl and 1.2.1(5)HCl in the test "Mice Training in the Morris Water maze". A round pool of 100 cm in diameter and sides height of 30 cm was used. It was filled with water at 20-22° C. A round ceramic platform of 14 cm height was placed in the pool. Animals's behavior was registered with an automated computer video system in combination with software package of movement analysis Any-maze (Stoelting Co., US). The experiments were carried out on aged male mice of BALB/c line weighing 20-24 grams. Before the experiments mice suitable for training were selected. This was done by placing the platform 1 cm above the water level and putting an animal on the platform for 20 seconds. Then the mouse was sunk into the water on the opposite side of the pool, allowed to find the platform and climb it for 60 seconds, where it was left for additional 20 seconds. After that the mouse was repeatedly immersed into the water on the opposite side of the pool and allowed to look for the platform. If it failed in finding the platform within 60 seconds the experimentator helped it to find the platform and climb it. If the mice couldn't find the platform itself in two consecutive attempts it was excluded from the experiment.

During the next two days the platform was placed 0.5 cm lower the water level. Every day the mice were given four attempts for finding the platform within 60 seconds. The time interval between the attempts was 20 seconds, during which the mice stayed on the platform. Every day before the first attempt the mice was placed on the platform for 20 seconds. The time needed for finding and climbing the platform was registered. The animals were sunk into water in two different places on the side of the pool opposite to the platform. On each day of two-day experiment 35-40 minutes before training the mice were injected intraintestinally with Scopolamine (0.6 mg/kg), Scopolamine in combination with Tacrine (3 mg/kg), Scopolamine in combination with antagonist of 5-HT$_6$ receptors 1.2.1(5)HCl (0.1 mg/kg) or Scopolamine together with antagonist of 5-HT$_6$ receptor 1.2.1(1)HCl (1 mg/kg).

The animals of the control group were injected with physiological solution. At least 8 animals were used in each group.

On the third day the platform was removed and each animal was placed one time into the pool for a period of 60 seconds. The time each mouse spent in the area where the platform had been located during the previous days was registered. This time interval was regarded as a measure of training effectiveness carried out during the previous two days.

The animals of the control group were trained successfully over the first 2 days; that was confirmed by the prolonged periods of time they spent on the third day in the area where the platform had been. The administration of 0.6 mg/kg of Scopolamine totally damaged training under the conditions of the above experiment, which was confirmed by the relatively short period of time the mice injected with scopolamine spent in the area where the platform had been. Antagonists of 5-HT$_6$ receptors 1.2.1(1)HCl and 1.2.1(5)HCl and 3 mg/kg of Tacrine caused a statistically significant improvement of mice's training (FIG. 11-12).

EXAMPLE 10

The nootropic action (enhancement of memory disturbed by Scopolamine) of 5-HT$_6$ receptors antagonists of the formulas 1.2.1(1)HCl and 1.2.1(5)HCl in the test "Novel object recognition by mice against the background of Scopolamine and MK-801". The experiments were carried out in a cross like maze which consisted of 4 peripheral arms connected with the central chamber by 7×7 cm holes. The maze was made of black plastic and its arms were of 14×14×14 cm size. The top cover of the maze was transparent.

A mouse was placed in the central chamber of the maze and allowed to investigate the environment. Criterion of entering an arm by the animal was detecting of all its paws inside the arm. The test was considered to be completed when the mouse had accomplished 12 transitions between the arms (having made 13 visits). The floor of the maze was cleaned after each animal.

The test was carried out twice with each mouse with 1 hour interval.

During the first test each arm of the maze contained a circular plastic cup of 3 cm height and 7 cm diameter. In the second test the cover of each two opposing arms was replaced by a conical glass flask of 7 cm height and 4 cm across the bottom. The time the mouse spent in each arm of the maze was registered and the index of novel object recognition was calculated as the ratio of the time the mouse spent in the arms with the flasks to the time it spent in all arms of the maze. If no preference was given to the arms with novel objects the index was 0.5.

The mice spend more time in the arm containing novel objects that results in an increasing of recognition index. Scopolamine (1 mg/kg) and MK-801 (0.2 mg/kg) disturbed learning (memory) that leads to the lowering of recognition index. The ability of 5-HT$_6$ receptors antagonists 1.2.1(1)HCl and 1.2.1(5)HCl to improve new object recognition is regarded as evidence of their nootropic action.

The results obtained show the ability of Memantine, SB-742457, 1.2.1(1)HCl, and 1.2.1(5)HCl to nootropic action, the level of which is the most prominent for 5-HT$_6$ receptor antagonist 1.2.1(1)HCl (FIG. 13-14).

EXAMPLE 11

The antidepressant action of antagonist of 5-HT$_6$ receptor 1.2.1(1)HCl in the test "Mice Behavior in Porsolt's Forced Swim Test". A plastic vessel filled with water to height of 18 cm at 20-22° C. was used. The experiments were carried out on aged male mice of BALB/c line weighing 20-24 grams. Each animal was placed in water and the time of motionless hanging in water was registered during 15 minutes—so named behavior of "despair" which is the measure of depressively-like condition. The last five minutes of the test were used in analysis. Automated computerized detection of motion with video system and Any-maze program were utilized in the experiment. This index is reduced when antidepressants are administered (FIGS. 15-16).

EXAMPLE 12

The antidepressant action of antagonist of 5-$HT_6$ receptor 1.2.1(1)HCl in the test "Mice behavior in the tail suspension test". The experiments were carried out on aged male mice of BALB/c line weighing 20-24 grams. In the test the mice were suspended by the tail with a sticky tape on the holder over a horizontal surface at a height of 40 cm, and during 3 minutes the total time of episodes of complete immobility which is the measure of depressively-like condition was recorded. Automated computerized detection of motion with video system and Any-maze program were used in the experiment. The duration of complete immobility was reduced when antidepressants were administered (FIGS. 17-18).

EXAMPLE 13

The tranquilizing action of antagonists of 5-$HT_6$ receptors 1.2.1(1)HCl and 1.2.1(5)HCl in the test "Mice Behavior in the Elevated. Plus Maze". The length of each arm in the labyrinth was 30 cm, the width was 5 cm, the height of the walls was 15 cm. Two opposite arms were closed from sides and end faces by transparent walls, the other two arms were lit and opened. A mouse was placed in the center of the maze and for the next five minutes the number of entries the open and closed sections and the time spent in each type of arms was registered. These data were used to calculate the indexes of preference for the open arms as the ratio of the number of the open arm entries, as well as the total time spent there to the whole number of entries to all arms and the total time spent there. The animals usually avoid the open arms (the preference index is between 0.2 and 0.3). Compounds with tranquilizing action increase this index up to 0.5-0.6 or even more and reduce the number of defecations without altering the overall motion activity of the mice (the total number of their entries the arms).

The results obtained show (FIG. 19-21) that Buspiron, 1.2.1(1)HCl and 1.2.1(5)HCl exhibit a tranquilizing action, which is the most prominent for compound 1.2.1(1)HCl.

EXAMPLE 13

The tranquilizing action of antagonists of 5-$HT_6$ receptors 1.2.1(1)HCl and 1.2.1(5)HCl in the test "Mice Behavior in the Elevated Plus Maze". The length of each arm in the labyrinth was 30 cm, the width was 5 cm, the height of the walls was 15 cm. Two opposite arms were closed from sides and end faces by transparent walls, the other two arms were lit and opened. A mouse was placed in the center of the maze and for the next five minutes the number of entries the open and closed sections and the time spent in each type of arms was registered. These data were used to calculate the indexes of preference for the open arms as the ratio of the number of the open arm entries, as well as the total time spent there to the whole number of entries to all arms and the total time spent there. The animals usually avoid the open arms (the preference index is between 0.2 and 0.3). Compounds with tranquilizing action increase this index up to 0.5-0.6 or even more and reduce the number of defecations without altering the overall motion activity of the mice (the total number of their entries the arms).

The results obtained testify (FIG. 19-21) that Buspiron, 1.2.1(1)HCl and 1.2.1(5)HCl exhibit a tranquilizing action, which is the most prominent for compound 1.2.1(1)HCl.

EXAMPLE 14

Preparation of a medicine in the form of tablets. 1600 mg Of starch, 1600 mg of grained lactose, 400 mg of talcum and 1000 mg of 2,8-dimethyl-5-[2-(pyridin-4-yl)ethyl]-2,3,4,5-tetrahydro-1H-pyrido[4,3-b]indole hydrochloride 1.2.1(2) were mixed together and pressed in a brick. Prepared brick was crushed to granules and riddled through sieves, gathering granules of 14-16 mesh size. The obtained granules were pelletized in the tablets of suitable form 560 mg by weight each. According to the invention pharmaceutical compositions in the form of tablets comprising other substituted 2,3,4,5-tetrahydro-1H-pyrido[4,3-b]indoles of the general formula 1 as a biological active ingredient could be prepared in a similar way.

EXAMPLE 15

Preparation of a medicine in the form of capsules. 2,8-Dimethyl-5-[2-(pyridin-4-yl)ethyl]-2,3,4,5-tetrahydro-1H-pyrido[4,3-b]indole hydrochloride 1.2.1(2) was carefully mixed with a powder of lactose in ratio 2:1. The prepared powdery mixture was packed on 300 mg into gelatinous capsules of suitable size.

EXAMPLE 16

Preparation of a Medicine in the Form of Compositions for Intramuscular, intraperitoneal or hypodermic injections. 500 mg Of 2,8-dimethyl-5-[2-(pyridin-4-yl)ethyl]-2,3,4,5-tetrahydro-1H-pyrido[4,3-b]indole hydrochloride 1.2.1(2) were mixed with 300 mg of chlorobutanole, 2 ml of propylene glycol and 100 ml of water for injections. The prepared solution was filtered and placed in 1 ml ampoules which were sealed up and sterilized in an autoclave.

INDUSTRIAL APPLICABILITY

The invention could be used in medicine, veterinary, biochemistry.

What is claimed is:

1. A compound of the formula 1; or a pharmaceutically acceptable salt, or hydrate thereof:

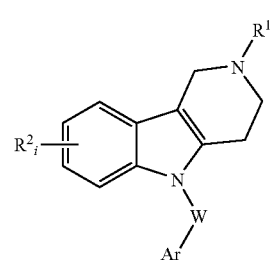

wherein $R^1$ is $C_1$-$C_5$ alkyl;

$R^2_i$ is independently hydrogen, halogen, $C_1$-$C_3$ alkyl, $CF_3$, $OCF_3$ or $OCH_3$;

i is 1, 2, 3, or 4;

Ar is unsubstituted phenyl or substituted phenyl substituted with halogen, $C_1$-$C_6$ alkyl, $C_1$-$C_6$ alkoxy, a substituted amino group or trifluoromethyl; or Ar is a substituted or unsubstituted 6-membered aromatic heterocycle one or, with two nitrogen atoms in the heterocycle; and W is an ethenyl group or ethynyl group.

2. The compound according to claim 1, wherein W is an ethenyl group.

3. The compound according to claim 2, wherein the compound is:

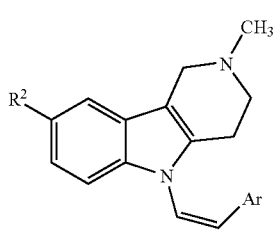

1.1.1

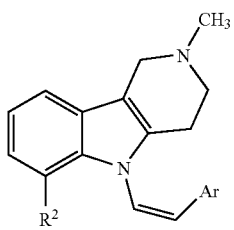

1.1.2

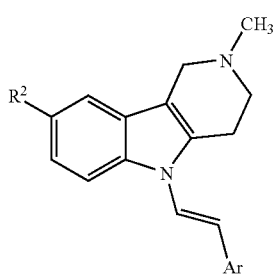

1.1.3

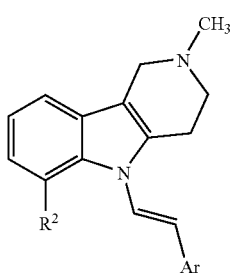

1.1.4 wherein $R^2$ is hydrogen, F, $CH_3$, $CF_3$, $OCF_3$ or $OCH_3$; and

Ar is substituted phenyl or substituted pyridyl.

4. The compound according to claim 2, wherein the compound is:

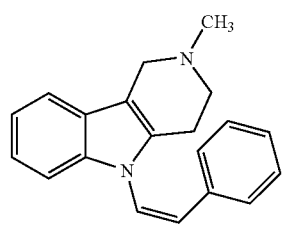

1.1(1)

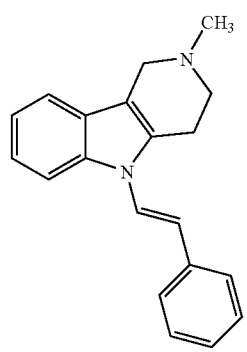

1.1(2)

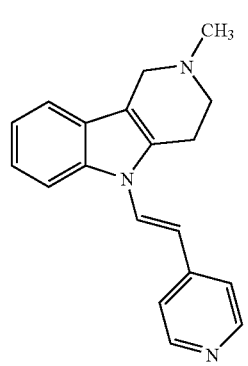

1.1(3)

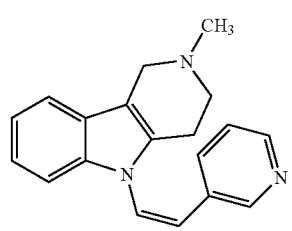

1.1(4)

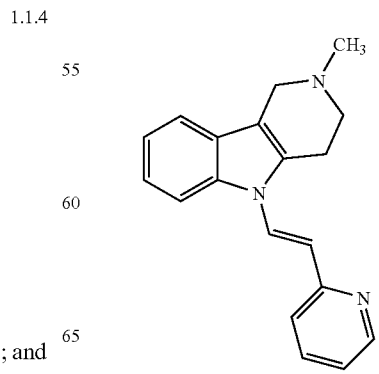

1.1(5)

1.1(6)
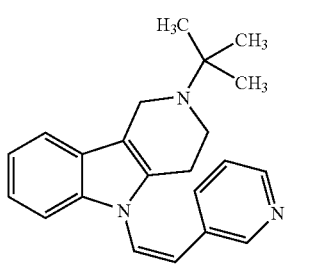
1.1.1(1)
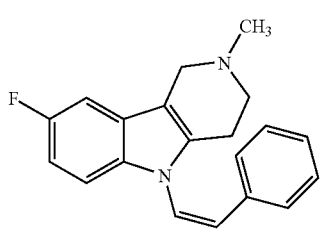
1.1.3(1)
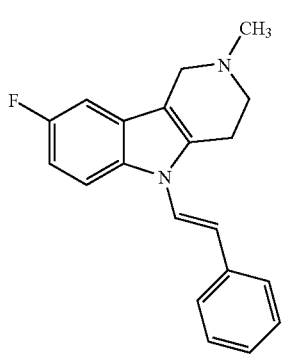
1.1.3(2)
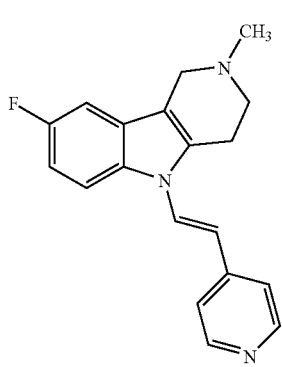
1.1.1(2)
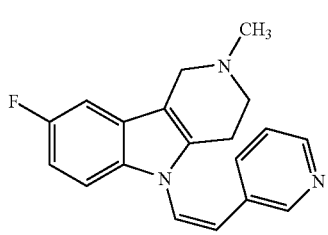
1.1.3(3)
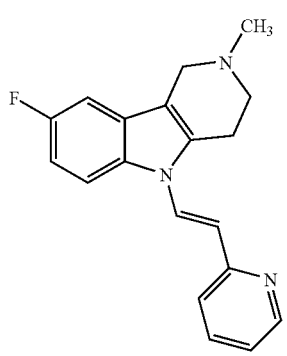
1.1.1(3)
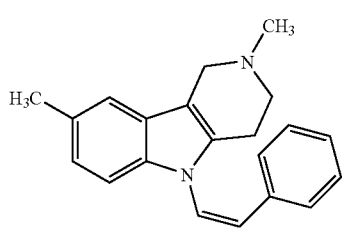
1.1.3(4)
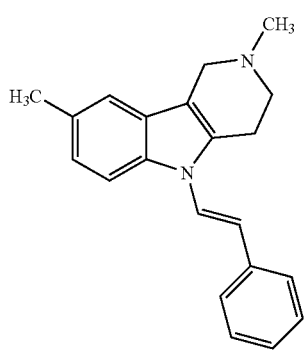
1.1.1(4)
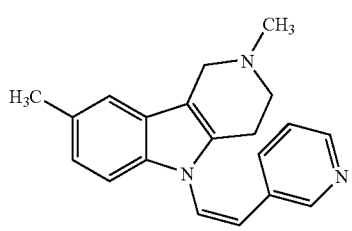
1.1.3(5)
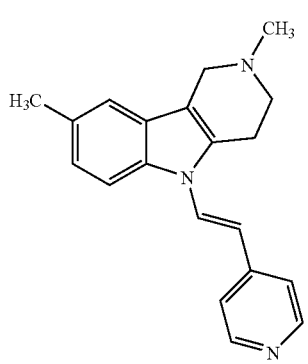

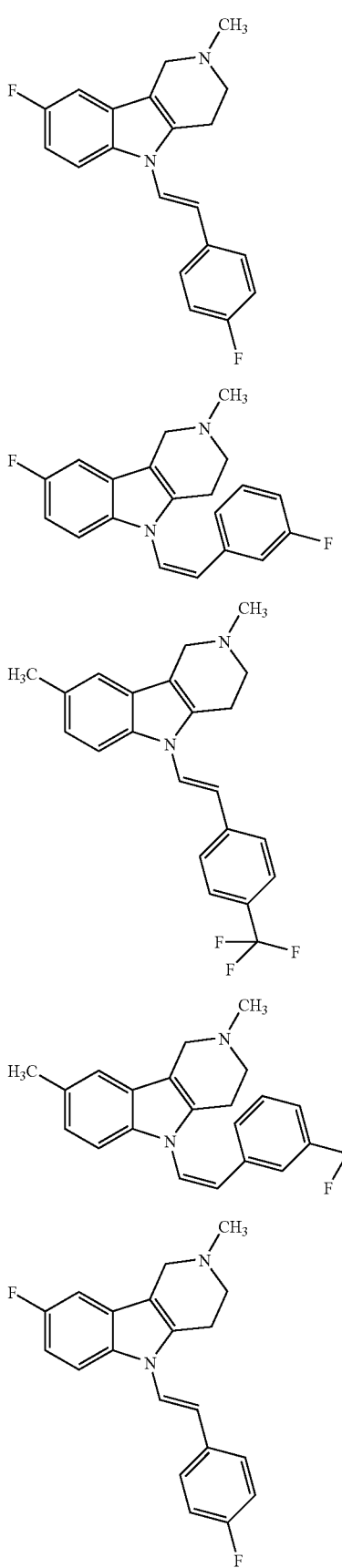
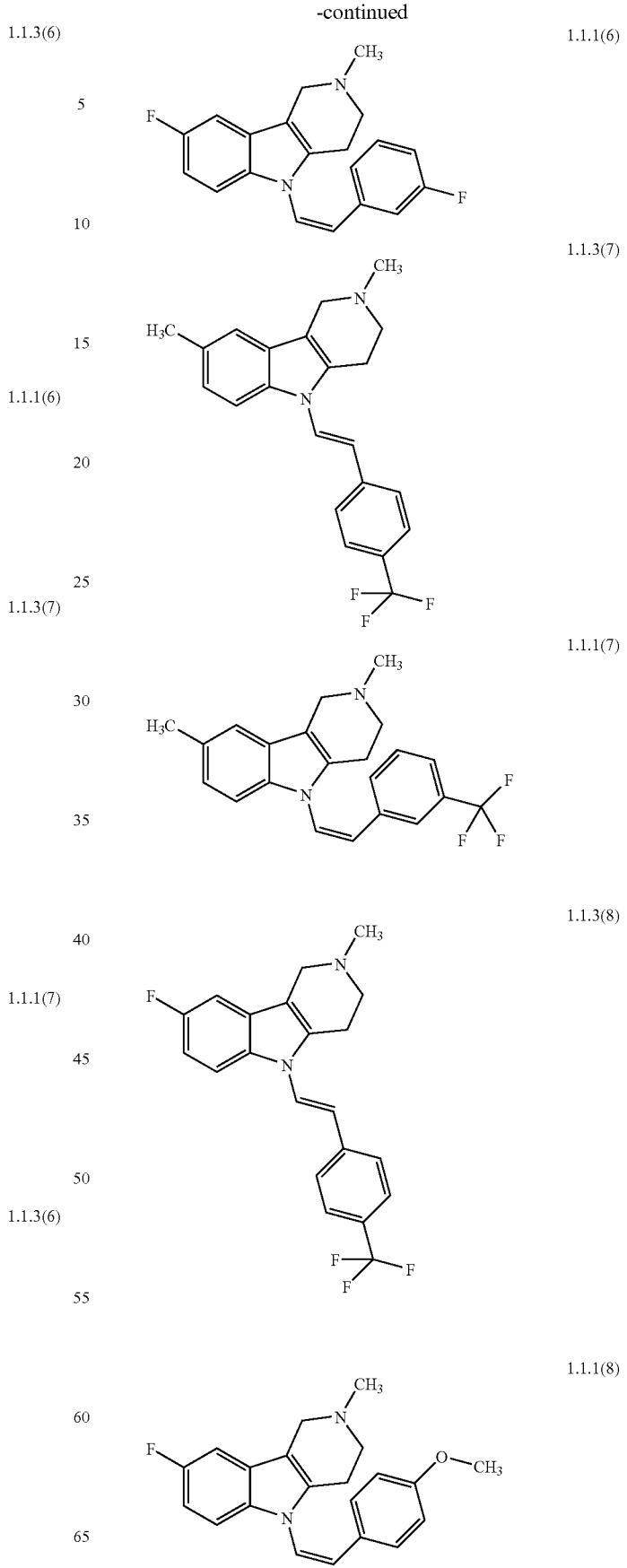

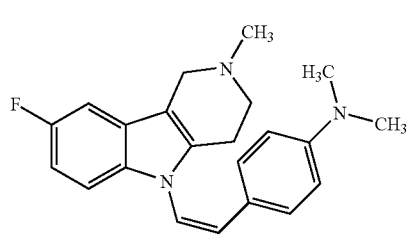
1.1.1(9)
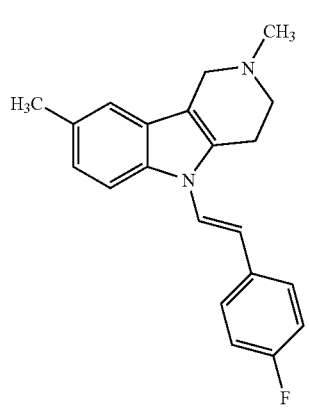
1.1.3(9)
or a pharmaceutically acceptable salt or hydrate thereof.
5. The compound according to claim 1, of the formula 1.3, or a pharmaceutically acceptable salt or hydrate thereof:
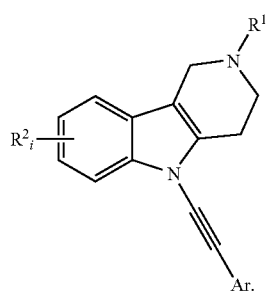
1.3
6. The compound according to claim 5, wherein the compound is:
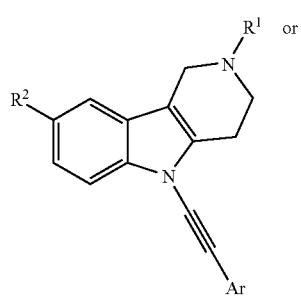
1.3.1 or
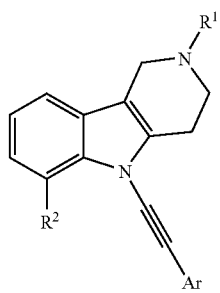
1.3.2
wherein $R^2$ is hydrogen, F, $CH_3$, $CF_3$, $OCF_3$ or $OCH_3$.
7. The compound according to claim 6, wherein the compound is:
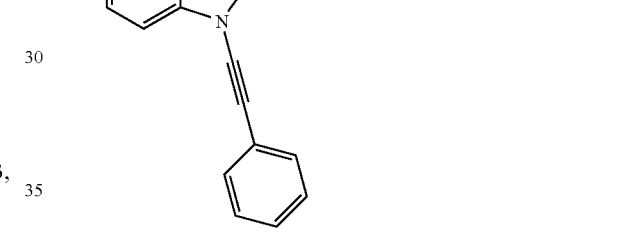
1.3(1)
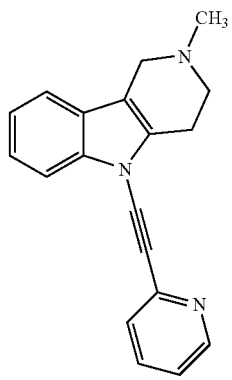
1.3(2)
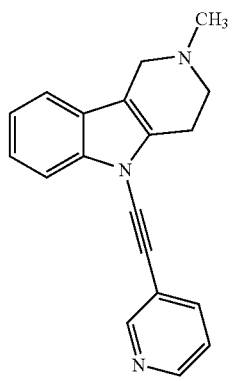
1.3(3)

1.3(4)
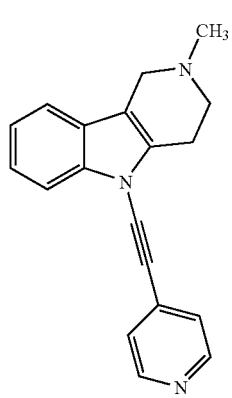
1.3.1(3)
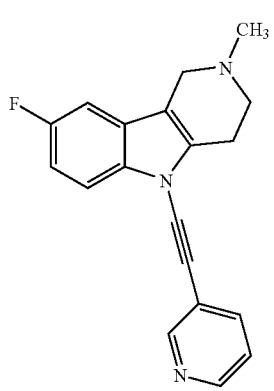
1.3(5)
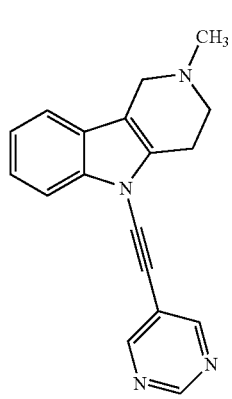
1.3.1(4)
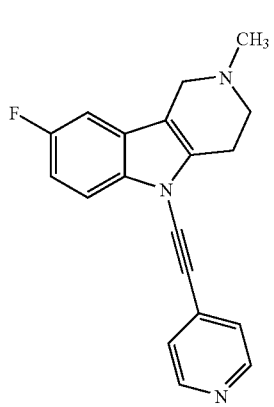
1.3.1(1)
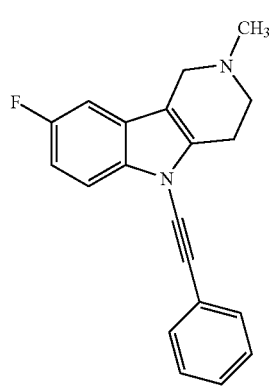
1.3.2(1)
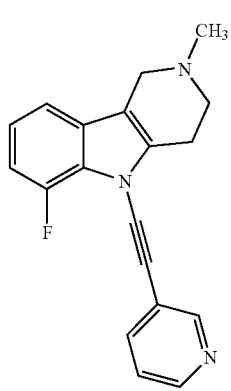
1.3.1(2)
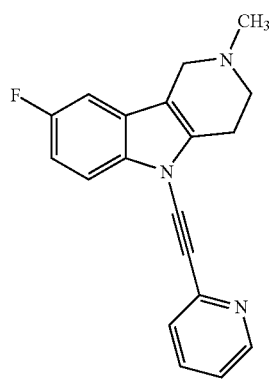
1.3.1(5)
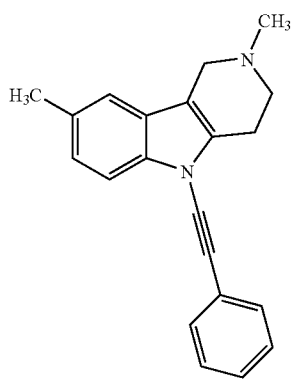

1.3.1(6)
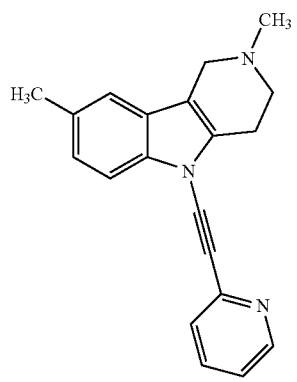
1.3.1(7)
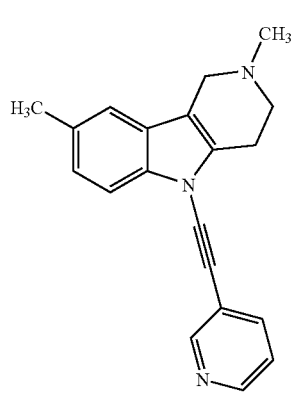
1.3.1(8)
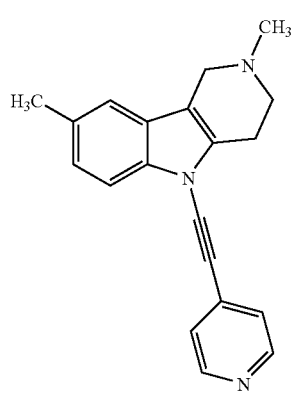
1.3.1(9)
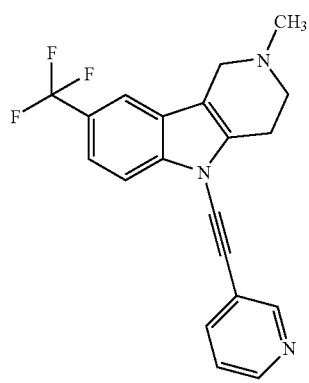
1.3.1(10)
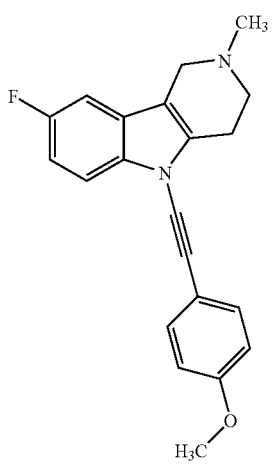
1.3.1(11)
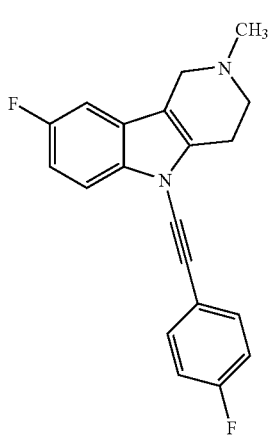
1.3.1(12)
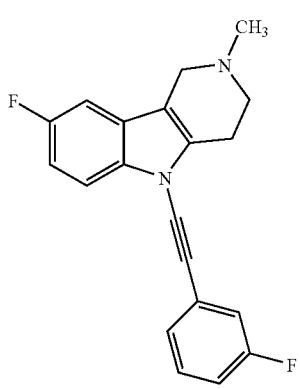

105
-continued
1.3.1(13)
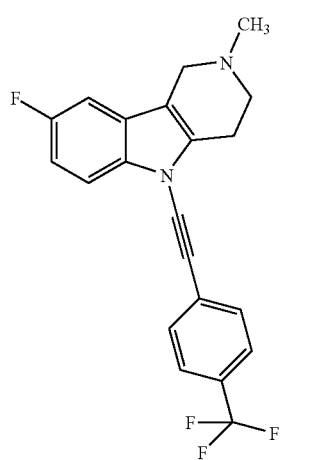
1.3.1(14)
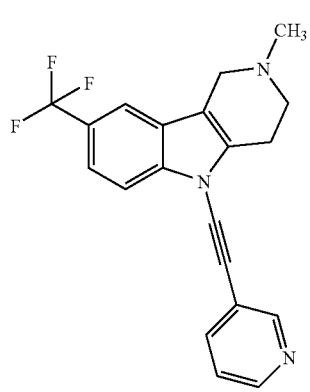
1.3.1(15)
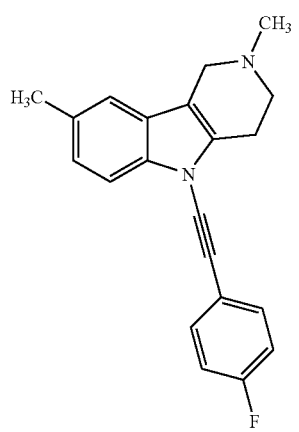
1.3.1(16)
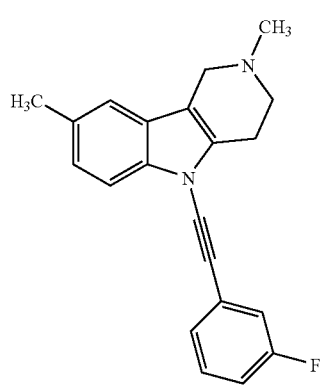
106
-continued
1.3.1(17)
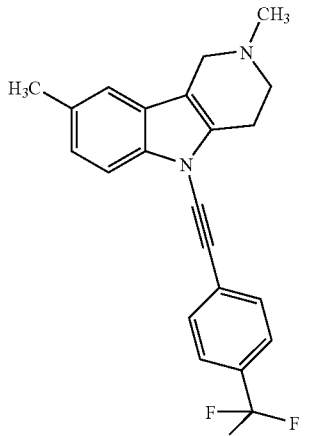
1.3.1(18)
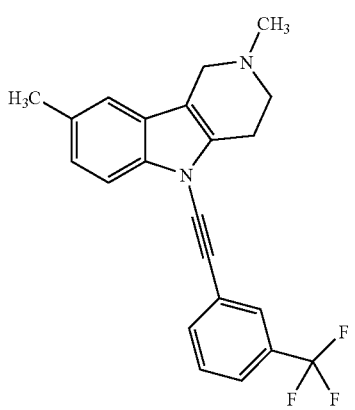
1.3.1(19)
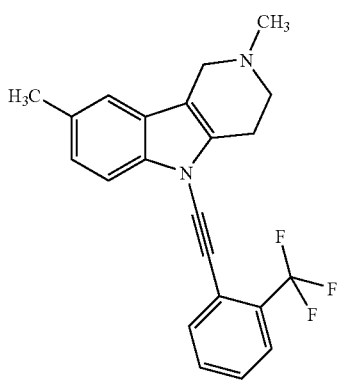
1.3.1(20)
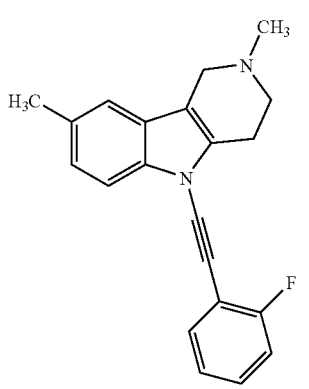

-continued 1.3.1(21)

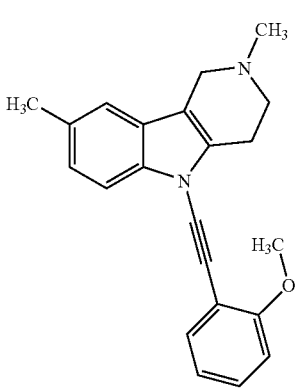

1.3.1(24)

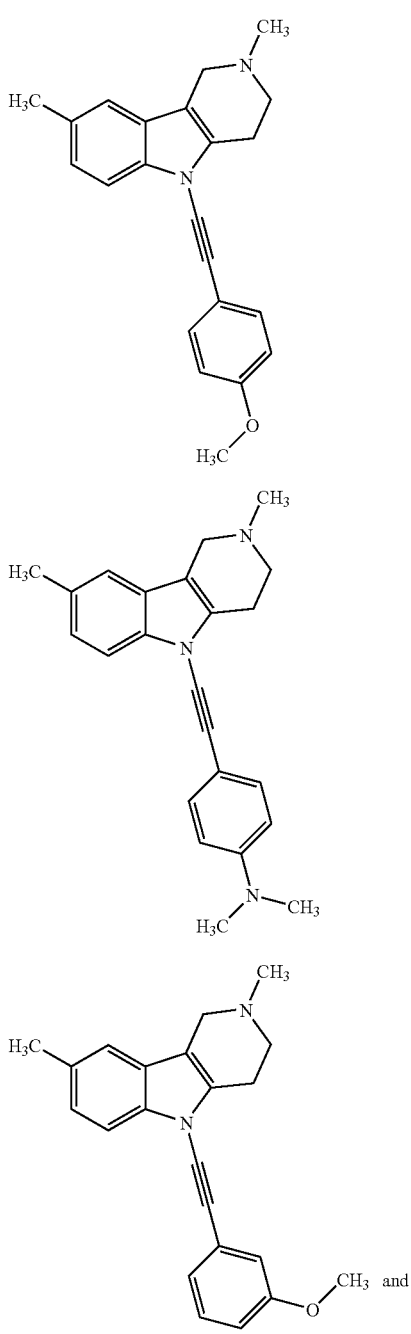

1.3.1(22)

1.3.1(23)

or a pharmaceutically acceptable salt or hydrate thereof.

8. A pharmaceutical composition comprising a compound or a pharmaceutically acceptable salt or hydrate thereof, of claim 1 and a pharmaceutically acceptable carrier.

9. The pharmaceutical composition according to claim 8, which is in the form of a tablet, capsule or an injectable liquid.

10. A method of antagonizing a 5-HT$_6$ serotonin receptor and simultaneously regulating $Ca^{+2}$ ion homeostasis in a cell, comprising administering to the cell a compound of claim 1; or a pharmaceutically acceptable salt or hydrate thereof.

11. A pharmaceutical composition comprising a compound of claim 1, or a pharmaceutically acceptable salt or hydrate thereof, and a drug substance selected from the group consisting of a non-steroidal anti-inflammatory drug, inhibitor of acetylcholinesterase, NMDA-receptor antagonist, nootropic drug, AMRA receptor modulator, monoaminooxidase MAO-B or MAO-A inhibitor, antiamiloidogen drug, substance lowering beta-amyloid neurotoxicity, antagonist of GAMK (B) receptor, monoclonal antibody, antioxidant, neurotrophic agent, antidepressant, anorexic drug, hormonal drug, statin, hypoglycemic drug, and inhibitor of enzymes of fatty acid synthesis in the form of a tablet, capsule or injection placed in a pharmaceutically acceptable packing.

* * * * *